(12) United States Patent
Harada et al.

(10) Patent No.: US 11,909,397 B2
(45) Date of Patent: Feb. 20, 2024

(54) DETECTING DEVICE AND SEMICONDUCTOR DEVICE

(71) Applicant: Semiconductor Energy Laboratory Co., Ltd., Atsugi (JP)

(72) Inventors: Shintaro Harada, Kawasaki (JP); Takayuki Ikeda, Atsugi (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 475 days.

(21) Appl. No.: 17/286,091

(22) PCT Filed: Oct. 17, 2019

(86) PCT No.: PCT/IB2019/058844
§ 371 (c)(1),
(2) Date: Apr. 16, 2021

(87) PCT Pub. No.: WO2020/084407
PCT Pub. Date: Apr. 30, 2020

(65) Prior Publication Data
US 2021/0359669 A1 Nov. 18, 2021

(30) Foreign Application Priority Data

Oct. 25, 2018 (JP) .................. 2018-200807
Nov. 30, 2018 (JP) .................. 2018-225060

(51) Int. Cl.
*H02J 7/00* (2006.01)
*H03K 3/037* (2006.01)
(Continued)

(52) U.S. Cl.
CPC ......... *H03K 3/037* (2013.01); *G01R 31/3644* (2013.01); *G01R 31/3835* (2019.01); *G06F 1/06* (2013.01)

(58) Field of Classification Search
CPC ............. H03K 3/037; H03K 3/356026; H03K 3/356078; H03K 23/40; H03K 21/12;
(Continued)

(56) References Cited

U.S. PATENT DOCUMENTS 7,218,160 B2  5/2007  Wada et al.
7,729,141 B1 * 6/2010  Chui .................. H02M 3/07
                                                    363/60
(Continued)

FOREIGN PATENT DOCUMENTS

JP  51-112142 A  10/1976
JP  60-010498 A   1/1985
(Continued)

OTHER PUBLICATIONS

International Search Report (Application No. PCT/IB2019/058844) dated Feb. 10, 2020.
(Continued)

*Primary Examiner* — Jack Chiang
*Assistant Examiner* — Brandon Bowers
(74) *Attorney, Agent, or Firm* — Eric J. Robinson; Robinson Intellectual Property Law Office, P.C.

(57) ABSTRACT

The power of a semiconductor device is reduced. The semiconductor device includes a latch circuit composed of a dynamic circuit. The latch circuit includes a first circuit having a decoding function, a plurality of capacitors, a plurality of clock input terminals, a signal input terminal, a first output terminal, and a second output terminal. In a period during which "H" is supplied to a first clock signal, the potential of the first capacitor is updated on the basis of the results of decoding performed by the first circuit. In a period during which "H" is supplied to a second clock signal, the potential of the second capacitor is updated on the basis of the potential of the first capacitor, and the potential
(Continued)

of the second capacitor is supplied as a first output signal to the first output terminal. In a period during which "H" is supplied to a third clock signal, the potential of the third capacitor is updated on the basis of the potential of the second capacitor, and the potential of the third capacitor is supplied as a second output signal to the second output terminal.

6 Claims, 23 Drawing Sheets

(51) Int. Cl.
  *G01R 31/3835* (2019.01)
  *G01R 31/36* (2020.01)
  *G06F 1/06* (2006.01)

(58) Field of Classification Search
  CPC ... G01R 31/3644; G01R 31/3835; G06F 1/06; G06F 1/04; G06F 1/163; G06F 1/28; G06F 1/3234; A61B 5/0022; A61B 5/01; A61B 5/024; A61B 5/11; A61B 5/14532; A61B 5/363; A61B 5/681; G11C 19/28; H01L 21/8234; H01L 27/088; H01L 29/786
  See application file for complete search history.

(56) References Cited

U.S. PATENT DOCUMENTS

| 9,438,234 | B2 | 9/2016 | Maehashi et al. |
| 2013/0214851 | A1* | 8/2013 | Fifield .................... H02M 3/07 327/536 |
| 2015/0036445 | A1* | 2/2015 | Yoshida ............ G11C 11/40611 365/222 |
| 2016/0356855 | A1* | 12/2016 | Tamegai ............... H01M 10/44 |

FOREIGN PATENT DOCUMENTS

| JP | 07-177000 A | 7/1995 |
| JP | 2000-349163 A | 12/2000 |
| JP | 2006-066938 A | 3/2006 |
| JP | 2016-105590 A | 6/2016 |

OTHER PUBLICATIONS

Written Opinion (Application No. PCT/IB2019/058844) dated Feb. 10, 2020.

* cited by examiner

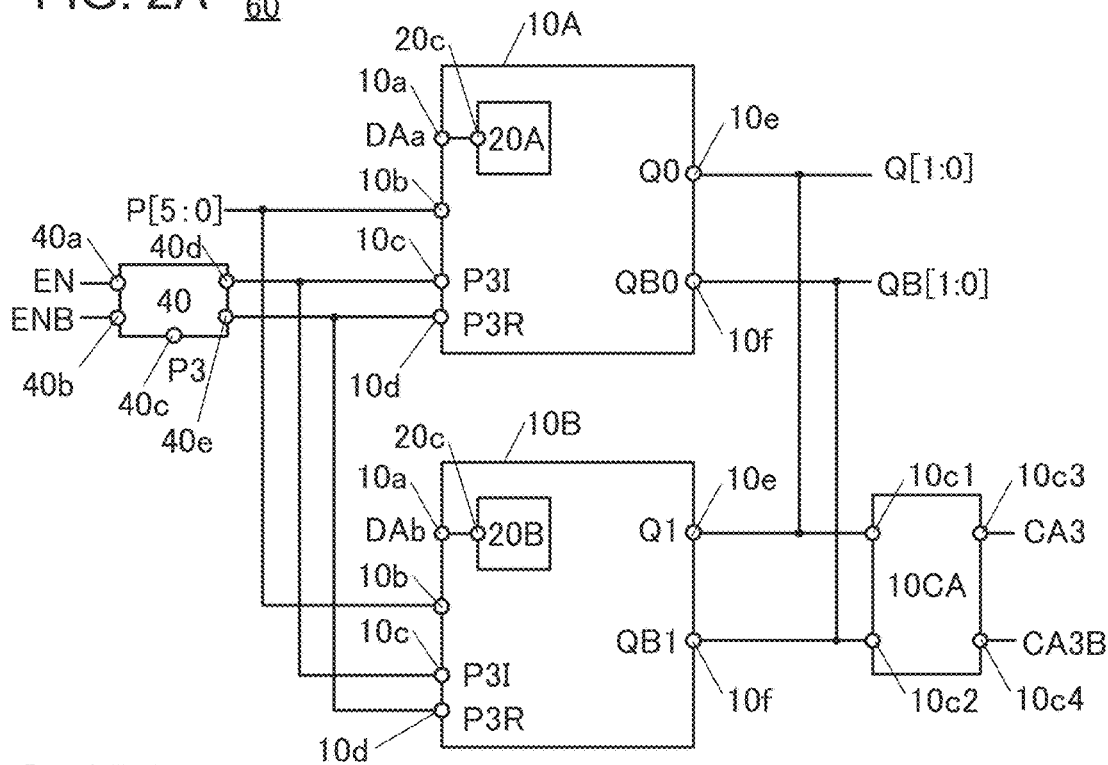
FIG. 2A
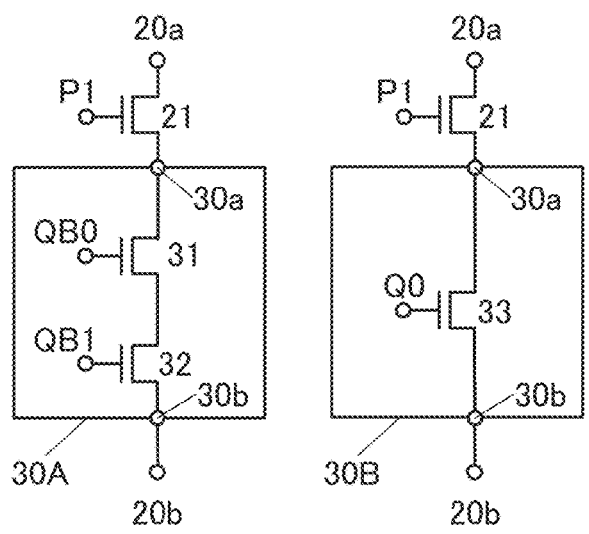
FIG. 2B1  20A
FIG. 2B2  20B
DAa=QB0·QB1
DAb=Q0
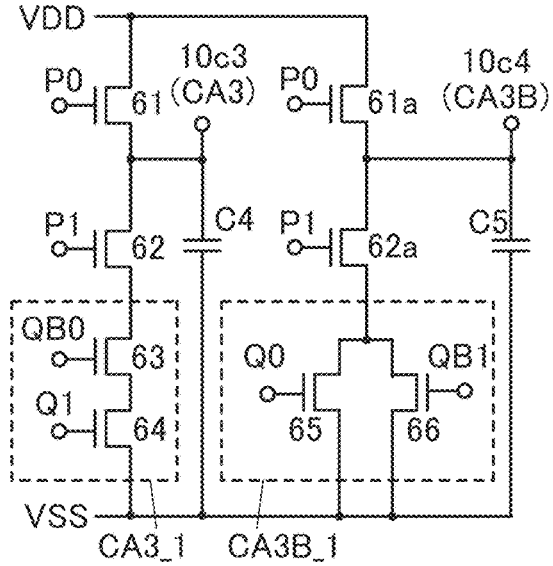
FIG. 2C  10CA
CA3_1=QB0·Q1   CA3B_1=Q0+QB1

FIG. 4A1
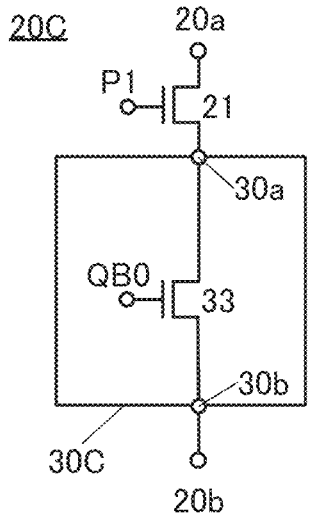
DAc=QB0
FIG. 4A2
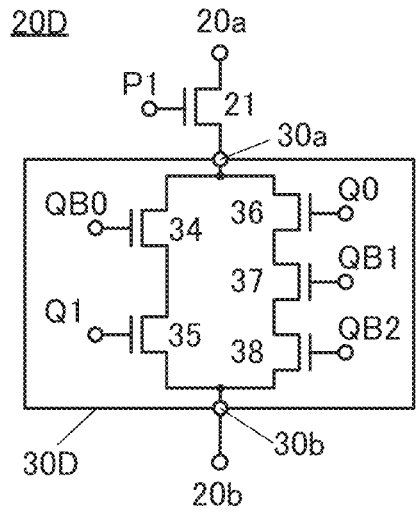
DAd=QB0·Q1+Q0·QB1·QB2
FIG. 4A3
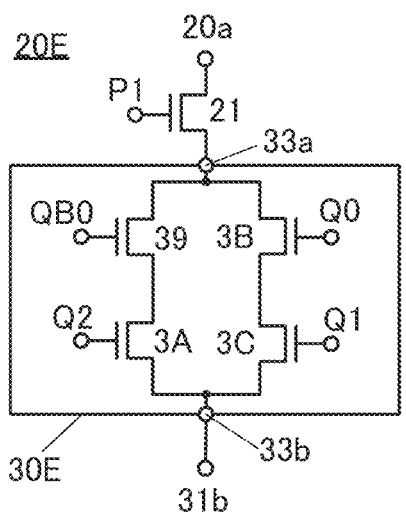
DAe=QB0·Q2+Q0·Q1
FIG. 4B
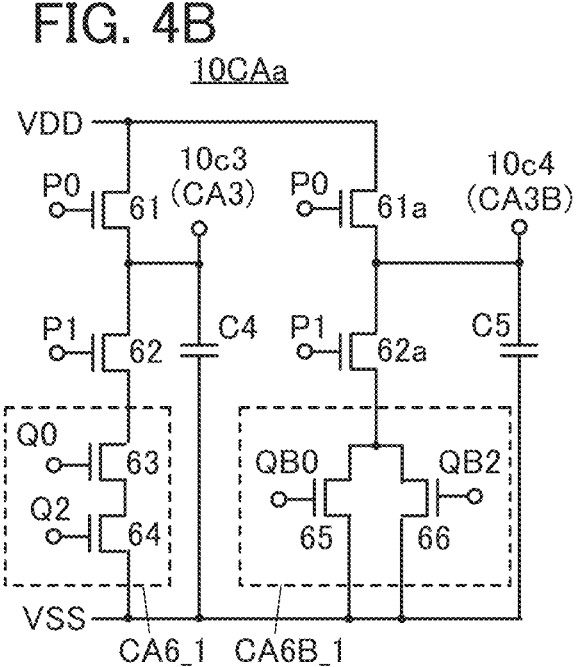
CA6_1=Q0·Q2    QA6B_1=Q0+QB2

FIG. 6A1
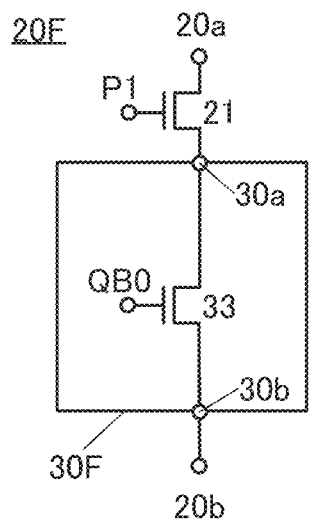
DAf=QB0
FIG. 6A2
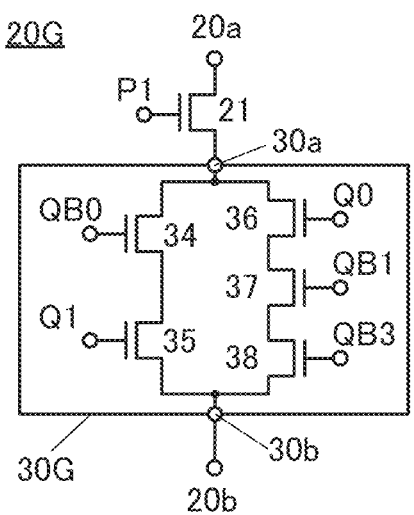
DAg=QB0·Q1+Q0·QB1·QB3
FIG. 6A3
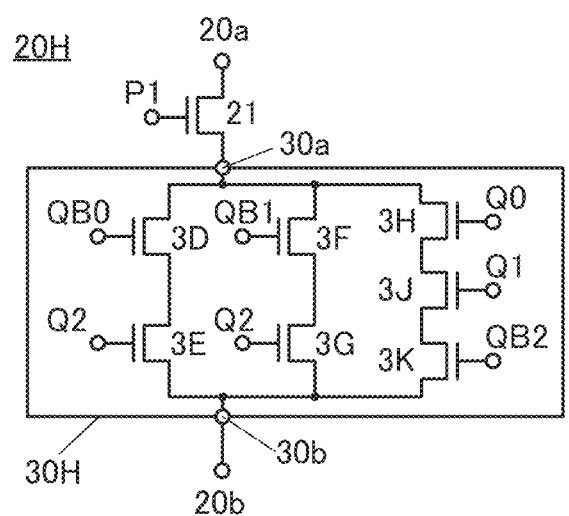
DAh=QB0·Q2+QB1·Q2+Q0·Q1·QB2
FIG. 6A4
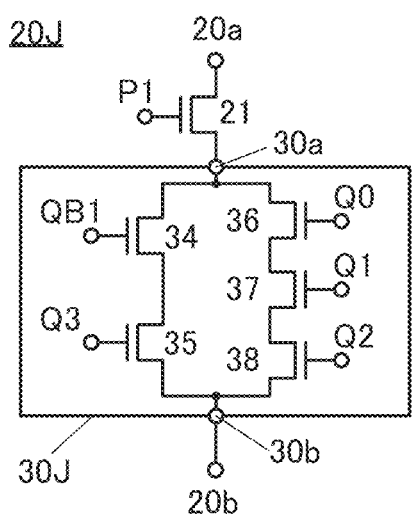
DAj=QB1·Q3+Q0·Q1·Q2

DA=QB

DA=QB

FIG. 19A1
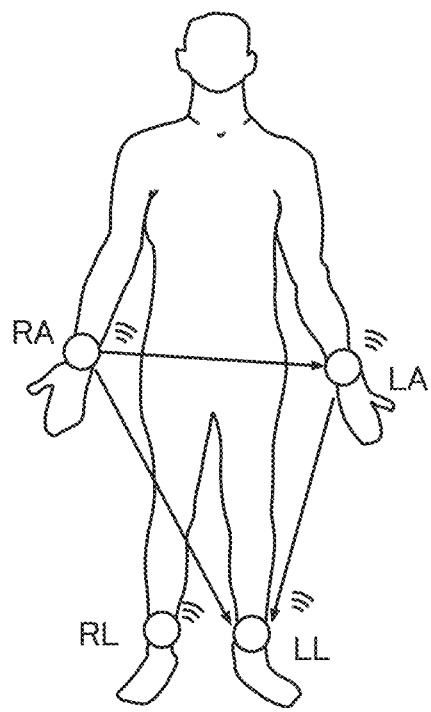
FIG. 19A2
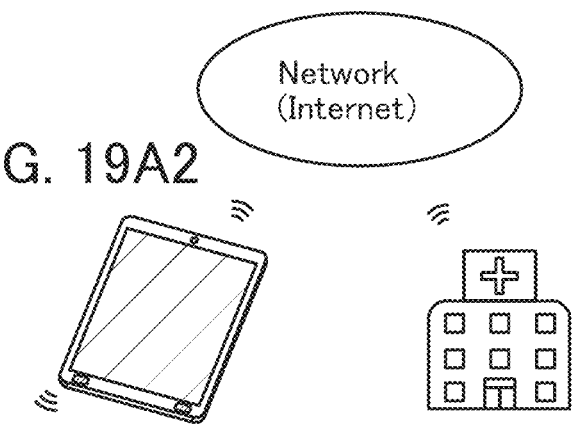
FIG. 19B1  FIG. 19B2  FIG. 19B3  FIG. 19B4
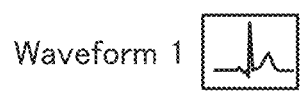 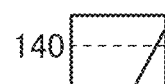 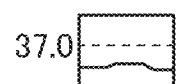 
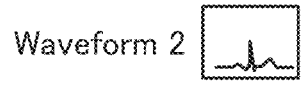 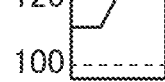 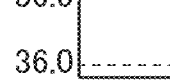 
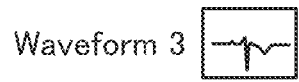   

DETECTING DEVICE AND SEMICONDUCTOR DEVICE

TECHNICAL FIELD

One embodiment of the present invention relates to a latch circuit, a counter circuit, a detecting device, a battery monitor device, and a semiconductor device.

One embodiment of the present invention relates to an object, a method, or a manufacturing method. Alternatively, the present invention relates to a process, a machine, manufacture, or a composition (a composition of matter). One embodiment of the present invention relates to a semiconductor device, a display device, a light-emitting device, a power storage device, a lighting device, or an electronic device. In addition, one embodiment of the present invention relates to a method of controlling charge of a power storage device, a method of estimating the state of a power storage device, and a detecting device used for sensing anomaly of a power storage device. In particular, one embodiment of the present invention relates to a charge system of a power storage device, a state estimation system of a power storage device, and an anomaly detecting system of a power storage device. An electronic device including the detecting device of one embodiment of the present invention includes medical equipment that detects a body condition.

In this specification and the like, a semiconductor device means an element, a circuit, a device, or the like that can function by utilizing semiconductor characteristics. For example, a semiconductor element such as a transistor or a diode is a semiconductor device. For another example, a circuit including a semiconductor element is a semiconductor device. For another example, a device provided with a circuit including a semiconductor element is a semiconductor device.

BACKGROUND ART

In recent years, a variety of power storage devices such as lithium-ion secondary batteries, lithium-ion capacitors, and air batteries have been actively developed. In particular, demand for lithium-ion secondary batteries with high output and high energy density has rapidly grown with the development of the semiconductor industry for portable information terminals such as mobile phones, smartphones, tablets, and laptop computers; game machines; portable music players; digital cameras; medical equipment; next-generation clean energy vehicles such as hybrid electric vehicles (HEVs), electric vehicles (EVs), and plug-in hybrid electric vehicles (PHEVs); electric bikes; and the like, and lithium-ion secondary batteries have become essential as rechargeable energy supply sources for the modern information society.

In the design capacity (DC) of a secondary battery (including a lithium-ion secondary battery), the proportion of the remaining capacity (RC) in the full charge capacity (FCC) of the battery, that is, the state of charge (SOC), is not set to use all of the design capacity from 0% to 100%, and a margin of approximately 5% (or 10%) from 0% is provided to prevent overdischarge. In addition, to prevent overcharge, a margin of approximately 5% (or 10%) from 100% is also provided; accordingly, a design capacity within a range of 5% to 95% (or within a range of 10% to 90%) is said to be used. In practice, a design capacity within a range of 5% to 95% (or within a range of 10% to 90%) is used by setting the voltage range of an upper limit voltage $V_{max}$ and a lower limit voltage $V_{min}$ using a BMS (Battery Management System) connected to a secondary battery.

A secondary battery is degraded by charging and discharging, a change over time, a temperature change, or the like. Thus, the secondary battery can be managed by accurately determining the state of the inside of the secondary battery, particularly the SOC (state of charge). By accurately determining the SOC, the voltage range between the upper limit voltage $V_{max}$ and the lower limit voltage $V_{min}$ can be widened. Managing the secondary battery requires a detecting device that accurately determines the state of the inside of the secondary battery, particularly the SOC (state of charge). In addition, the power consumption of the detecting device needs to be reduced.

Patent Document 1 shows an example of a semiconductor integrated circuit for reducing power consumption.

REFERENCE

Patent Document

[Patent Document 1] Japanese Published Patent Application No. 2006-66938

SUMMARY OF THE INVENTION

Problems to be Solved by the Invention

In view of the above problems, an object of one embodiment of the present invention is to provide a semiconductor device having a novel structure. Another object of one embodiment of the present invention is to provide a semiconductor device with reduced power consumption. Another object of one embodiment of the present invention is to provide a detecting device with reduced power consumption.

Note that the description of these objects does not preclude the existence of other objects. One embodiment of the present invention does not have to achieve all these objects. Other objects are apparent from the description of the specification, the drawings, the claims, and the like, and other objects can be derived from the description of the specification, the drawings, the claims, and the like.

Means for Solving the Problems

One embodiment of the present invention is a semiconductor device including a latch circuit composed of a dynamic circuit. The latch circuit includes a first circuit, first to third capacitors, first to third clock input terminals, a signal input terminal, a first output terminal, and a second output terminal. The first circuit has a decoding function. First to third clock signals are sequentially supplied to the first to third clock input terminals. In a period during which an "H" signal is supplied to the first clock signal, the first circuit is supplied with a plurality of input signals through the signal input terminal, and a potential of the first capacitor is updated on the basis of a result of decoding performed by the first circuit. In a period during which the "H" signal is supplied to the second clock signal, a potential of the second capacitor is updated on the basis of the potential of the first capacitor, and the first output terminal is supplied with the potential of the second capacitor as a first output signal. When the "H" signal is supplied to the third clock signal, a potential of the third capacitor is updated on the basis of the potential of the second capacitor, and the second output terminal is supplied with the potential of the third capacitor as a second output signal in the semiconductor device.

In the above structure, the latch circuit includes fourth to sixth clock input terminals. Fourth to sixth clock signals are sequentially supplied to the fourth to sixth clock input terminals. The first capacitor is precharged in a period during which the "H" signal is supplied to the fourth clock signal. The second capacitor is precharged in a period during which the "H" signal is supplied to the fifth clock signal. The third capacitor is precharged in a period during which the "H" signal is supplied to the sixth clock signal.

In the above structure, the latch circuit includes a second circuit. The second circuit generates a seventh clock signal and an eighth clock signal from the second clock signal supplied to the second clock input terminal. The latch circuit has functions of latching a result of decoding the input signal and outputting the latch result to the first output signal in a period during which the "H" signal is supplied to the seventh clock signal. In a period during which the "H" signal is supplied to the eighth clock signal, the second capacitor is precharged by supply of the fifth clock signal to the fifth clock input terminal. A potential of the precharged second capacitor is output as the "H" signal to the first output signal when the first output signal is the "H" signal. The potential of the second capacitor is discharged by the second output signal and the potential of the second capacitor is output as the "L" signal to the first output signal when the first output signal is an "L" signal.

In each of the above structures, a plurality of cascade-connected latch circuits can function as a counter circuit.

In any of the above structures, the latch circuit includes first to fifth transistors. The fourth clock input terminal is electrically connected to a gate of the first transistor. The fifth clock input terminal is electrically connected to a gate of the second transistor. The sixth clock input terminal is electrically connected to a gate of the third transistor. One electrode of the second capacitor is electrically connected to a gate of the fourth transistor. One electrode of the third capacitor is electrically connected to a gate of the fifth transistor. The first to fifth transistors each include a metal oxide in a semiconductor layer. The first to fifth transistors each include a back gate. A potential supplied to the back gates of the first to third transistors is different from a potential supplied to the back gates of the fourth and fifth transistors.

A detecting device includes the semiconductor device described in any of the above structures, a detecting circuit, and a battery. An output signal of the semiconductor device is supplied to the detecting circuit. In the detecting device, the detecting circuit uses the output signal as a monitor cycle for monitoring an output potential of the battery.

Effect of the Invention

One embodiment of the present invention can provide a semiconductor device having a novel structure. One embodiment of the present invention can provide a semiconductor device with reduced power consumption. One embodiment of the present invention can provide a detecting device with reduced power consumption.

Note that the effects of one embodiment of the present invention are not limited to the effects listed above. The effects listed above do not preclude the existence of other effects. Note that the other effects are effects that are not described in this section and will be described below. The effects that are not described in this section will be derived from the description of the specification, the drawings, and the like and can be extracted from the description as appropriate by those skilled in the art. Note that one embodiment of the present invention has at least one of the effects listed above and/or the other effects. Accordingly, depending on the case, one embodiment of the present invention does not have the effects listed above in some cases.

BRIEF DESCRIPTION OF THE DRAWINGS

FIG. 2A is a block diagram illustrating a semiconductor device. FIG. 2B1, FIG. 2B2, and FIG. 2C are circuit diagrams illustrating semiconductor devices.

FIG. 4A1 to FIG. 4A3 and FIG. 4B are circuit diagrams illustrating semiconductor devices.

FIG. 6A1 to FIG. 6A4 are circuit diagrams illustrating semiconductor devices.

FIG. 19A1, FIG. 19A2, and FIG. 19B1 to FIG. 19B4 are diagrams illustrating electronic devices.

MODE FOR CARRYING OUT THE INVENTION

Figure 1A:
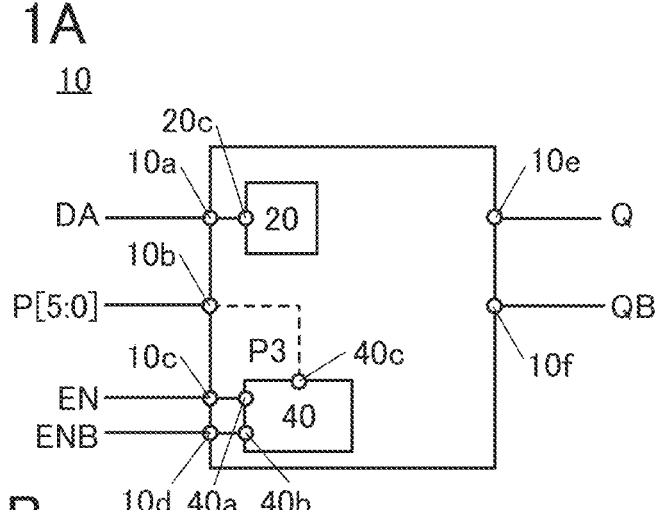
FIG. 1A is a block diagram illustrating a semiconductor device.

Embodiments will be described below with reference to the drawings. Note that the embodiments can be implemented with many different modes, and it will be readily understood by those skilled in the art that modes and details thereof can be changed in various ways without departing from the spirit and scope thereof. Thus, the present invention should not be interpreted as being limited to the description of the embodiments below.

In the drawings, the size, the layer thickness, or the region is exaggerated for clarity in some cases. Therefore, the size, the layer thickness, or the region is not limited to the illustrated scale. The drawings are schematic views showing ideal examples, and embodiments of the present invention are not limited to shapes, values, or the like shown in the drawings.

Furthermore, it is noted that ordinal numbers such as "first", "second", and "third" used in this specification are used in order to avoid confusion among components, and the terms do not limit the components numerically.

In this specification, terms for describing arrangement, such as "over" and "under", are used for convenience in describing a positional relationship between components with reference to drawings. Furthermore, the positional relationship between components is changed as appropriate in accordance with the direction in which each component is described. Thus, without limitation to terms described in this specification, the description can be changed appropriately depending on the situation.

In this specification and the like, a transistor is an element having at least three terminals of a gate, a drain, and a source. The transistor has a channel formation region between the drain (a drain terminal, a drain region, or a drain electrode) and the source (a source terminal, a source region, or a source electrode), and can make current flow between the source and the drain through the channel formation region. Note that in this specification and the like, a channel formation region refers to a region through which current mainly flows.

Furthermore, functions of a source and a drain might be switched when a transistor of opposite polarity is employed or when a direction of current flow is changed in circuit operation, for example. Thus, the terms of source and drain are interchangeably used in this specification and the like.

In this specification and the like, "electrically connected" includes the case where connection is made through an "object having any electric function". Here, there is no particular limitation on the "object having any electric function" as long as electric signals can be transmitted and received between the connected components. Examples of the "object having any electric function" include a switching element such as a transistor, a resistor, an inductor, a capacitor, and other elements with a variety of functions as well as an electrode and a wiring formed of different conductive layers.

In this specification and the like, "parallel" indicates a state where two straight lines are placed at an angle greater than or equal to −10° and less than or equal to 10°. Accordingly, the case where the angle is greater than or equal to −5° and less than or equal to 5° is also included. Moreover, "perpendicular" indicates a state where two straight lines are placed at an angle greater than or equal to 80° and less than or equal to 100°. Accordingly, the case where the angle is greater than or equal to 85° and less than or equal to 95° is also included.

Moreover, in this specification and the like, the term "film" and the term "layer" can be interchanged with each other. For example, the term "conductive layer" can be changed into the term "conductive film" in some cases. Moreover, for example, the term "insulating film" can be changed into the term "insulating layer" in some cases.

Furthermore, unless otherwise specified, off-state current in this specification and the like refers to drain current of a transistor in an off state (also referred to as a non-conducting state or a cutoff state). Unless otherwise specified, the off state of an n-channel transistor refers to a state where the voltage Vgs between its gate and source is lower than the threshold voltage Vth, and the off state of a p-channel transistor refers to a state where the voltage Vgs between its gate and source is higher than the threshold voltage Vth. For example, the off-state current of an n-channel transistor sometimes refers to drain current at the time when the voltage Vgs between its gate and source is lower than the threshold voltage Vth.

The off-state current of a transistor depends on Vgs in some cases. Thus, the off-state current of a transistor being lower than or equal to I sometimes means that there is Vgs at which the off-state current of the transistor becomes lower than or equal to I.

As an example, the assumption is made of an n-channel transistor where the threshold voltage Vth is 0.5 V, and the drain current at Vgs of 0.5 V is $1\times10^{-9}$ A, the drain current at Vgs of 0.1 V is $1\times10^{-13}$ A, the drain current at Vgs of −0.5 V is $1\times10^{-19}$ A, and the drain current at Vgs of −0.8 V is $1\times10^{-22}$ A. The drain current of the transistor is lower than or equal to $1\times10^{-19}$ A at Vgs of −0.5 V or at Vgs in the range of −0.8 V to −0.5 V; therefore, it is sometimes said that the off-state current of the transistor is lower than or equal to $1\times10^{-19}$ A. Since there is Vgs at which the drain current of the transistor is lower than or equal to $1\times10^{-22}$ A, it is sometimes said that the off-state current of the transistor is lower than or equal to $1\times10^{-22}$ A.

In this specification and the like, the off-state current of a transistor having a channel width W is sometimes represented by the value of flowing current per channel width W. Alternatively, it is sometimes represented by the value of flowing current per given channel width (e.g., 1 μm). In the latter case, the off-state current is sometimes represented by the unit with the dimension of current per length (e.g., A/μm).

The off-state current of a transistor depends on temperature in some cases. Unless otherwise specified, the off-state current in this specification sometimes refers to off-state current at room temperature, 60° C., 85° C., 95° C., or 125° C. Alternatively, the off-state current sometimes refers to off-state current at a temperature at which reliability of a semiconductor device or the like including the transistor is ensured or a temperature at which the semiconductor device or the like including the transistor is used (e.g., any temperature in the range of 5° C. to 35° C.). The off-state current of the transistor being lower than or equal to I sometimes means that there is Vgs at which the off-state current of a transistor is lower than or equal to I at room temperature, 60° C., 85° C., 95° C., 125° C., a temperature at which reliability of a semiconductor device or the like including the transistor is ensured, or a temperature at which the semiconductor device or the like including the transistor is used (e.g., any temperature in the range of 5° C. to 35° C.).

The off-state current of a transistor depends on the voltage Vds between its drain and source in some cases. Unless otherwise specified, the off-state current in this specification sometimes refers to off-state current at Vds of 0.1 V, 0.8 V, 1 V, 1.2 V, 1.8 V, 2.5 V, 3 V, 3.3 V, 10 V, 12 V, 16 V, or 20 V. Alternatively, the off-state current sometimes refers to off-state current at Vds at which reliability of a semiconductor device or the like including the transistor is ensured or Vds used in the semiconductor device or the like including the transistor. The off-state current of the transistor being lower than or equal to I sometimes means that there is Vgs at which the off-state current of a transistor is lower than or equal to I at Vds of 0.1 V, 0.8 V, 1 V, 1.2 V, 1.8 V, 2.5 V, 3 V, 3.3 V, 10 V, 12 V, 16 V, or 20 V, at Vds at which reliability of a semiconductor device or the like including the transistor is ensured, or at Vds used in the semiconductor device or the like including the transistor.

In the above description of the off-state current, the drain may be replaced with the source. That is, the off-state current sometimes refers to current that flows through a source of a transistor in an off state.

In this specification and the like, leakage current sometimes expresses the same meaning as off-state current. Furthermore, in this specification and the like, the off-state current sometimes refers to current that flows between a source and a drain of a transistor in an off state, for example.

Note that voltage refers to a difference between potentials of two points, and a potential refers to electrostatic energy (electric potential energy) of a unit charge at a given point in an electrostatic field. In general, a difference between a potential of one point and a reference potential (e.g., a ground potential) is merely called a potential or voltage, and a potential and voltage are used as synonyms in many cases. Therefore, in this specification, a potential may be rephrased as voltage and voltage may be rephrased as a potential unless otherwise specified.

Embodiment 1

In this embodiment, a semiconductor device will be described with reference to FIG. 1 to FIG. 12. The semiconductor device described in this embodiment functions as a latch circuit. A plurality of cascade-connected latch circuits can function as a counter circuit.

The semiconductor device of one embodiment of the present invention will be described. The semiconductor device is composed of a dynamic circuit.

First, the dynamic circuit will be briefly described. The dynamic circuit includes a first transistor, a second transistor, a first circuit, a capacitor, a first wiring, and a second wiring. The first circuit includes a first terminal, a second terminal, and a third terminal.

One of a source and a drain of the first transistor is electrically connected to the first wiring. The other of the source and the drain of the first transistor is electrically connected to one of a source and a drain of the second transistor and one electrode of the capacitor. The other of the source and the drain of the second transistor is electrically connected to the first terminal of the first circuit. The second terminal of the first circuit is electrically connected to the other electrode of the capacitor and the second wiring. The one electrode of the capacitor corresponds to an output terminal.

A power supply voltage of the dynamic circuit is applied to the first wiring, and a reference voltage of the dynamic circuit is applied to the second wiring. The first circuit has a decoding function.

Next, the operation of the dynamic circuit will be briefly described. A first signal is supplied to a gate of the first transistor, whereby the first transistor is turned on. The first signal allows the capacitor to be precharged with the power supply voltage applied to the first wiring through the first transistor. After completion of precharging the capacitor, the first transistor is turned off. Note that the output terminal can treat the state where the capacitor is precharged as an "H" signal. In addition, the output terminal can treat the state where the capacitor is discharged as an "L" signal.

Then, an input signal is supplied to the third terminal included in the first circuit. The input signal may be either one input signal or a plurality of input signals. Note that a plurality of input signals allow more complicated conditions to be set. In the case where the conditions set to the first circuit correspond to the conditions of the supplied input signal, electrical continuity is established between the first terminal and the second terminal of the first circuit. In the following description, the electrical continuity established between the first terminal and the second terminal of the first circuit means the on state of the first circuit.

Next, a second signal is supplied to a gate of the second transistor, whereby the second transistor is turned on. When the first circuit is in the on state, the potential retained in the capacitor is discharged through the second transistor and the first circuit.

In the case where the conditions set to the first circuit correspond to the conditions of the supplied input signal, the output terminal outputs the "L" signal.

The semiconductor device functioning as a latch circuit in this embodiment will be described. The latch circuit includes a first circuit, first to third capacitors, first to sixth clock input terminals, a signal input terminal, a first output terminal, and a second output terminal. The first circuit has a decoding function.

First to sixth clock signals are sequentially supplied to the first to sixth clock input terminals. In a period during which the "H" signal is supplied to the first clock signal, a precharge potential is supplied to the first capacitor. In a period during which the "H" signal is supplied to the second clock signal, the potential of the first capacitor is updated on the basis of the results of decoding performed by the first circuit.

In a period during which the "H" signal is supplied to the third clock signal, the precharge potential is supplied to the second capacitor. In a period during which the "H" signal is supplied to the fourth clock signal, the potential of the second capacitor is updated by a change in the potential of the first capacitor, and the potential of the second capacitor is supplied as a first output signal to the first output terminal.

In a period during which the "H" signal is supplied to the fifth clock signal, the precharge potential is supplied to the third capacitor. In a period during which the "H" signal is supplied to the sixth clock signal, the potential of the third capacitor is updated by a change in the potential of the second capacitor, and the potential of the third capacitor is supplied as a second output signal to the second output terminal in the semiconductor device.

The latch circuit further includes a second circuit. The second circuit generates a seventh clock signal and an eighth clock signal from the third clock signal supplied to the third clock input terminal.

In a period during which the "H" signal is supplied to the seventh clock signal, the latch circuit has a function of latching the results of decoding the input signal and outputting the latch results to the first output signal.

In a period during which the "H" signal is supplied to the eighth clock signal, the fifth clock signal is supplied to the fifth clock input terminal and thus the second capacitor is precharged. When the first output signal is the "H" signal, the potential of the precharged second capacitor is output as the "H" signal to the first output signal. When the first output signal is the "L" signal, the potential of the second capacitor is discharged by the second output signal, and the potential of the second capacitor is output as the "L" signal to the first output signal.

Here, the details of the latch circuit will be described. The latch circuit includes first to seventh transistors. The first clock input terminal is electrically connected to a gate of the first transistor. The third clock input terminal is electrically connected to a gate of the second transistor. The fourth clock input terminal is electrically connected to a gate of the third transistor. The fifth clock input terminal is electrically connected to a gate of the fifth transistor. The sixth clock input terminal is electrically connected to a gate of the sixth transistor. Note that the second clock input terminal is electrically connected to the first circuit.

A first wiring is electrically connected to one of a source and a drain of the first transistor, one of a source and a drain of the third transistor, and one of a source and a drain of the fifth transistor. The other of the source and the drain of the first transistor is electrically connected to the first terminal of the first circuit, a gate of the fourth transistor, and one electrode of the first capacitor. The other of the source and the drain of the second transistor is electrically connected to the one of the source and the drain of the third transistor, a gate of the seventh transistor, and one electrode of the second capacitor. The other of the source and the drain of the third transistor is electrically connected to one of a source and a drain of the fourth transistor. The other of the source and the drain of the fifth transistor is electrically connected to one of a source and a drain of the sixth transistor and one electrode of the third capacitor. The other of the source and the drain of the sixth transistor is electrically connected to one of a source and a drain of the seventh transistor. A second wiring is electrically connected to the second terminal of the first circuit, the other of the source and the drain of the fourth transistor, the other of the source and the drain of the seventh transistor, the other electrode of the first capacitor, the other electrode of the second capacitor, and the other electrode of the third capacitor.

The first to seventh transistors each include a metal oxide in a semiconductor layer. In addition, the first to seventh transistors each include a back gate. Note that a potential supplied to the back gates of the first, third, and fifth transistors is different from that supplied to the back gates of the third, fourth, sixth, and seventh transistors.

For example, the back gates of the first, second, and fifth transistors are supplied with a lower potential than the back gates of the third, fourth, sixth, and seventh transistors. When the potential supplied to the back gates of the first, second, and fifth transistors is low, the on-state current of the first, second, and fifth transistors can be increased. An increase in the on-state current of the first, second, and fifth transistors results in higher speed of charging the first to third capacitors.

Note that the one electrode of the second capacitor is connected to the first output terminal; thus, the driving capability in the case where the "H" signal is output to the first output terminal can be improved. Similarly, the one electrode of the third capacitor is connected to the second output terminal; thus, the driving capability in the case where the "H" signal is output to the second output terminal can be improved.

The back gates of the third, fourth, sixth, and seventh transistors are supplied with a higher potential than the back gates of the first, second, and fifth transistors. When the potential supplied to the back gates of the third, fourth, sixth, and seventh transistors is high, the on-state current of the third, fourth, sixth, and seventh transistors is reduced.

For example, a reduction in the off-state current of the third and fourth transistors reduces leakage current from the second capacitor through the third and fourth transistors. Similarly, a reduction in the off-state current of the sixth and seventh transistors reduces leakage current from the third capacitor through the sixth and seventh transistors.

A plurality of cascade-connected latch circuits can function as a counter circuit, for example. The counter circuit can be a ternary counter circuit, a senary counter circuit, or a decade counter circuit depending on the number of cascade-connected latch circuits and decoding conditions. The use of a ternary counter circuit, a senary counter circuit, or a decade counter circuit in an electronic device such as a watch can reduce power consumption, for example.

For another application example, a battery monitor device can be achieved using the counter circuit, a detecting circuit, and a battery. An output signal of the counter circuit is supplied to the detecting circuit, for example. The detecting circuit can use the output signal of the counter circuit as a monitor cycle for monitoring an output potential of the battery.

Next, the semiconductor device described in this embodiment will be described with reference to drawings. FIG. 1A is a block diagram illustrating a latch circuit 10. The latch circuit 10 includes a circuit 20, a circuit 40, a signal input terminal 10a, a clock input terminal 10b, a terminal 10c, a terminal 10d, an output terminal 10e, and an output terminal 10f.

An input signal is supplied to the signal input terminal 10a. Note that one or more input signals may be supplied. A clock signal is supplied to the clock input terminal 10b. A plurality of clock signals are preferably supplied. An example is shown in which clock signals P0 to P5 are supplied to the latch circuit described in this embodiment. A signal EN is supplied to the terminal 10c, and a signal ENB is supplied to the terminal 10d. The signal ENB is an inverted signal of the signal EN. The output terminal 10e outputs an output signal Q, and the output terminal 10f outputs an output signal QB. The output signal QB is an inverted signal of the output signal Q.

Although the details will be described with reference to FIG. 1B, the circuit 20 includes terminals (20a, 20b, and 20c). An input signal DA is supplied to the terminal 20c through the signal input terminal 10a. Note that the circuit 20 has a decoding function.

The circuit 40 includes terminals (40a, 40b, 40c, 40d, and 40e). The signal EN is supplied to the terminal 40a through the terminal 10c. The signal ENB is supplied to the terminal 40b through the terminal 10d. The clock signal P3 is supplied to the terminal 40c through the clock input terminal 10b. The circuit 40 can generate a clock signal P3I and a clock signal P3R from the clock signal P3.

Figure 1B:
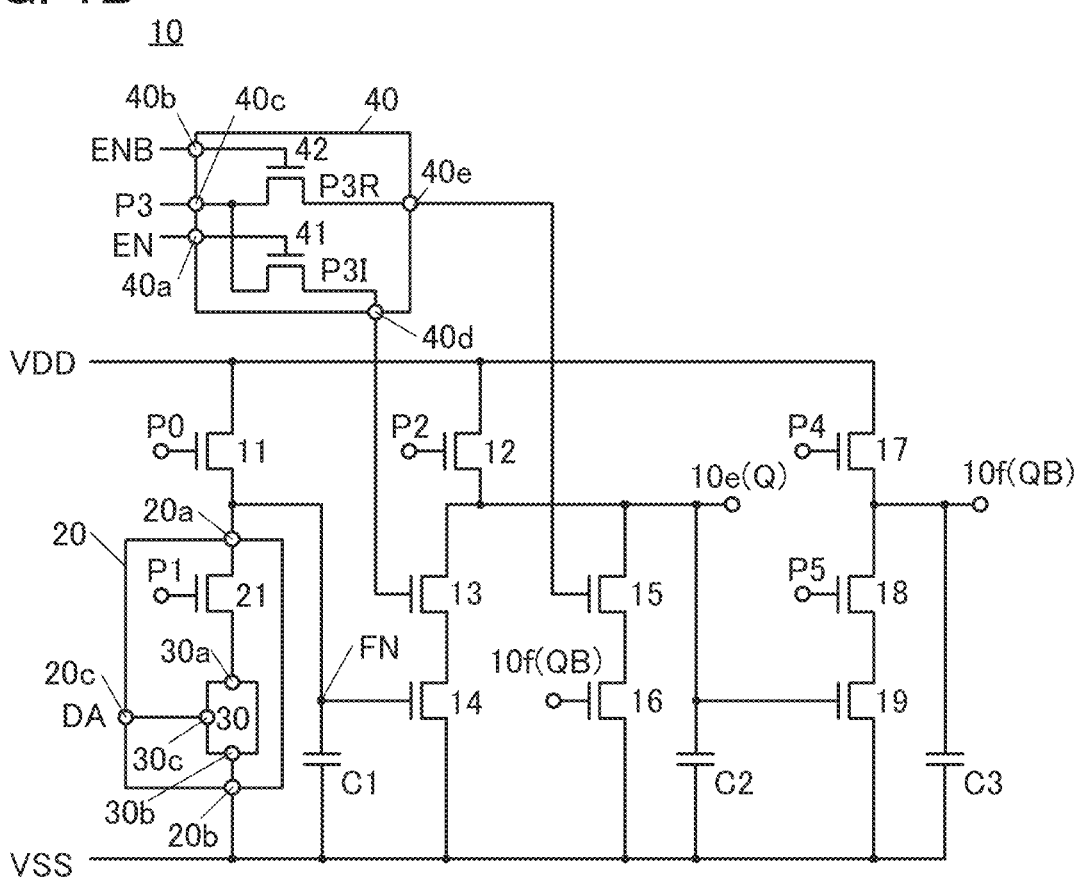
FIG. 1B is a circuit diagram illustrating a semiconductor device.

FIG. 1B is a circuit diagram illustrating the latch circuit 10 in detail. The latch circuit 10 includes transistors 11 to 19, capacitors C1 to C3, the circuit 20, and the circuit 40. The circuit 20 includes a transistor 21 and a circuit 30. The circuit 30 includes terminals 30a to 30c. The circuit 40 includes a transistor 41 and a transistor 42. Note that the latch circuit 10 includes a wiring VDD and a wiring VSS.

The clock signal P0 is supplied to a gate of the transistor 11. The clock signal P1 is supplied to a gate of the transistor 21. The clock signal P2 is supplied to a gate of the transistor 12. The clock signal P3I is supplied to a gate of the transistor 13. The clock signal P3R is supplied to a gate of the transistor 15. The clock signal P4 is supplied to a gate of the transistor 17. The clock signal P5 is supplied to a gate of the transistor 18.

The wiring VDD is electrically connected to one of a source and a drain of the transistor 11, one of a source and a drain of the transistor 12, and one of a source and a drain of the transistor 17. The other of the source and the drain of the transistor 11 is electrically connected to the terminal 20*a* of the circuit 20, a gate of the transistor 14, and one electrode of the capacitor C1. One of a source and a drain of the transistor 14 is electrically connected to one of a source and a drain of the transistor 13. The other of the source and the drain of the transistor 13 is electrically connected to the other of the source and the drain of the transistor 12, one of a source and a drain of the transistor 15, one electrode of the capacitor C2, a gate of the transistor 19, and the output terminal 10*e*. The other of the source and the drain of the transistor 15 is electrically connected to one of a source and a drain of the transistor 16. The other of the source and the drain of the transistor 17 is electrically connected to one of a source and a drain of the transistor 18, one electrode of the capacitor C3, and the output terminal 10*f*. The other of the source and the drain of the transistor 18 is electrically connected to one of a source and a drain of the transistor 19. The wiring VSS is electrically connected to the terminal 20*b* of the circuit 20, the other of the source and the drain of the transistor 14, the other of the source and the drain of the transistor 16, the other of the source and the drain of the transistor 19, the other electrode of the capacitor C1, the other electrode of the capacitor C2, and the other electrode of the capacitor C3. Note that a node FN is formed by connection between the other of the source and the drain of the transistor 11, the terminal 20*a* of the circuit 20, the gate of the transistor 14, and the one electrode of the capacitor C1.

The terminal 40*a* is electrically connected to a gate of the transistor 41. The terminal 40*b* is electrically connected to a gate of the transistor 42. The terminal 40*c* is electrically connected to one of a source and a drain of the transistor 41 and one of a source and a drain of the transistor 42. The other of the source and the drain of the transistor 41 is electrically connected to the gate of the transistor 13 through the terminal 40*d*. The other of the source and the drain of the transistor 42 is electrically connected to the gate of the transistor 15 through the terminal 40*e*. The output terminal 10*f* is electrically connected to a gate of the transistor 16.

The terminal 20*a* included in the circuit 20 is electrically connected to one of a source and a drain of the transistor 21. The other of the source and the drain of the transistor 21 is electrically connected to the terminal 30*a* included in the circuit 30.

Next, the operation of the latch circuit 10 will be described. First, the case is described where the "H" signal is supplied to the signal EN, the transistor 41 is in the on state, the "L" signal is supplied to the signal ENB, and the transistor 42 is in the off state. In the case of the above conditions, the "L" signal is supplied to the clock signal P3I and the clock signal P3R until the clock signal P3 is supplied.

The transistor 11 is turned on by a signal supplied to the clock signal P0. The capacitor C1 is precharged, through the transistor 11, with a first potential supplied to the wiring VDD to be the "H" signal.

Then, in a period during which the "H" signal is supplied to the clock signal P1, a plurality of input signals DA are supplied to the circuit 30 through the signal input terminal, and the potential of the capacitor C1 is updated on the basis of the results of decoding performed by the circuit 20.

More specifically, in the case where the contents of the input signals DA correspond to the decoding results, the circuit 30 is turned on and electrical continuity is established between the terminal 30*a* and the terminal 30*b*. The potential of the capacitor C1 is discharged through the transistor 21 and the circuit 30. In the case where the contents of the input signals DA do not correspond to the decoding results, the circuit 30 is turned off and electrical continuity is not established between the terminal 30*a* and the terminal 30*b*. Thus, the potential of the capacitor C1 keeps being the first potential.

Next, the transistor 12 is turned on by a signal supplied to the clock signal P2. The capacitor C2 is precharged, through the transistor 12, with a potential supplied to the wiring VDD to be the "H" signal.

Next, in a period during which the "H" signal is supplied to the clock signal P3, the "H" signal is supplied to the clock signal P3I and the "L" signal is supplied to the clock signal P3R. The potential of the capacitor C2 is updated on the basis of the potential of the capacitor C1, and the potential of the capacitor C2 is supplied as the output signal Q to the output terminal 10*e*.

More specifically, when the potential of the capacitor C1 is the "H" signal, the transistor 14 is turned on. In addition, when the clock signal P3I is the "H" signal, the transistor 13 is turned on. The potential of the capacitor C2 is discharged through the transistor 13 and the transistor 14. Thus, the output terminal 10*e* outputs the "L" signal. For another example, when the potential of the capacitor C1 is the "L" signal, the transistor 14 is turned off. Thus, the potential of the capacitor C2 keeps being the "H" signal.

Next, the transistor 17 is turned on by a signal supplied to the clock signal P4. The capacitor C3 is precharged, through the transistor 17, with the potential supplied to the wiring VDD to be the "H" signal.

Next, in a period during which the "H" signal is supplied to the clock signal P5, the potential of the capacitor C3 is updated on the basis of the potential of the capacitor C2. The potential of the capacitor C3 is supplied as the output signal QB to the output terminal 10*f*.

More specifically, when the potential of the capacitor C2 is the "H" signal, the transistor 19 is turned on. In addition, when the clock signal P5 is the "H" signal, the transistor 18 is turned on. The potential of the capacitor C3 is discharged through the transistor 18 and the transistor 19. Thus, the output terminal 10*f* outputs the "L" signal. For another example, when the potential of the capacitor C2 is the "L" signal, the transistor 19 is turned off. Thus, the potential of the capacitor C3 keeps being the first potential.

Next, the case is described where the "H" signal is supplied to the clock signal P3R and the "L" signal is supplied to the clock signal P3I. When the clock signal P3I is the "L" signal, the transistor 13 is turned off. Thus, the input signals DA do not affect the output signal Q or the output signal QB.

Description is made on a period after supply of the "H" signal to the clock signal P3R and supply of the "L" signal to the clock signal P3I in the period during which the "H" signal is supplied to the clock signal P3. Note that the capacitor C2 is precharged, through the transistor 12, with the potential supplied to the wiring VDD to retain the "H" signal.

When the output signal QB is the "L" signal, the transistor 16 is turned off. Thus, the potential of the precharged capacitor C2 keeps being the "H" signal. Thus, the "H" signal is output to the output signal Q.

When the output signal QB is the "H" signal, the transistor 16 is turned on. Thus, the potential of the capacitor C2 is discharged through the transistor 15 and the transistor 16. The potential of the capacitor C2 is output as the "L" signal to the output signal Q.

The latch circuit 10 can control, with the use of different clock signals, the first transistor that precharges the capacitor and the second transistor that discharges the capacitor, for example. That is, the latch circuit 10 described in this embodiment can reduce shoot-through current of the first transistor and the second transistor, resulting in lower power consumption. Note that the first transistor corresponds to the transistor 11, the transistor 12, and the transistor 17 in the latch circuit 10, and the second transistor corresponds to the transistor 13, the transistor 14, the transistor 15, the transistor 16, the transistor 18, and the transistor 19 in the latch circuit 10.

In addition, the output signal Q or the output signal QB is refreshed in a period during which the "H" signal is supplied to the signal ENB and the "L" signal is supplied to the signal EN; thus, the latch circuit 10 can reduce signal deterioration.

Note that the transistors used in the latch circuit 10 each preferably include a metal oxide in a semiconductor layer. A transistor including a metal oxide in a semiconductor layer is suitable for a circuit that operates at low speed because the off-state current of the transistor in the off state is low. Note that the circuit that operates at low speed preferably has a clock frequency lower than 50 kHz. Alternatively, the clock frequency is preferably lower than 1 kHz. Alternatively, the clock frequency is further preferably lower than 100 Hz. Note that a transistor including a metal oxide in a semiconductor layer is referred to as an OS transistor. The OS transistor will be described in detail in Embodiment 4.

A counter circuit using a latch circuit will be described with reference to FIG. 2A. Note that in the following description of drawings, differences from the latch circuit 10 will be described, and description of the components denoted by the same reference numerals as those in FIG. 1A or FIG. 1B may be omitted.

FIG. 2A is a block diagram illustrating a ternary counter circuit 60. The ternary counter circuit 60 includes a latch circuit 10A, a latch circuit 10B, and a circuit 10CA. Differences from the latch circuit 10 in FIG. 1 are as follows: the latch circuit 10A includes a circuit 20A and the latch circuit 10B includes a circuit 20B. Furthermore, the latch circuit 10A and the latch circuit 10B operate in synchronization with each other; thus, one circuit 40 is provided for the latch circuit 10A and the latch circuit 10B.

Here, the ternary counter circuit 60 will be described in detail. An input signal DAa is supplied to the terminal 20c of the circuit 20A through the signal input terminal 10a of the latch circuit 10A. An input signal DAb is supplied to the terminal 20c of the circuit 20B through the signal input terminal 10a of the latch circuit 10B. Note that one of the output signals Q[1:0] and the output signals QB[1:0] or the plurality of output signals are supplied to the input signal DAa or the input signal DAb. The clock signals P0 to P5 are supplied to the clock input terminals 10b of the latch circuit 10A and the latch circuit 10B. The circuit 40 can supply the clock signal P3I to the terminals 10c of the latch circuit 10A and the latch circuit 10B. In addition, the circuit 40 can supply the clock signal P3R to the terminals 10d of the latch circuit 10A and the latch circuit 10B.

Here, the circuit 10CA will be described. The circuit 10CA includes a terminal 10c1, a terminal 10c2, a terminal 10c3, and a terminal 10c4. The output signals Q[1:0] are supplied to the terminal 10c1 of the circuit 10CA from the latch circuit 10A and the latch circuit 10B. The output signals QB[1:0] are supplied to the terminal 10c2 of the circuit 10CA from the latch circuit 10A and the latch circuit 10B. The circuit 10CA can output a carry signal CA3 and a carry signal CA3B of the ternary counter circuit to the terminal 10c3 and the terminal 10c4, respectively. Note that the carry signal CA3B is an inverted signal of the carry signal CA3.

FIG. 2B1 is a circuit diagram illustrating the circuit 20A. The circuit 20A includes the transistor 21 and a circuit 30A. The circuit 30A includes a transistor 31, a transistor 32, the terminal 30a, the terminal 30b, and the terminal 30c. Note that the terminal 30c is not shown in FIG. 2B1; alternatively, a matching condition for decoding the input signal DAa, which is supplied to gates of the transistors included in the circuit 30A, is shown. The details of the matching condition for decoding the input signal DAa will be described later.

The terminal 20a of the circuit 20A is electrically connected to one of the source and the drain of the transistor 21. The other of the source and the drain of the transistor 21 is electrically connected to one of a source and a drain of the transistor 31 through the terminal 30a. The other of the source and the drain of the transistor 31 is electrically connected to one of a source and a drain of the transistor 32. The other of the source and the drain of the transistor 32 is electrically connected to the terminal 20b through the terminal 30b. The gate of the transistor 31 is supplied with an output signal QB0. The gate of the transistor 32 is supplied with an output signal QB1.

FIG. 2B2 is a circuit diagram illustrating the circuit 20B. The circuit 20B includes the transistor 21 and a circuit 30B. The circuit 30B includes a transistor 33, the terminal 30a, the terminal 30b, and the terminal 30c. Note that the terminal 30c is not shown in FIG. 2B2; alternatively, a matching condition for decoding the input signal DAb, which is supplied to a gate of the transistor included in the circuit 30B, is shown. The details of the matching condition for decoding the input signal DAb will be described later.

The terminal 20a of the circuit 20B is electrically connected to one of the source and the drain of the transistor 21. The other of the source and the drain of the transistor 21 is electrically connected to one of a source and a drain of the transistor 33 through the terminal 30a. The other of the source and the drain of the transistor 33 is electrically connected to the terminal 20b through the terminal 30b. A gate of the transistor 33 is supplied with an output signal Q0.

Here, the matching conditions where the circuit 30A and the circuit 30A perform decoding will be described. The matching conditions where the circuit 30A and the circuit 30A perform decoding are easily extracted using the Karnaugh map. When the input signal DAa is represented by the logical product as in Formula 1, the latch circuit 10A can operate as a ternary counter.

(Formula 1)

$$DAa = QB0 \cdot QB1 \tag{1}$$

The input signal DAb of the latch circuit 10B can be expressed by Formula 2.

(Formula 2)

$$DAb = Q0 \tag{2}$$

Next, FIG. 2C is a circuit explaining the circuit 10CA. The circuit 10CA includes a transistor 61 to a transistor 66, a transistor 61a, a transistor 62a, a capacitor C4, a capacitor C5, the terminal 10c1, the terminal 10c2, the terminal 10c3, and the terminal 10c4. Note that the terminal 10c1 and the terminal 10c2 are not shown in FIG. 2C; alternatively, a matching condition for decoding the output signals Q[1:0] or the output signals QB[1:0], which is supplied to gates of the transistors included in the circuit 10CA, is shown. The details of the matching condition for decoding the output signals Q[1:0] or the output signals QB[1:0] will be described later.

The clock signal P0 is supplied to a gate of the transistor 61 and a gate of the transistor 61a. The clock signal P1 is supplied to a gate of the transistor 62 and a gate of the transistor 62a. The wiring VDD is electrically connected to one of a source and a drain of the transistor 61 and one of a source and a drain of the transistor 61a.

The other of the source and the drain of the transistor 61 is electrically connected to one of a source and a drain of the transistor 62, one electrode of the capacitor C4, and the terminal 10c3. The other of the source and the drain of the transistor 62 is electrically connected to one of a source and a drain of the transistor 63. The other of the source and the drain of the transistor 63 is electrically connected to one of a source and a drain of the transistor 64. The other of the source and the drain of the transistor 64 is electrically connected to the wiring VSS. The other electrode of the capacitor C4 is electrically connected to the wiring VSS.

The other of the source and the drain of the transistor 61a is electrically connected to one of a source and a drain of the transistor 62a, one electrode of the capacitor C5, and the terminal 10c4. The other of the source and the drain of the transistor 62a is electrically connected to one of a source and a drain of a transistor 65 and one of a source and a drain of a transistor 66. The wiring VSS is electrically connected to the other of the source and the drain of the transistor 65 and the other of the source and the drain of the transistor 66. The other electrode of the capacitor C4 is electrically connected to the wiring VSS.

Here, the matching condition where the circuit 10CA performs decoding will be described. A gate of the transistor 63 is supplied with the output signal QB0. A gate of the transistor 64 is supplied with the output signal Q1. A gate of the transistor 65 is supplied with the output signal Q0. A gate of the transistor 66 is supplied with the output signal QB1.

The circuit 10CA can set the matching condition for decoding the output signals Q[1:0] and the matching condition for decoding the output signals QB[1:0]. The matching condition for decoding the output signals Q[1:0] is created with a logical formula CA3_1. The matching condition for decoding the output signals QB[1:0] is created with a logical formula CA3B_1. When the logical formula CA3_1 can be represented by the logical product as in Formula 3, the ternary counter circuit 60 operates.

(Formula 3)

$$CA3\_1 = QB0 \cdot Q1 \quad (3)$$

The logical formula CA3B_1 can be represented by the logical sum as in Formula 4.

(Formula 4)

$$CA3B\_1 = Q0 + QB1 \quad (4)$$

Figure 3:
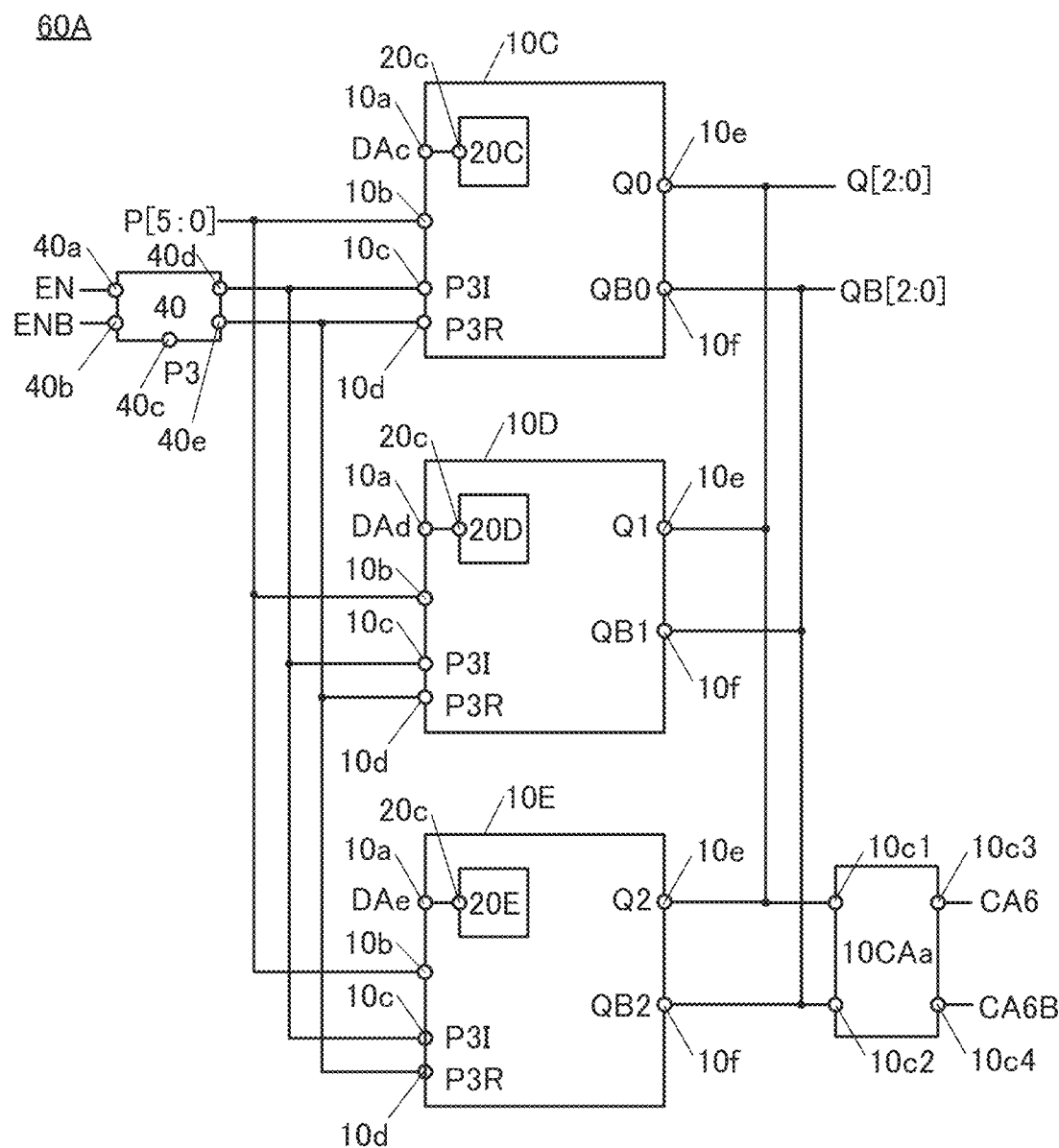
FIG. 3 is a block diagram illustrating a semiconductor device.

FIG. 3 is a block diagram illustrating a senary counter circuit 60A. The senary counter circuit 60A includes a latch circuit 10C, a latch circuit 10D, a latch circuit 10E, and a circuit 10CAa. The latch circuit 10C includes a circuit 20C, the latch circuit 10D includes a circuit 20D, and the latch circuit 10E includes a circuit 20E. The latch circuit 10C, the latch circuit 10D, and the latch circuit 10E operate in synchronization with one another.

Here, the senary counter circuit 60A will be described in detail. An input signal DAc is supplied to the terminal 20c of the circuit 20C through the signal input terminal 10a of the latch circuit 10C. An input signal DAd is supplied to the terminal 20c of the circuit 20D through the signal input terminal 10a of the latch circuit 10D. An input signal DAe is supplied to the terminal 20c of the circuit 20E through the signal input terminal 10a of the latch circuit 10E. Note that one of the output signals Q[2:0] and the output signals QB[2:0] or the plurality of output signals are supplied to the input signal DAc, the input signal DAd, or the input signal DAe. The clock signals P0 to P5 are supplied to the clock input terminals 10b of the latch circuit 10C, the latch circuit 10D, and the latch circuit 10E. The circuit 40 can supply the clock signal P3I to the terminals 10c of the latch circuit 10C, the latch circuit 10D, and the latch circuit 10E. In addition, the circuit 40 can supply the clock signal P3R to the terminals 10d of the latch circuit 10C, the latch circuit 10D, and the latch circuit 10E.

Here, the circuit 10CAa will be described. The circuit 10CAa includes the terminal 10c1, the terminal 10c2, the terminal 10c3, and the terminal 10c4. The output signals Q[2:0] are supplied to the terminal 10c1 of the circuit 10CAa from the latch circuit 10C, the latch circuit 10D, and the latch circuit 10E. The output signals QB[2:0] are supplied to the terminal 10c2 of the circuit 10CAa from the latch circuit 10C, the latch circuit 10D, and the latch circuit 10E. The circuit 10CAa can output a carry signal CA6 and a carry signal CA6B of the senary counter circuit to the terminal 10c3 and the terminal 10c4, respectively.

Next, FIG. 4A1 is a circuit diagram illustrating the circuit 20C. The circuit 20C includes the transistor 21 and a circuit 30C. The circuit 30C is composed of the same components as those of the circuit 30B. Thus, the circuit 30C includes the transistor 33, the terminal 30a, the terminal 30b, and the terminal 30c. Note that the terminal 30c is not shown in FIG. 4A1; alternatively, a matching condition for decoding the input signal DAc, which is supplied to the gate of the transistor included in the circuit 30C, is shown. The matching condition for decoding the input signal DAc is different from the input signal DAc. The gate of the transistor 33 is supplied with the output signal QB0.

Next, FIG. 4A2 is a circuit diagram illustrating the circuit 20D. The circuit 20D includes the transistor 21 and a circuit 30D. The circuit 30D is different from the circuit 30C in including a transistor 34 to a transistor 38.

The matching condition for decoding the input signal DAd will be described. A gate of the transistor 34 is supplied with the output signal QB0. A gate of the transistor 35 is supplied with the output signal Q1. A gate of the transistor 36 is supplied with the output signal Q0. A gate of the transistor 37 is supplied with the output signal QB1. A gate of the transistor 38 is supplied with the output signal QB2.

The terminal 30a of the circuit 30D is electrically connected to one of a source and a drain of the transistor 34 and one of a source and a drain of the transistor 36. The other of the source and the drain of the transistor 34 is electrically connected to one of a source and a drain of the transistor 35. The other of the source and the drain of the transistor 36 is electrically connected to one of a source and a drain of the transistor 37. The other of the source and the drain of the transistor 37 is electrically connected to one of a source and a drain of the transistor 38. The terminal 30b of the circuit 30D is electrically connected to the other of the source and the drain of the transistor 35 and the other of the source and the drain of the transistor 38.

Next, FIG. 4A3 is a circuit diagram illustrating the circuit 20E. The circuit 20E includes the transistor 21 and a circuit 30E. The circuit 30E is different from the circuit 30C in including a transistor 39 and a transistor 3A to a transistor 3C.

The matching condition for decoding the input signal DAe will be described. A gate of the transistor 39 is supplied with the output signal QB0. A gate of the transistor 3A is supplied with the output signal Q2. A gate of the transistor 3B is supplied with the output signal Q0. A gate of the transistor 3C is supplied with the output signal Q1.

The terminal 33a of the circuit 30E is electrically connected to one of a source and a drain of the transistor 39 and one of a source and a drain of the transistor 3B. The other of the source and the drain of the transistor 39 is electrically connected to one of a source and a drain of the transistor 3A. The other of the source and the drain of the transistor 3B is electrically connected to one of a source and a drain of the transistor 3C. The terminal 30b of the circuit 30E is electrically connected to the other of the source and the drain of the transistor 3A and the other of the source and the drain of the transistor 3B.

When the input signal DAc of the latch circuit 10C can be expressed by Formula 5, the senary counter circuit 60A operates.

(Formula 5)

$$DAc = QB0 \quad (5)$$

The input signal DAd of the latch circuit 10D can be represented by the logical sum of the logical product of the first term and the logical product of the second term as in Formula 6.

(Formula 6)

$$DAd = QB0 \cdot Q1 + Q0 \cdot QB1 \cdot QB2 \quad (6)$$

The input signal DAe of the latch circuit 10E can be represented by the logical sum of the logical product of the first term and the logical product of the second term as in Formula 7.

(Formula 7)

$$DAe = QB0 \cdot Q2 + Q0 \cdot Q1 \quad (7)$$

Next, FIG. 4B is a circuit explaining the circuit 10CAa. The circuit 10CAa is composed of the same components as those of the circuit 10CA. Thus, the circuit 10CAa includes the transistor 61 to the transistor 66, the transistor 61a, the transistor 62a, the capacitor C4, the capacitor C5, the terminal 10c1, the terminal 10c2, the terminal 10c3, and the terminal 10c4. Note that the terminal 10c1 and the terminal 10c2 are not shown in FIG. 4B; alternatively, a matching condition for decoding the output signals Q[2:0] or the output signals QB[2:0], which is supplied to the gates of the transistors included in the circuit 10CAa, is shown. Note that for the description of the circuit of the circuit 10CAa, reference can be made to the description of the circuit 10CA in FIG. 2C.

Here, the matching condition where the circuit 10CAa performs decoding will be described. The gate of the transistor 63 is supplied with the output signal Q0. The gate of the transistor 64 is supplied with the output signal Q2. The gate of the transistor 65 is supplied with the output signal QB0. The gate of the transistor 66 is supplied with the output signal QB2.

The circuit 10CAa can set the matching condition for decoding the output signals Q[2:0] and the matching condition for decoding the output signals QB[2:0]. The matching condition for decoding the output signals Q[2:0] is created with a logical formula CA6_1. The matching condition for decoding the output signals QB[2:0] is created with a logical formula CA6B_1. When the logical formula CA6_1 can be represented by the logical product as in Formula 8, the senary counter circuit 60A operates.

(Formula 8)

$$CA6\_1 = Q0 \cdot Q2 \quad (8)$$

The logical formula CA6B_1 can be represented by the logical sum as in Formula 9.

(Formula 9)

$$CA6B\_1 = QB0 + QB2 \quad (9)$$

Figure 5:
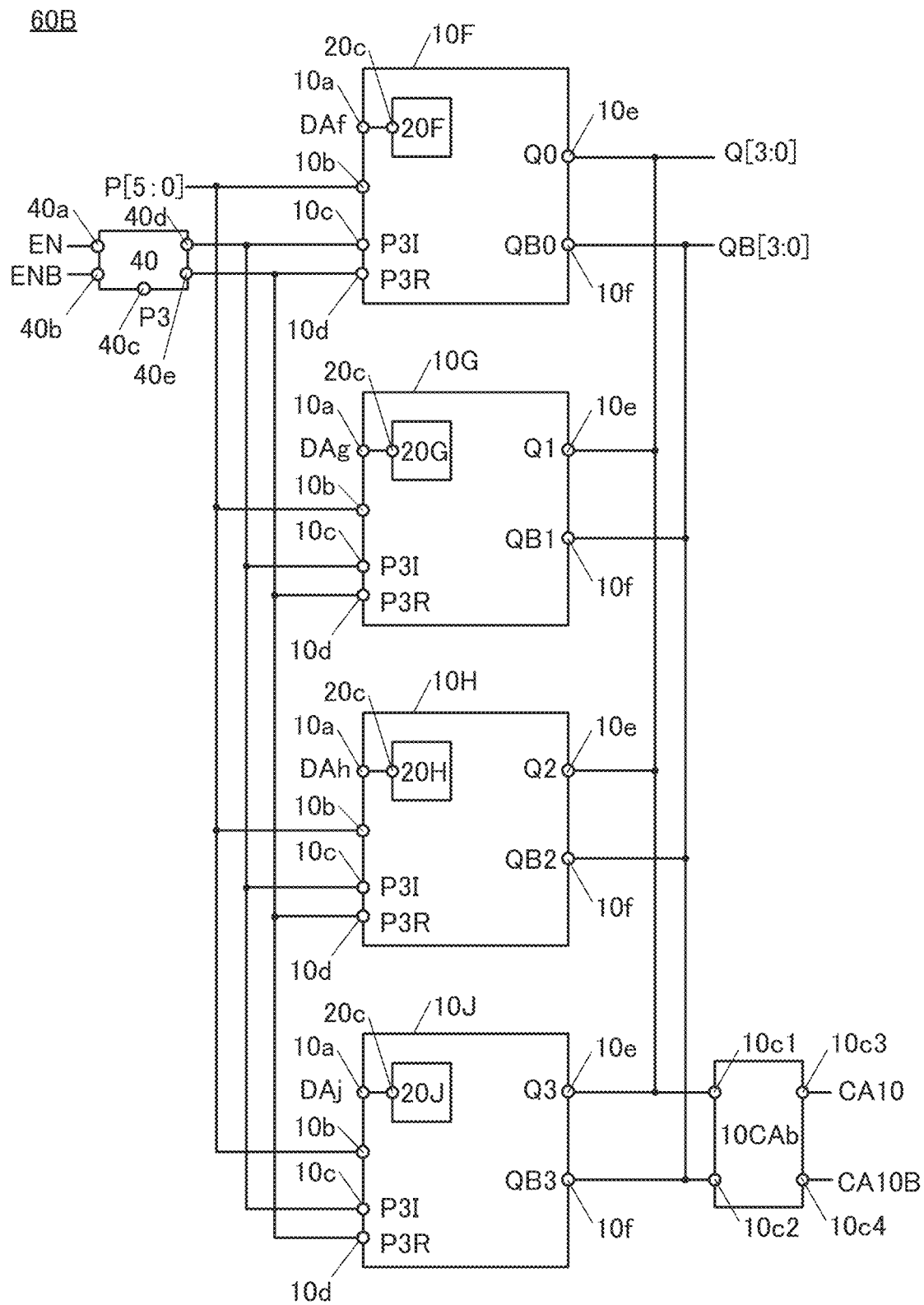
FIG. 5 is a block diagram illustrating a semiconductor device.

FIG. 5 is a block diagram illustrating a decade counter circuit 60B. FIG. 5 includes a latch circuit 10F, a latch circuit 10G, a latch circuit 10H, a latch circuit 10J, and a circuit 10CAb. The latch circuit 10F includes a circuit 20F, the latch circuit 10G includes a circuit 20G, the latch circuit 10H includes a circuit 20H, and the latch circuit 10J includes a circuit 20J. The latch circuit 10F, the latch circuit 10G, the latch circuit 10H, and the latch circuit 10J operate in synchronization with one another.

Here, the decade counter circuit 60B will be described in detail. An input signal DAf is supplied to the terminal 20c of the circuit 20F through the signal input terminal 10a of the latch circuit 10F. An input signal DAg is supplied to the terminal 20c of the circuit 20G through the signal input terminal 10a of the latch circuit 10G. An input signal DAh is supplied to the terminal 20c of the circuit 20H through the signal input terminal 10a of the latch circuit 10H. An input signal DAj is supplied to the terminal 20c of the circuit 20J through the signal input terminal 10a of the latch circuit 10J. Note that output signals Q[3:0] and output signals QB[3:0] are supplied to the input signal DAf, the input signal DAg, the input signal DAh, or the input signal DAj. The clock signals P0 to P5 are supplied to the clock input terminals 10b of the latch circuit 10F, the latch circuit 10G, the latch circuit 10H, and the latch circuit 10J. The circuit 40 can supply the clock signal P3I to the terminals 10c of the latch circuit 10F, the latch circuit 10G, the latch circuit 10H, and the latch circuit 10J. The circuit 40 can supply the clock signal P3R to the terminals 10d of the latch circuit 10F, the latch circuit 10G, the latch circuit 10H, and the latch circuit 10J.

Here, the circuit 10CAb will be described. The circuit 10CAb includes the terminal 10c1, the terminal 10c2, the terminal 10c3, and the terminal 10c4. The output signals Q[3:0] are supplied to the terminal 10c1 of the circuit 10CAb from the latch circuit 10F, the latch circuit 10G, the latch circuit 10H, and the latch circuit 10J. The output signals QB[3:0] are supplied to the terminal 10c2 of the circuit 10CAb from the latch circuit 10F, the latch circuit 10G, the latch circuit 10H, and the latch circuit 10J. The circuit 10CAb can output a carry signal CA10 and a carry signal CA10B of the decade counter circuit 60B to the terminal 10c3 and the terminal 10c4, respectively.

Next, FIG. 6A1 is a circuit diagram illustrating the circuit 20F. The circuit 20F includes the transistor 21 and a circuit 30F. The circuit 30F is composed of the same components as those of the circuit 30B. Thus, the circuit 30F includes the transistor 33, the terminal 30a, the terminal 30b, and the terminal 30c. Note that the terminal 30c is not shown in FIG. 6A1; alternatively, a matching condition for decoding the input signal DAf, which is supplied to the gate of the transistor included in the circuit 30F, is shown. The matching condition for decoding the input signal DAf is different from that for the input signal DAb. The gate of the transistor 33 is supplied with the output signal QB0.

Next, FIG. 6A2 is a circuit diagram illustrating the circuit 20G. The circuit 20G includes the transistor 21 and a circuit 30G. The circuit 30G is composed of the same components as those of the circuit 30D.

The matching condition for decoding the input signal DAg will be described. The gate of the transistor 34 is supplied with the output signal QB0. The gate of the transistor 35 is supplied with the output signal Q1. The gate of the transistor 36 is supplied with the output signal Q0. The gate of the transistor 37 is supplied with the output signal QB1. The gate of the transistor 38 is supplied with an output signal QB3.

Next, FIG. 6A3 is a circuit diagram illustrating the circuit 20H. The circuit 20H includes the transistor 21 and a circuit 30H. The circuit 30H includes a transistor 3D to a transistor 3H, a transistor 3J, and a transistor 3K.

The matching condition for decoding the input signal DAh will be described. A gate of the transistor 3D is supplied with the output signal QB0. A gate of the transistor 3E is supplied with the output signal Q2. A gate of the transistor 3F is supplied with the output signal QB1. A gate of the transistor 3G is supplied with the output signal Q2. A gate of the transistor 3H is supplied with the output signal Q0. A gate of the transistor 3J is supplied with the output signal Q1. A gate of the transistor 3K is supplied with the output signal QB2.

The terminal 30a of the circuit 30H is electrically connected to one of a source and a drain of the transistor 3D, one of a source and a drain of the transistor 3F, and one of a source and a drain of the transistor 3H. The other of the source and the drain of the transistor 3D is electrically connected to one of a source and a drain of the transistor 3E. The other of the source and the drain of the transistor 3F is electrically connected to one of a source and a drain of the transistor 3G. The other of the source and the drain of the transistor 3H is electrically connected to one of a source and a drain of the transistor 3J. The other of the source and the drain of the transistor 3J is electrically connected to one of a source and a drain of the transistor 3K. The terminal 30b of the circuit 30H is electrically connected to the other of the source and the drain of the transistor 3E, the other of the source and the drain of the transistor 3G, and the other of the source and the drain of the transistor 3K.

Next, FIG. 6A4 is a circuit diagram illustrating the circuit 20J. The circuit 20J includes the transistor 21 and a circuit 30J. The circuit 30J is composed of the same components as those of the circuit 30D.

The matching condition for decoding the input signal DAj will be described. The gate of the transistor 34 is supplied with the output signal QB1. The gate of the transistor 35 is supplied with an output signal Q3. The gate of the transistor 36 is supplied with the output signal Q0. The gate of the transistor 37 is supplied with the output signal Q1. The gate of the transistor 38 is supplied with the output signal Q2.

When the input signal DAf of the latch circuit 10F is expressed by Formula 10, the decade counter circuit 60B operates.

(Formula 10)

$$DAf=QB0 \qquad (10)$$

The input signal DAg of the latch circuit 10G can be represented by the logical sum of the logical product of the first term and the logical product of the second term as in Formula 11.

(Formula 11)

$$DAg=QB0 \cdot Q1+Q0 \cdot QB1 \cdot QB3 \qquad (11)$$

The input signal DAh of the latch circuit 10H can be represented by the logical sum of the logical product of the first term, the logical product of the second term, and the logical product of the third term as in Formula 12.

(Formula 12)

$$DAh=QB0 \cdot Q2+QB1 \cdot Q2+Q0 \cdot Q1 \cdot QB2 \qquad (12)$$

The input signal DAj of the latch circuit 10J can be represented by the logical sum of the logical product of the first term and the logical product of the second term as in Formula 13.

(Formula 13)

$$DAj=QB1 \cdot Q3+Q0 \cdot Q1 \cdot Q2 \qquad (13)$$

Figure 7:
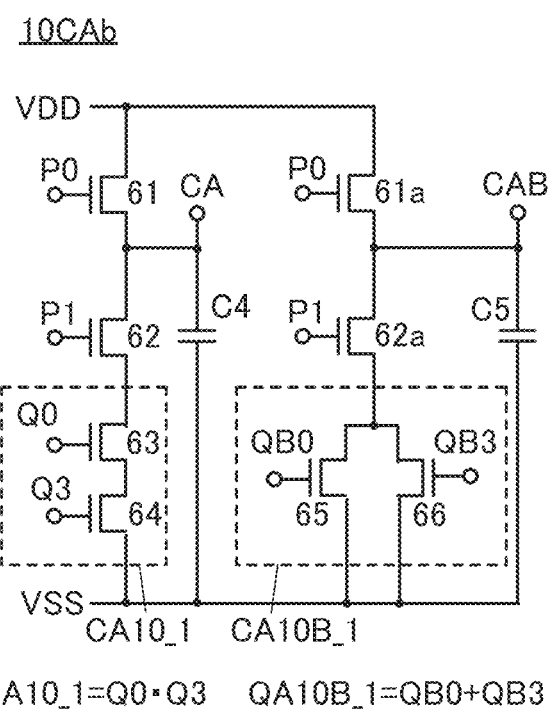
FIG. 7 is a circuit diagram illustrating a semiconductor device.

Next, FIG. 7 is a circuit explaining the circuit 10CAb. The circuit 10CAb is composed of the same components as those of the circuit 10CA. Thus, the circuit 10CAb includes the transistor 61 to the transistor 66, the transistor 61a, the transistor 62a, the capacitor C4, the capacitor C5, the terminal 10c1, the terminal 10c2, the terminal 10c3, and the terminal 10c4. Note that the terminal 10c1 and the terminal 10c2 are not shown in FIG. 7; alternatively, a matching condition for decoding the output signals Q[3:0] or the output signals QB[3:0], which is supplied to the gates of the transistors included in the circuit 10CAb, is shown. Note that for the description of the circuit of the circuit 10CAb, reference can be made to the description of the circuit 10CA in FIG. 2C.

Here, the matching condition where the circuit 10CAb performs decoding will be described. The gate of the transistor 63 is supplied with the output signal Q0. The gate of the transistor 64 is supplied with the output signal Q3. The gate of the transistor 65 is supplied with the output signal QB0. The gate of the transistor 66 is supplied with the output signal QB3.

The circuit 10CAb can set the matching condition for decoding the output signals Q[3:0] and the matching condition for decoding the output signals QB[3:0]. The matching condition for decoding the output signals Q[3:0] is created with a logical formula CA10_1. The matching condition for decoding the output signals QB[3:0] is created with a logical formula CA10B_1. When the logical formula CA10_1 can be represented by the logical product as in Formula 14, the decade counter circuit 60B operates.

(Formula 14)

$$CA10\_1=Q0 \cdot Q3 \qquad (14)$$

The logical formula CA10B_1 can be represented by the logical sum as in Formula 15.

(Formula 15)

$$CA10B\_1=QB0+QB3 \qquad (15)$$

Figure 8A:
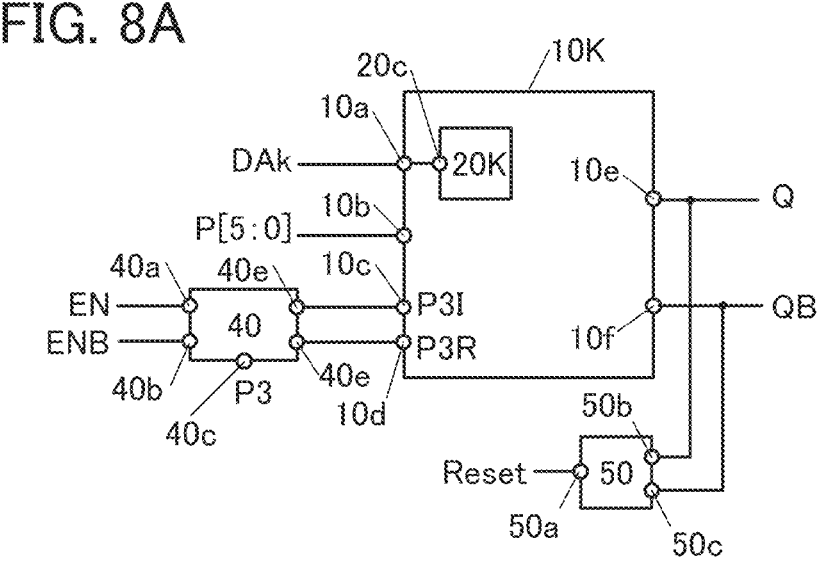
FIG. 8A is a block diagram illustrating a semiconductor device.

FIG. 8A is a block diagram illustrating a latch circuit 10K. FIG. 8A is different from the latch circuit 10 in including a circuit 50. The circuit 50 includes a terminal 50a, a terminal 50b, and a terminal 50c. The circuit 50 can reset the latch circuit 10K. Note that the circuit 50 can reset a plurality of latch circuits at the same time. The circuit 40 may be included in the latch circuit 10K or may drive a plurality of latch circuits at the same time.

Figure 8B:
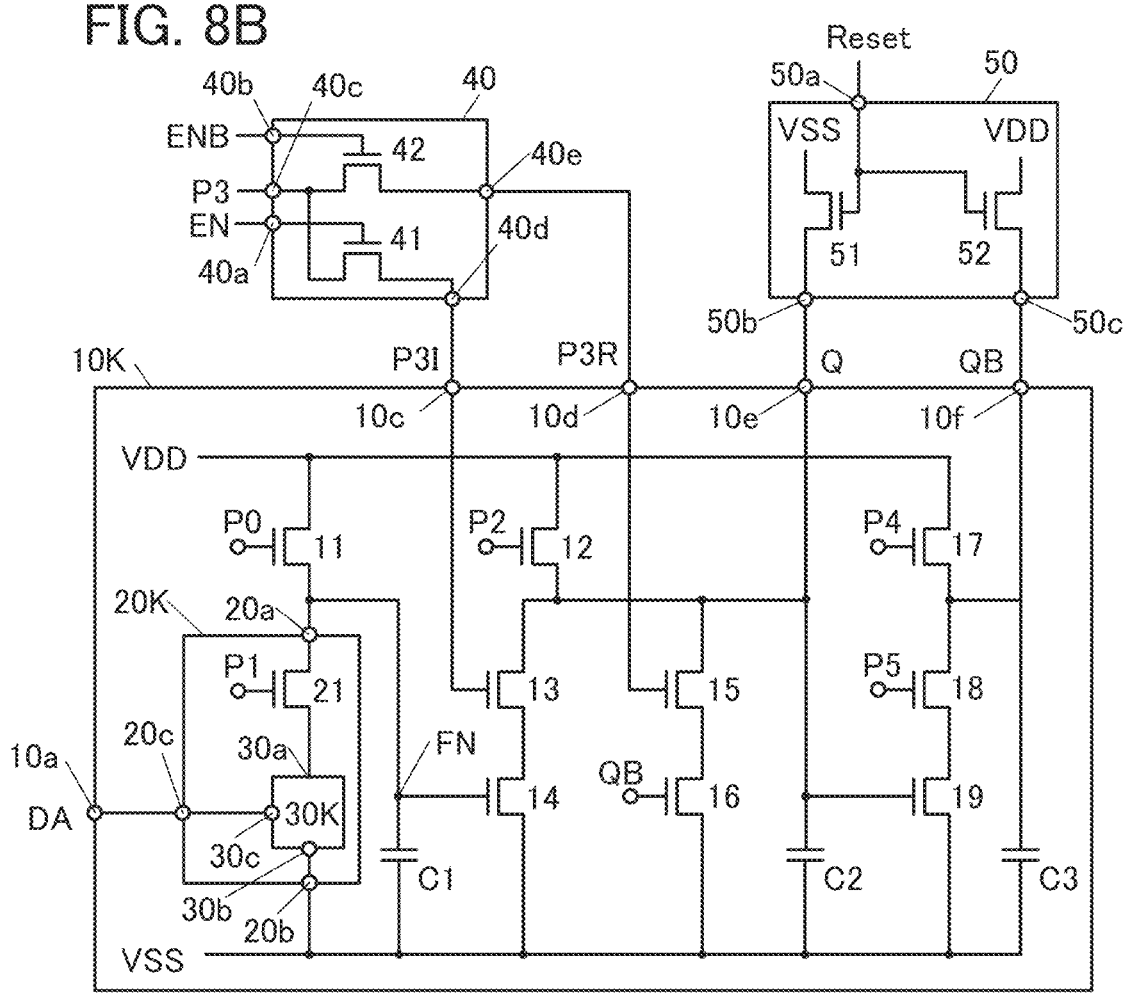
FIG. 8B is a circuit diagram illustrating a semiconductor device.

FIG. 8B is a circuit diagram illustrating the details of the latch circuit 10K. Here, the circuit 50 will be described in detail. For the other components of the latch circuit 10K, reference can be made to the description of the latch circuit 10 in FIG. 1B; thus, the description is omitted.

The circuit 50 includes a transistor 51 and a transistor 52. A signal Reset is supplied to a gate of the transistor 51 and a gate of the transistor 52 through the terminal 50a. One of a source and a drain of the transistor 51 is electrically connected to the wiring VSS. One of a source and a drain of the transistor 52 is electrically connected to the wiring VDD. The other of the source and the drain of the transistor 51 is electrically connected to the output terminal 10e through the terminal 50b. The other of the source and the drain of the transistor 52 is electrically connected to the output terminal 10f through the terminal 50c.

A period during which the signal Reset is supplied to the terminal 50a of the circuit 50 will be described. A reference potential supplied to the wiring VSS is supplied to the output terminal 10e of the latch circuit 10K through the transistor 51. A potential supplied to the wiring VDD is supplied to the output terminal 10f of the latch circuit 10K through the transistor 52. Note that the reference potential supplied to the wiring VSS corresponds to the "L" signal, and the potential supplied to the wiring VDD corresponds to the "H" signal.

In a period during which the latch circuit 10K is reset, the clock signal P2 is preferably the "L" signal. When the clock signal P2 is the "L" signal, the generation of shoot-through current through the transistor 12, the transistor 15, and the transistor 16 in discharging the capacitor C2 is inhibited. In addition, the clock signal P5 is preferably the "L" signal. When the clock signal P5 is the "L" signal, the generation of shoot-through current in charging the capacitor C2 is inhibited.

Figure 9A:
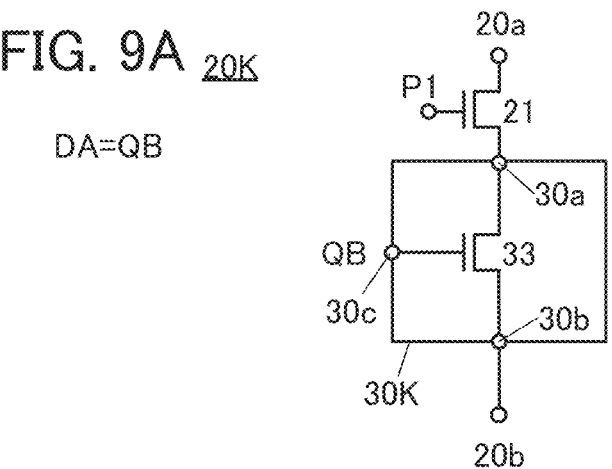
FIG. 9A is a circuit diagram illustrating a semiconductor device.

FIG. 9A is a circuit diagram illustrating a circuit 20K included in the latch circuit 10K. The circuit 20K includes the transistor 21 and a circuit 30K. The circuit 30K is composed of the same components as those of the circuit 20B. Note that the output signal QB is supplied to the terminal 30c.

Figure 9B:
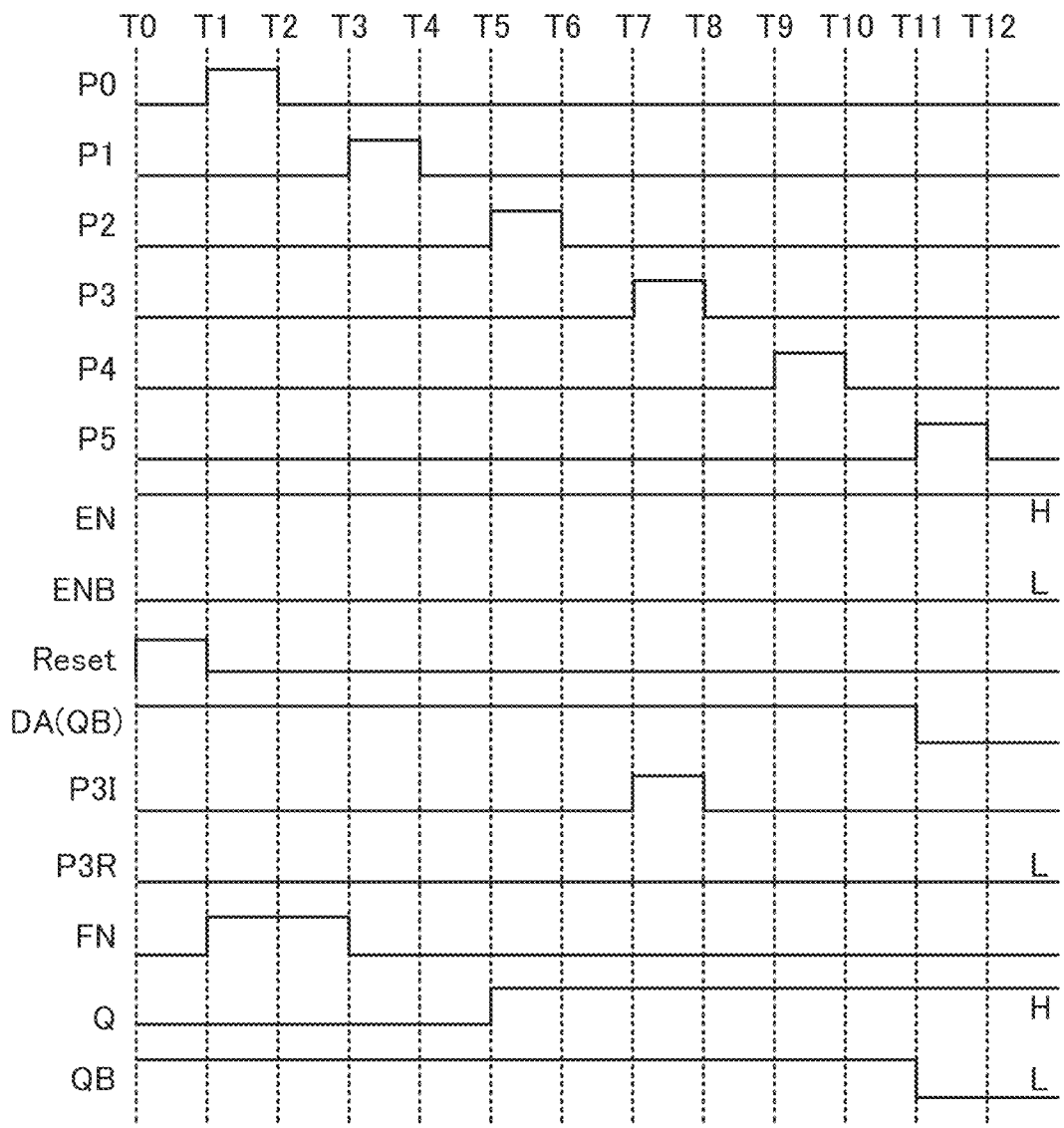
FIG. 9B is a timing chart showing a semiconductor device.

FIG. 9B is a timing chart showing the operation of the latch circuit 10K. Note that in the timing chart shown in FIG. 9B, the "H" signal and the "L" signal are supplied to the signal EN and the signal ENB, respectively, of the latch circuit 10K, so that an input signal can be latched.

At Time T0, the "H" potential is supplied to the signal Reset. The output signal Q changes to the "L" signal. The output signal QB changes to the "H" signal.

At Time T1, the "H" signal is supplied to the clock signal P0. Thus, the node FN is precharged through the transistor 11 and changes to the "H" signal. The transistor 14 is turned on because of the node FN changing to the "H" signal. Note that since the transistor 13 is in the off state, the output signal Q of the output terminal 10e does not change. Note that as shown in FIG. 9B, the signal Reset preferably changes to the "L" signal.

At Time T2, the "L" signal is supplied to the clock signal P0. A period during which the "L" signal is supplied to both the clock signal P0 and the clock signal P1 can inhibit shoot-through current from flowing through the transistor 11 and the circuit 20K.

At Time T3, the "H" signal is supplied to the clock signal P1. Since the "H" signal is supplied to the signal Reset from Time T0 to Time T1, the output terminal QB outputs the "H" signal. Thus, the transistor 21 and the transistor 33 are turned on. Accordingly, the circuit 20K is brought into conduction and is turned on. This changes the potential of the node FN to the "L" signal, and the transistor 14 is turned off.

At Time T4, the "L" signal is supplied to the clock signal P1. A period during which the "L" signal is supplied to both the clock signal P0 and the clock signal P1 leads to retention of the signal state of the node FN. FIG. 9B shows the case where the "L" signal is retained in the node FN.

At Time T5, the "H" signal is supplied to the clock signal P2. Thus, the capacitor C2 is precharged through the transistor 12 and changes to the "H" signal. This changes the output signal Q to the "H" signal. Accordingly, the potential of the gate of the transistor 19 becomes "H", so that the transistor 19 is turned on. Note that since the transistor 18 is in the off state, the output signal QB does not change.

At Time T6, the "L" signal is supplied to the clock signal P2. A period during which the "L" signal is supplied to both the clock signal P2 and the clock signal P3 results in the off state of both the transistor 12 and the transistor 13, so that the signal state of the output signal Q is retained in the capacitor C2. FIG. 9B shows the case where the output signal Q keeps being the "H" signal.

At Time T7, the "H" signal is supplied to the clock signal P3. As described above, the "H" signal is supplied to the wiring EN, and the "L" signal is supplied to the wiring ENB. Thus, the clock signal P3I changes to the "H" signal, and the transistor 13 is turned on. Note that since the node FN retains the "L" signal, the transistor 14 is in the off state. Hence, the voltage precharged in the capacitor C2 is not discharged, so that the output signal Q keeps being the "H" signal.

At Time T8, the "L" signal is supplied to the clock signal P3. The period during which the "L" signal is supplied to both the clock signal P2 and the clock signal P3 results in the off state of both the transistor 12 and the transistor 13, so that the signal state of the output signal Q is retained. FIG. 9B shows the case where the output signal Q keeps being the "H" signal.

At Time T9, the "H" signal is supplied to the clock signal P4. This establishes electrical continuity between the wiring VDD and the capacitor C3 through the transistor 17, and the capacitor C3 is precharged to the "H" potential. Note that since the capacitor C3 retains the "H" signal because the "H" signal is supplied to the signal Reset from Time T0 to Time T1 in FIG. 9B, the potential of the capacitor C3 does not change. Thus, the output signal QB keeps being the "H" signal.

At Time T10, the "L" signal is supplied to the clock signal P4. A period during which the "L" signal is supplied to both the clock signal P4 and the clock signal P5 results in the off state of both the transistor 17 and the transistor 18, so that the signal state of the output signal QB is retained in the capacitor C3. FIG. 9B shows the case where the output signal QB keeps being the "H" signal.

At Time T11, the "H" signal is supplied to the clock signal P5. Thus, the transistor 18 is turned on. In addition, since the capacitor C2 retains the "H" signal, the transistor 19 is in the on state. Accordingly, the voltage precharged in the capacitor C3 is discharged through the transistor 18 and the transistor 19, and the output signal QB changes to the "L" signal. When the output signal QB changes to the "L" signal, the "L" signal is supplied to the input signal DA.

At Time T12, the "L" signal is supplied to the clock signal P5. The period during which the "L" signal is supplied to both the clock signal P4 and the clock signal P5 results in the off state of both the transistor 17 and the transistor 18, so that the signal state of the output signal QB is retained in the capacitor C3. FIG. 9B shows the case where the output signal QB keeps being the "L" signal.

Figure 10A:
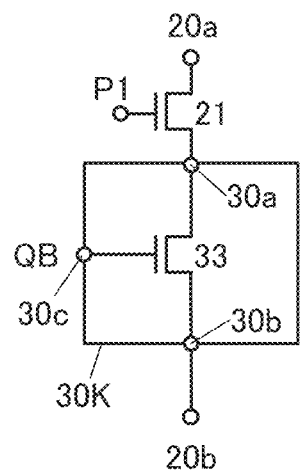
FIG. 10A is a circuit diagram illustrating a semiconductor device.

FIG. 10A is a circuit diagram illustrating the circuit 20K included in the latch circuit 10K. The circuit 20K is composed of the same components as those in FIG. 9A; thus, the description thereof is omitted.

Figure 10B:
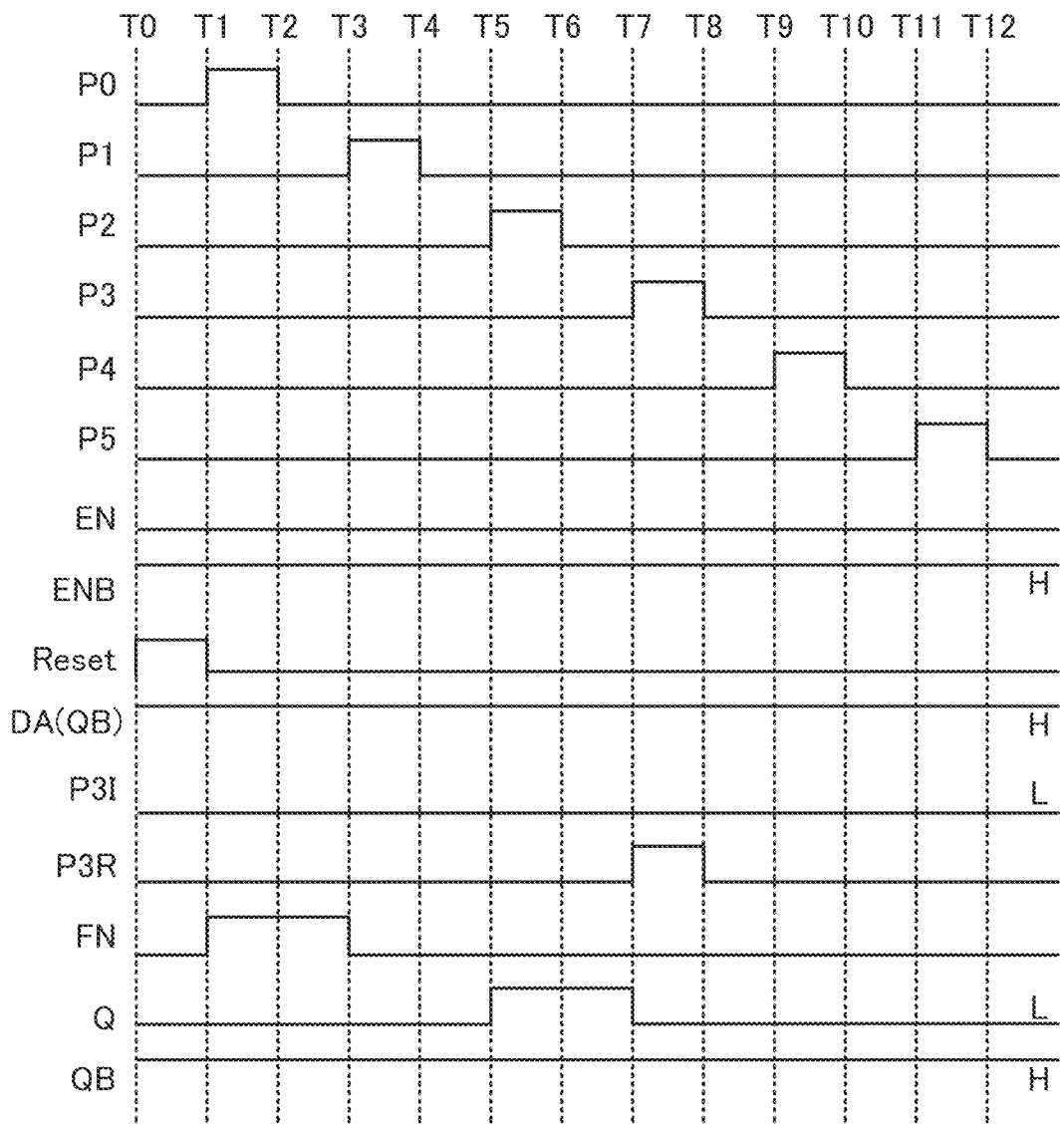
FIG. 10B is a timing chart showing a semiconductor device.

FIG. 10B is a timing chart showing the operation of the latch circuit 10K. Note that in the timing chart shown in FIG. 10B, the "H" signal and the "L" signal are supplied to the signal ENB and the signal EN, respectively, of the latch circuit 10K. The output signal Q or the output signal QB is thus refreshed, reducing the signal deterioration. Note that the operation from Time T0 to T6 is the same as that in FIG. 9B; thus, the description thereof is omitted and the operation after Time T7 will be described.

At Time T7, the "H" signal is supplied to the clock signal P3, the "L" signal is supplied to the wiring EN, and the "H" signal is supplied to the wiring ENB. Thus, the transistor 42 is turned on, the clock signal P3R changes to the "H" signal, and the transistor 15 is turned on. Since the output signal QB keeps being the "H" signal, the transistor 16 is in the on state. Hence, the voltage precharged in the capacitor C2 is discharged. Accordingly, the output signal Q changes to the "L" signal.

At Time T8, the "L" signal is supplied to the clock signal P3. The period during which the "L" signal is supplied to both the clock signal P2 and the clock signal P3 results in the off state of both the transistor 12 and the transistor 15, so that the signal state of the output signal Q is retained in the capacitor C2. FIG. 9B shows the case where the output signal Q keeps being the "L" signal.

At Time T9, the "H" signal is supplied to the clock signal P4. This establishes electrical continuity between the wiring VDD and the capacitor C3 through the transistor 17, and the capacitor C3 is precharged to the "H" potential. Note that since the capacitor C3 retains the "H" signal because the "H" signal is supplied to the signal Reset from Time T0 to Time T1 in FIG. 9B, the potential of the capacitor C3 does not change. Thus, the output signal QB keeps being the "H" signal.

At Time T10, the "L" signal is supplied to the clock signal P4. The period during which the "L" signal is supplied to both the clock signal P4 and the clock signal P5 results in the off state of both the transistor 17 and the transistor 18, so that the signal state of the output signal QB is retained in the capacitor C3. FIG. 9B shows the case where the output signal QB keeps being the "H" signal.

At Time T11, the "H" signal is supplied to the clock signal P5. Thus, the transistor 18 is turned on. In addition, since the capacitor C2 retains the "L" signal, the transistor 19 is in the off state. Accordingly, the voltage precharged in the capacitor C3 is not discharged. Thus, the output signal QB keeps being the "H" signal. When the output signal QB keeps being the "H" signal, the "H" signal is supplied to the input signal DA.

At Time T12, the "L" signal is supplied to the clock signal P5. The period during which the "L" signal is supplied to both the clock signal P4 and the clock signal P5 results in the off state of both the transistor 17 and the transistor 18, so that the signal state of the output signal QB is retained in the capacitor C3. FIG. 9B shows the case where the output signal QB keeps being the "H" signal.

Figure 11:
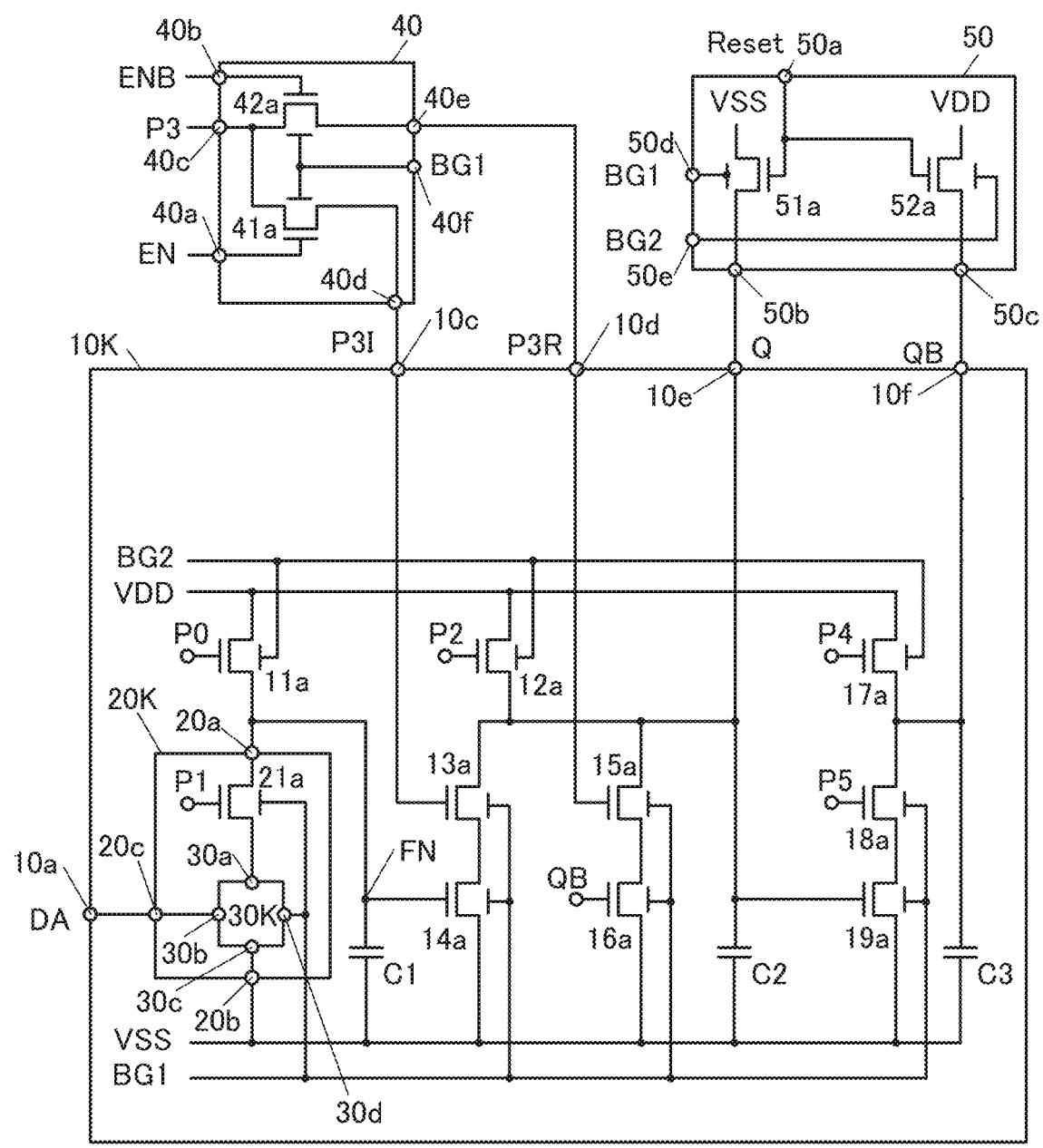
FIG. 11 is a circuit diagram illustrating a semiconductor device.

FIG. 11 is a circuit diagram illustrating the latch circuit 10K. The latch circuit in FIG. 11 is different from the latch circuit 10K illustrated in FIG. 8A in that transistors each have a back gate. When a transistor has a back gate, the threshold voltage of the transistor can be controlled.

A wiring BG1 is electrically connected to back gates of a transistor 13a, a transistor 14a, a transistor 15a, a transistor 16a, a transistor 18a, a transistor 19a, a transistor 21a, a transistor 41a, a transistor 42a, and a transistor 51a. A wiring BG2 is electrically connected to back gates of a transistor 11a, a transistor 12a, a transistor 17a, and a transistor 52a.

A potential VBG1 is supplied to the wiring BG1. A potential VBG2 is supplied to the wiring BG2. Different potentials are preferably supplied to the potential VBG1 and the potential VBG2.

A potential higher than the potential VBG1 is supplied as the potential VBG2, for example. When the potential of the potential VBG2 is high, the threshold voltage of the transistor 11a, the transistor 12a, and the transistor 17a can be made lower than that of the transistor 13a or the transistor 14a, for example, which can increase the on-state current. Increasing the on-state current of the transistor 11a, the transistor 12a, and the transistor 17a can increase the speed of charging the capacitors C1 to C3. Furthermore, the charging potentials of the capacitors C1 to C3 can be made low, reducing the power consumption of the latch circuit 10K.

Note that one electrode of the capacitor C2 is connected to the output terminal 10e; thus, the current supply capability in the case where the "H" signal is output to the output terminal 10e can be improved. Similarly, one electrode of the capacitor C3 is connected to the output terminal 10f; thus, the current supply capability in the case where the "H" signal is output to the output terminal 10f can be improved.

A potential lower than the potential VBG2 is supplied as the potential VBG1. When the potential of the potential VBG1 is low, the off-state current of the transistor 13a, the transistor 14a, the transistor 15a, the transistor 16a, the transistor 18a, and the transistor 19a is low.

Low off-state current of the transistor 13 or the transistor 14 results in low leakage current from the capacitor C2 through the transistor 13 and the transistor 14, for example. Similarly, low off-state current of the transistor 18a or the transistor 19a results in low leakage current from the capacitor C3 through the transistor 18a and the transistor 19a.

Figure 12:
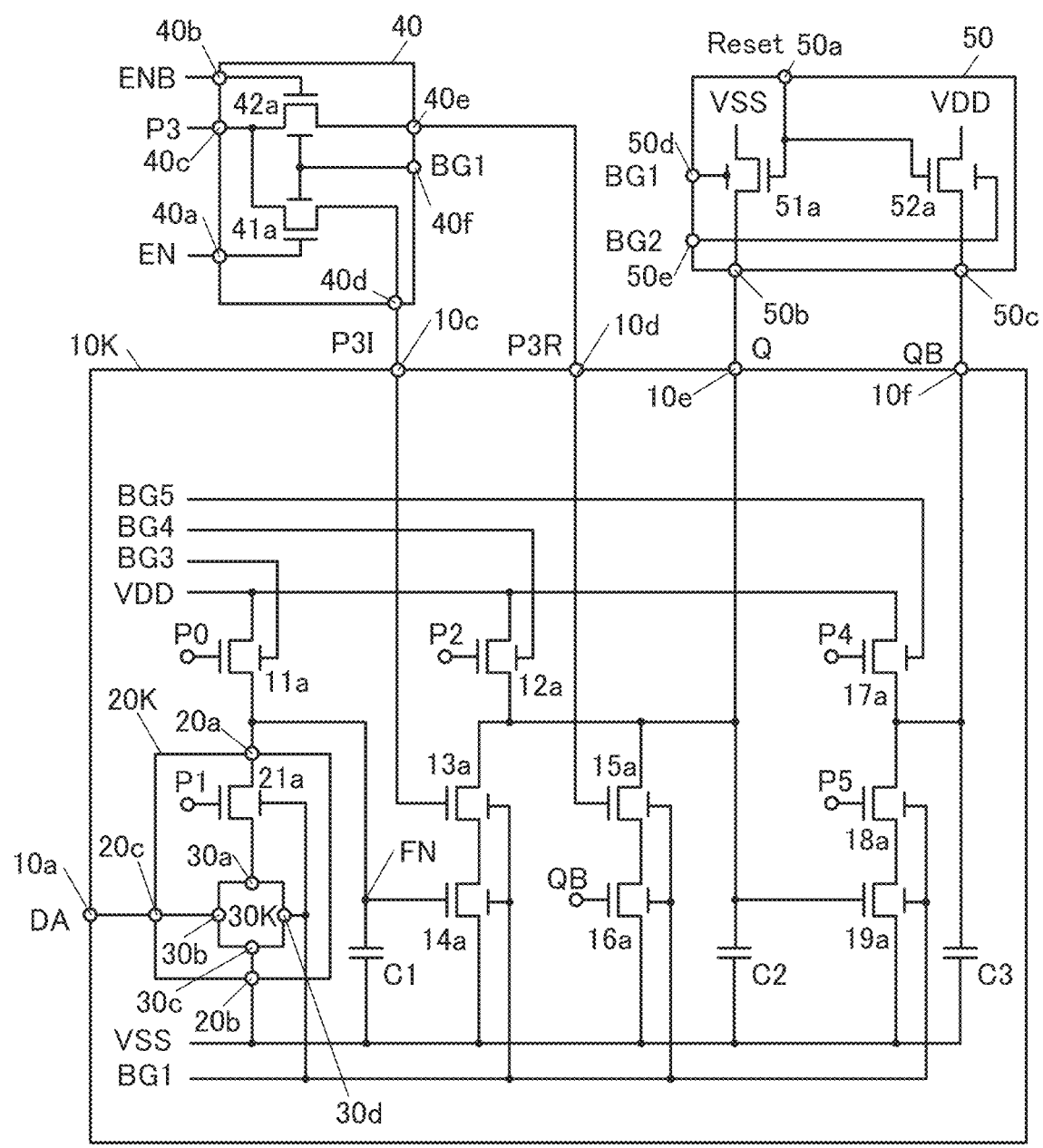
FIG. 12 is a circuit diagram illustrating a semiconductor device.

FIG. 12 is a circuit diagram illustrating the latch circuit 10K. The latch circuit in FIG. 12 is different from the latch circuit 10K illustrated in FIG. 11 in that the back gates of the transistor 11a, the transistor 12a, and the transistor 17a are connected to different wirings.

A wiring BG3 is electrically connected to the transistor 11a. A wiring BG4 is electrically connected to the transistor 12a. A wiring BG5 is electrically connected to the transistor 17a.

A potential VBG3 is supplied to the wiring BG3, a potential VBG4 is supplied to the wiring BG4, and a potential VBG5 is supplied to the wiring BG3.

When the "H" signal is supplied to the clock signal P0, the potential VBG3 is preferably higher than the potential VBG1. This increases the speed of precharging the node FN. In addition, the potential VBG4 and the potential VBG5 are preferably supplied with the same potential as the potential VBG1. This reduces the off-state current of the transistor 12a and the transistor 17a, which can inhibit signal deterioration of the output signal Q and the output signal QB.

When the "H" signal is supplied to the clock signal P2, the potential VBG4 is preferably higher than the potential VBG1. This increases the speed of precharging the capacitor C2 and improves the driving capability of the output signal Q. In addition, the potential VBG3 and the potential VBG5 are preferably supplied with the same potential as the potential VBG1. This reduces the off-state current of the transistor 11a and the transistor 17a, which can inhibit signal deterioration of the node FN and the output signal QB.

When the "H" signal is supplied to the clock signal P4, the potential VBG5 is preferably higher than the potential VBG1. This increases the speed of precharging the capacitor C3 and improves the driving capability of the output signal QB. In addition, the potential VBG3 and the potential VBG4 are preferably supplied with the same potential as the potential VBG1. This reduces the off-state current of the transistor 11a and the transistor 12a, which can inhibit signal deterioration of the node FN and the output signal Q.

The latch circuits illustrated in FIG. 1 to FIG. 12 can each be referred to as a dynamic circuit. Although the ternary counter circuit, the senary counter circuit, and the decade counter circuit are described above, the latch circuit composed of the dynamic circuit can be used for a counter circuit with other radices when the matching conditions for decoding are combined. Thus, the latch circuit composed of the dynamic circuit can reduce the power consumption and is suitable for producing a cycle as necessary.

The structure and method described in this embodiment can be used by being combined as appropriate with the structures and methods described in the other embodiments.

Embodiment 2

In this embodiment, an example of the transistor described in Embodiment 1 will be described with reference to FIG. 13 and FIG. 14.

Figure 13A:
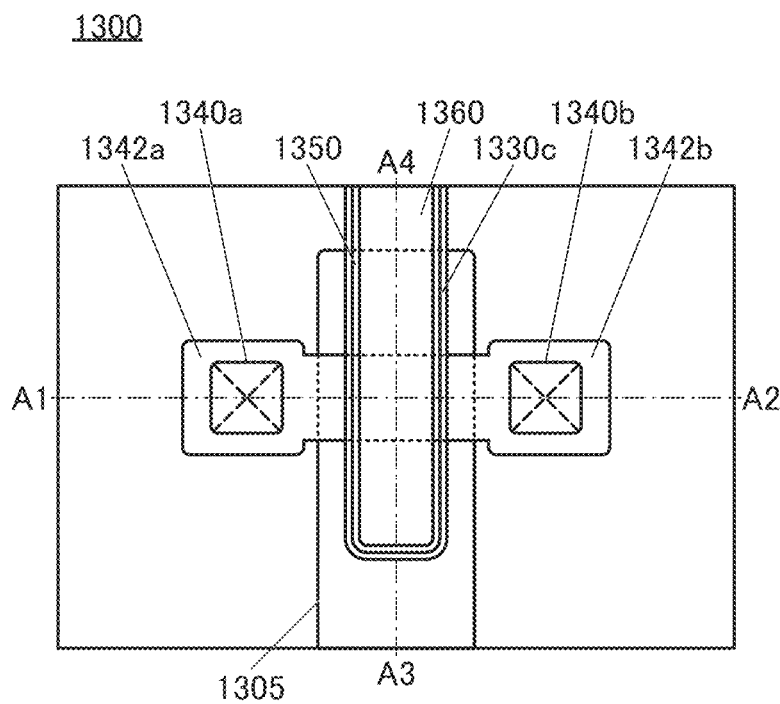
FIG. 13A is a top view illustrating an example of a transistor.
Figure 13C:
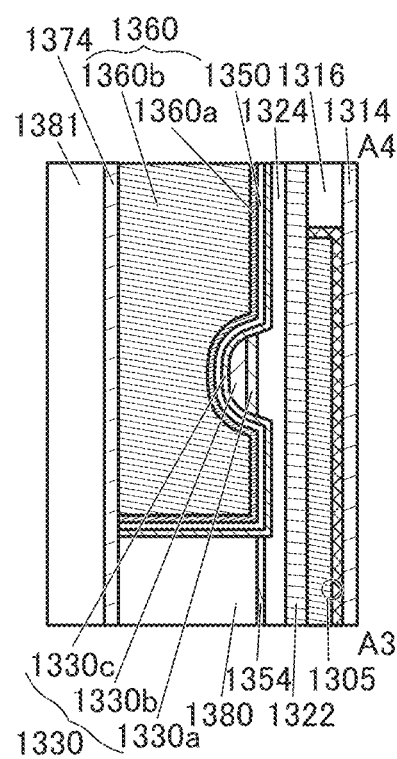
FIG. 13B and FIG. 13C are cross-sectional views illustrating an example of a transistor.
Figure 13B:
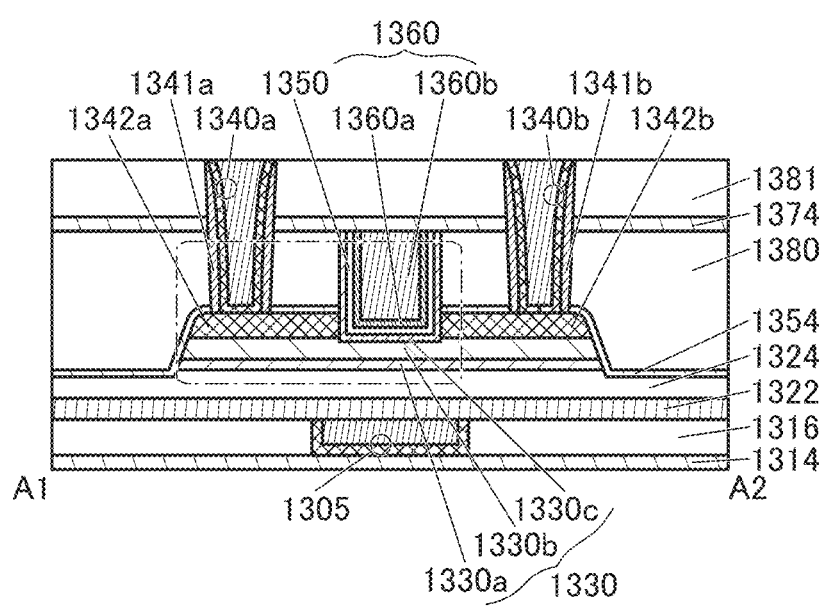

FIG. 13A illustrates a top view of a transistor 1300. Note that for simplification of the drawing, some components are not illustrated in FIG. 13A. FIG. 13B illustrates a cross-sectional view taken along the dashed-dotted line A1-A2 in FIG. 13A. FIG. 13B can be referred to as a cross-sectional view of the transistor 1300 in the channel length direction. FIG. 13C illustrates a cross-sectional view taken along the dashed-dotted line A3-A4 in FIG. 13A. FIG. 13C can be referred to as a cross-sectional view of the transistor 1300 in the channel width direction.

Figure 14A:
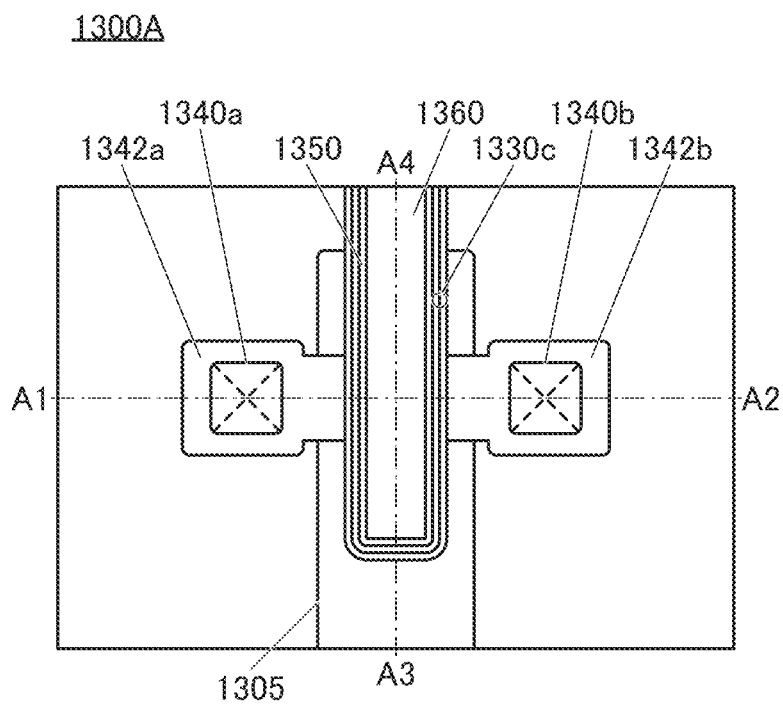
FIG. 14A is a top view illustrating an example of a transistor.
Figure 14C:
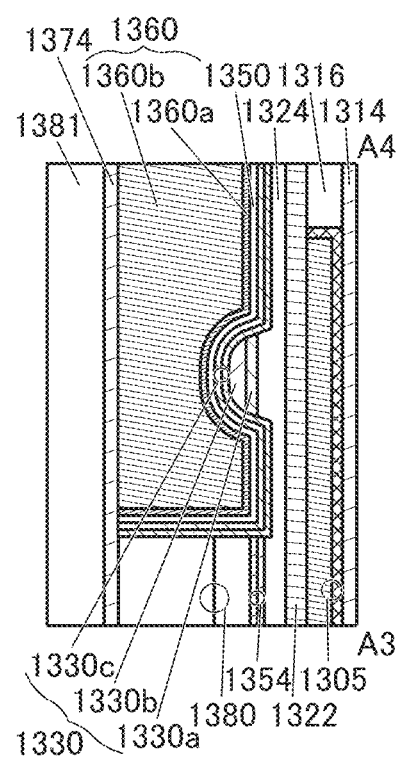
FIG. 14B and FIG. 14C are cross-sectional views illustrating an example of a transistor.
Figure 14B:
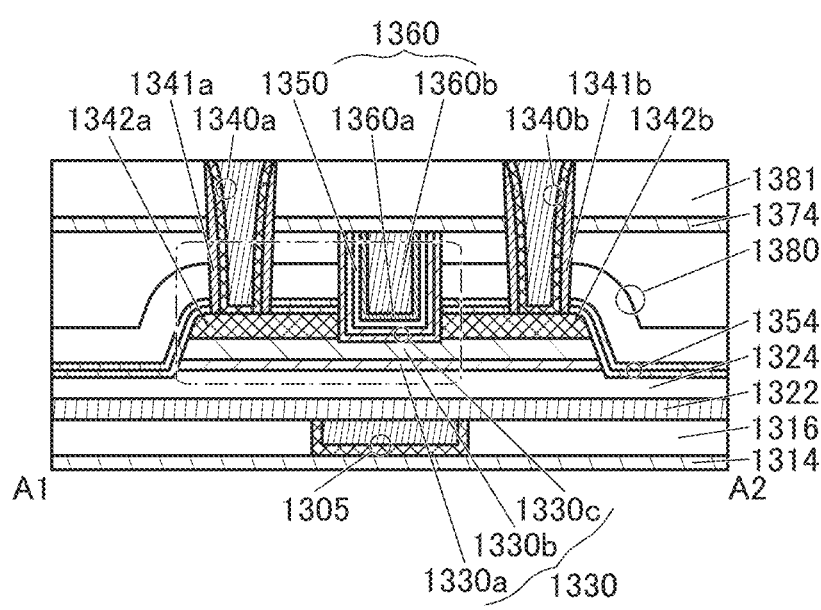

FIG. 14A illustrates a top view of a transistor 1300A. Note that for simplification of the drawing, some components are not illustrated in FIG. 14A. FIG. 14B illustrates a cross-sectional view taken along the dashed-dotted line A1-A2 in FIG. 14A. FIG. 14B can be referred to as a cross-sectional view of the transistor 1300A in the channel length direction. FIG. 14C illustrates a cross-sectional view taken along the dashed-dotted line A3-A4 in FIG. 14A. FIG. 14C can be referred to as a cross-sectional view of the transistor 1300A in the channel width direction.

Note that the transistor 1300A illustrated in FIG. 14 is a variation example of the transistor 1300 illustrated in FIG. 13. Each of an oxide layer 1330c, an insulating layer 1354, and an insulating layer 1380 has a single-layer structure in FIG. 13 and has a stacked-layer structure in FIG. 14. The other components in FIG. 13 are the same as those in FIG. 14.

The transistor 1300 includes a conductive layer 1305 provided over a substrate (not illustrated) with an insulating layer 1314 therebetween and provided to be embedded in an insulating layer 1316; an insulating layer 1322 provided over the insulating layer 1316 and the conductive layer 1305; an insulating layer 1324 provided over the insulating layer 1322; an oxide layer 1330 (an oxide layer 1330a, an oxide layer 1330b, and the oxide layer 1330c) provided over the insulating layer 1324; an insulating layer 1350 provided over the oxide layer 1330; a conductive layer 1360 (a conductive layer 1360a and a conductive layer 1360b) provided over the insulating layer 1350; a conductive layer 1342a and a conductive layer 1342b in contact with part of a top surface of the oxide layer 1330b; and the insulating layer 1354 provided in contact with part of a top surface of the insulating layer 1324, a side surface of the oxide layer 1330a, a side surface of the oxide layer 1330b, a side surface and a top surface of the conductive layer 1342a, and a side surface and a top surface of the conductive layer 1342b.

The insulating layer 1380, an insulating layer 1374, and an insulating layer 1381 each functioning as an interlayer film are provided over the transistor 1300. The transistor 1300 is electrically connected to a conductive layer 1340 (a conductive layer 1340a and a conductive layer 1340b) functioning as a plug. Note that an insulating layer 1341 (an insulating layer 1341a and an insulating layer 1341b) is provided in contact with a side surface of the conductive layer 1340.

The oxide layer 1330 preferably includes the oxide layer 1330a provided over the insulating layer 1324; the oxide layer 1330b provided over the oxide layer 1330a; and the oxide layer 1330c which is provided over the oxide layer 1330b and at least part of which is in contact with a top surface of the oxide layer 1330b. When the oxide layer 1330a is provided under the oxide layer 1330b, impurities can be inhibited from being diffused into the oxide layer 1330b from the components formed below the oxide layer 1330a. When the oxide layer 1330c is provided over the oxide layer 1330b, impurities can be inhibited from being diffused into the oxide layer 1330b from the components formed above the oxide layer 1330c.

Although an example of the transistor 1300 in which the oxide layer 1330 has a three-layer structure of the oxide layer 1330a, the oxide layer 1330b, and the oxide layer 1330c is described, the present invention is not limited thereto. For example, the oxide layer 1330 may have a single-layer structure of the oxide layer 1330b, a two-layer structure of the oxide layer 1330a and the oxide layer 1330b, a two-layer structure of the oxide layer 1330b and the oxide layer 1330c, or a stacked-layer structure of four or more layers. Alternatively, each of the oxide layer 1330a, the oxide layer 1330b, and the oxide layer 1330c may have a stacked-layer structure.

The conductive layer 1342 (the conductive layer 1342a and the conductive layer 1342b) is provided over the oxide layer 1330b. The thickness of the conductive layer 1342 can be, for example, greater than or equal to 1 nm and less than or equal to 50 nm, preferably greater than or equal to 2 nm and less than or equal to 25 nm.

The conductive layer 1360 functions as a first gate (also referred to as top gate) electrode of the transistor 1300, and the conductive layer 1342a and the conductive layer 1342b function as a source electrode and a drain electrode of the transistor 1300.

In the transistor 1300, a metal oxide functioning as a semiconductor (hereinafter, also referred to as an oxide semiconductor) is preferably used in the oxide layer 1330 including a channel formation region. When an oxide semiconductor is used in a channel formation region of a transistor, a transistor having high field-effect mobility can be achieved. In addition, a transistor having high reliability can be achieved.

As the above metal oxide, it is preferable to use a metal oxide having a band gap of 2.0 eV or more, preferably 2.5 eV or more. The use of a metal oxide having a wide band gap in the oxide layer 1330 can reduce the off-state current of the transistor. The use of such a transistor can provide an amplifier circuit with low power consumption.

For example, as the oxide layer 1330, a metal oxide such as an In-M-Zn oxide containing indium (In), an element M, and zinc (Zn) (the element M is one or more kinds selected from aluminum, gallium, yttrium, tin, copper, vanadium, beryllium, boron, titanium, iron, nickel, germanium, zirconium, molybdenum, lanthanum, cerium, neodymium, hafnium, tantalum, tungsten, magnesium, and the like) is preferably used. In particular, aluminum, gallium, yttrium, or tin is preferably used as the element M. Furthermore, an In-M oxide, an In—Zn oxide, or an M-Zn oxide may be used as the oxide layer 1330.

A metal oxide with a low carrier density is preferably used in the transistor 1300. In order to reduce the carrier density of the metal oxide, the concentration of impurities in the metal oxide is reduced so that the density of defect states can be reduced. In this specification and the like, a state with a low impurity concentration and a low density of defect states is referred to as a highly purified intrinsic or substantially highly purified intrinsic state. Examples of the impurities in the metal oxide include hydrogen, nitrogen, alkali metal, alkaline earth metal, iron, nickel, and silicon.

In particular, hydrogen contained in a metal oxide reacts with oxygen bonded to a metal atom to be water, and thus forms oxygen vacancies in the metal oxide in some cases. If the channel formation region in the metal oxide includes oxygen vacancies, the transistor sometimes has normally-on characteristics. In some cases, a defect that is an oxygen vacancy into which hydrogen enters functions as a donor and generates an electron serving as a carrier. In other cases, bonding of part of hydrogen to oxygen bonded to a metal atom generates electrons serving as carriers. Thus, a transistor using a metal oxide containing much hydrogen is likely to have normally-on characteristics.

Therefore, when a metal oxide is used for the oxide layer 1330, hydrogen in the metal oxide is preferably reduced as much as possible. Specifically, the hydrogen concentration of the metal oxide, which is measured by secondary ion mass spectrometry (SIMS), is lower than $1 \times 10^{20}$ atoms/cm$^3$, preferably lower than $1 \times 10^{19}$ atoms/cm$^3$, further preferably lower than $5 \times 10^{18}$ atoms/cm$^3$, still further preferably lower than $1 \times 10^{18}$ atoms/cm$^3$. When a metal oxide with a sufficiently low concentration of impurities such as hydrogen is used for a channel formation region of a transistor, the transistor can have stable electrical characteristics.

When a metal oxide is used for the oxide layer 1330, contact between the conductive layer 1342 (the conductive layer 1342*a* and the conductive layer 1342*b*) and the oxide layer 1330 may make oxygen in the oxide layer 1330 diffuse into the conductive layer 1342, resulting in oxidation of the conductive layer 1342. It is highly possible that oxidation of the conductive layer 1342 lowers the conductivity of the conductive layer 1342. Note that diffusion of oxygen from the oxide layer 1330 into the conductive layer 1342 can be interpreted as absorption of oxygen in the oxide layer 1330 by the conductive layer 1342.

When oxygen in the oxide layer 1330 is diffused into the conductive layer 1342 (the conductive layer 1342*a* and the conductive layer 1342*b*), a layer may be formed between the conductive layer 1342*a* and the oxide layers 1330*b* and 1330*c* and between the conductive layer 1342*b* and the oxide layers 1330*b* and 1330*c*. The layer contains more oxygen than the conductive layer 1342 does, and thus presumably has an insulating property. In this case, a three-layer structure of the conductive layer 1342, the layer, and the oxide layer 1330*b* or the oxide layer 1330*c* can be regarded as a three-layer structure of a metal, an insulator, and a semiconductor and is sometimes referred to as an MIS (Metal-Insulator-Semiconductor) structure.

In view of the above, the conductive layer 1342 (the conductive layer 1342*a* and the conductive layer 1342*b*) is preferably formed using a conductive material having properties with which hydrogen in the oxide layer 1330 easily diffuses into the conductive layer 1342 and oxygen in the oxide layer 1330 does not easily diffuse into the conductive layer 1342. Thus, with hydrogen in the oxide layer 1330 diffusing into the conductive layer 1342, the hydrogen concentration in the oxide layer 1330 is reduced, and the transistor 1300 can have stable electrical characteristics.

An example of the conductive material includes a conductor containing tantalum (Ta), titanium (Ti), or the like. In particular, a conductor containing tantalum is preferably used for the conductive layer 1342. A conductor containing tantalum may contain nitrogen and may contain oxygen. Accordingly, the composition formula of a conductor containing tantalum preferably satisfies $TaN_xO_y$ (x is a real number greater than 0 and less than or equal to 1.67 and y is a real number greater than or equal to 0 and less than or equal to 1.0). Examples of the conductor containing tantalum include metal tantalum, tantalum oxide, tantalum nitride, tantalum nitride oxide, and tantalum oxynitride. Thus, in this specification and the like, the conductor containing tantalum is sometimes referred to as $TaN_xO_y$.

In $TaN_xO_y$, the proportion of tantalum is preferably high. Alternatively, the proportions of nitrogen and oxygen are preferably low; i.e., x and y are preferably small. A high proportion of tantalum lowers the resistance of $TaN_xO_y$, and the transistor 1300 in which $TaN_xO_y$ is used for the conductive layer 1342 can have favorable electrical characteristics.

Alternatively, the proportion of nitrogen in $TaN_xO_y$ is preferably high; i.e., x is preferably large. The use of $TaN_xO_y$ with a high proportion of nitrogen in the conductive layer 1342 can inhibit oxidation of the conductive layer 1342. In addition, the thickness of a layer formed between the conductive layer 1342 and the oxide layer 1330 can be reduced.

Note that hydrogen diffused into the conductive layer 1342 sometimes remains in the conductive layer 1342. In other words, hydrogen in the oxide layer 1330 is absorbed by the conductive layer 1342 in some cases. In other cases, hydrogen in the oxide layer 1330 passes through the conductive layer 1342 and is released to a component provided around the conductive layer 1342 or the outside of the transistor 1300.

In order to reduce the hydrogen concentration of the oxide layer 1330 and to inhibit formation of a layer between the conductive layer 1342 and the oxide layer 1330, it is preferable that the conductive layer 1342 be formed using a conductive material having a property with which hydrogen in the oxide layer 1330 easily diffuses into the conductive layer 1342, and that a layer having a function of inhibiting oxidation of the conductive layer 1342 be provided between the conductive layer 1342 and the oxide layer 1330. Providing the layer makes the conductive layer 1342 and the oxide layer 1330 not in contact with each other, thereby inhibiting absorption of oxygen in the oxide layer 1330 by the conductive layer 1342.

The structure of the transistor 1300 will be described in detail below.

The insulating layer 1314 preferably functions as an insulating barrier film that inhibits diffusion of impurities such as water and hydrogen from the substrate side into the transistor 1300. Thus, for the insulating layer 1314, it is preferable to use an insulating material having a function of inhibiting diffusion of impurities such as a hydrogen atom, a hydrogen molecule, a water molecule, a nitrogen atom, a nitrogen molecule, a nitrogen oxide molecule ($N_2O$, NO, $NO_2$, or the like), and a copper atom. Alternatively, it is preferable to use an insulating material having a function of inhibiting diffusion of oxygen (e.g., at least one of an oxygen atom, an oxygen molecule, and the like).

Note that in this specification, a function of inhibiting diffusion of impurities or oxygen means a function of inhibiting diffusion of any one or all of the impurities and the oxygen. A film having a function of inhibiting diffusion of hydrogen or oxygen may be referred to as a film through which hydrogen or oxygen does not pass easily, a film having low permeability of hydrogen or oxygen, a film having a barrier property against hydrogen or oxygen, or a barrier film against hydrogen or oxygen, for example. A barrier film having conductivity is sometimes referred to as a conductive barrier film.

For example, an aluminum oxide film, a silicon nitride film, or the like is preferably used as the insulating layer 1314. Accordingly, impurities such as water and hydrogen can be inhibited from diffusing to the transistor 1300 side from the substrate side through the insulating layer 1314. Alternatively, oxygen contained in the insulating layer 1324 and the like can be inhibited from diffusing to the substrate side through the insulating layer 1314. Note that the insulating layer 1314 may have a stacked-layer structure of two or more layers. In that case, without limitation to a stacked-layer structure formed of the same material, a stacked-layer structure formed of different materials may be employed. For example, a stack of an aluminum oxide film and a silicon nitride film may be employed.

Furthermore, it is preferable to use, as the insulating layer 1314, a silicon nitride film deposited by a sputtering method, for example. Thus, the hydrogen concentration in the insulating layer 1314 can be made low, so that impurities such as water and hydrogen can be further inhibited from diffusing to the transistor 1300 side from the substrate side through the insulating layer 1314.

The dielectric constant of the insulating layer 1316 functioning as an interlayer film is preferably lower than that of the insulating layer 1314. When a material having a low dielectric constant is used for an interlayer film, parasitic capacitance generated between wirings can be reduced. As the insulating layer 1316, a silicon oxide film, a silicon oxynitride film, a silicon nitride oxide film, a silicon nitride film, a silicon oxide film to which fluorine is added, a silicon oxide film to which carbon is added, a silicon oxide film to which carbon and nitrogen are added, a porous silicon oxide film, or the like is used as appropriate, for example.

The insulating layer 1316 preferably includes a region that has a low hydrogen concentration and contains oxygen in excess of that in the stoichiometric composition (hereinafter, also referred to as an excess-oxygen region), or preferably contains oxygen that is released by heating (hereinafter, also referred to as excess oxygen). For example, a silicon oxide film deposited by a sputtering method is preferably used as the insulating layer 1316. Thus, entry of hydrogen into the oxide layer 1330 can be inhibited; alternatively, oxygen can be supplied to the oxide layer 1330 to reduce oxygen vacancies in the oxide layer 1330. Accordingly, a transistor that has stable electrical characteristics with a small variation in electrical characteristics and improved reliability can be provided.

The insulating layer 1316 may have a stacked-layer structure. For example, in the insulating layer 1316, a structure may be employed in which an insulating layer similar to the insulating layer 1314 is provided at least in a portion in contact with a side surface of the conductive layer 1305. With such a structure, oxidation of the conductive layer 1305 due to oxygen contained in the insulating layer 1316 can be inhibited. Alternatively, a reduction in the amount of oxygen contained in the insulating layer 1316 due to the conductive layer 1305 can be inhibited.

The conductive layer 1305 sometimes functions as a second gate (also referred to as bottom gate) electrode. In that case, by changing the potential applied to the conductive layer 1305 not in conjunction with but independently of the potential applied to the conductive layer 1360, the threshold voltage (Vth) of the transistor 1300 can be controlled. In particular, by applying a negative potential to the conductive layer 1305, Vth of the transistor 1300 can be higher, and its off-state current can be reduced. Thus, drain current at the time when a potential applied to the conductive layer 1360 is 0 V can be lower in the case where a negative potential is applied to the conductive layer 1305 than in the case where a negative potential is not applied.

The conductive layer 1305 is placed to include a region overlapping with the oxide layer 1330 and the conductive layer 1360. The conductive layer 1305 is preferably provided to be embedded in the insulating layer 1314 or the insulating layer 1316.

As illustrated in FIG. 13B, the conductive layer 1305 is preferably provided larger than the channel formation region in the oxide layer 1330. As illustrated in FIG. 13C, it is particularly preferable that the conductive layer 1305 also extend to a region outside an end portion of the oxide layer 1330 that intersects with the channel width direction. That is, the conductive layer 1305 and the conductive layer 1360 preferably overlap with each other with the insulating layers therebetween on an outer side of the side surface of the oxide layer 1330 in the channel width direction. With this structure, the channel formation region of the oxide layer 1330 can be electrically surrounded by the electric field of the conductive layer 1360 functioning as the first gate electrode and the electric field of the conductive layer 1305 functioning as the second gate electrode.

As illustrated in FIG. 13C, the conductive layer 1305 is extended to function as a wiring. However, without limitation to this structure, a structure in which a conductive layer functioning as a wiring is provided below the conductive layer 1305 may be employed. In addition, the conductive layer 1305 does not necessarily have to be provided in each transistor. For example, the conductive layer 1305 may be shared by a plurality of transistors.

Although an example of the transistor 1300 in which the conductive layer 1305 has a two-layer structure (a first conductive layer over the insulating layer 1314 and a second conductive layer over the first conductive layer) is described, the present invention is not limited to this. For example, the conductive layer 1305 may have a single-layer structure or a stacked-layer structure of three or more layers. In the case where a component has a stacked-layer structure, layers may be distinguished by ordinal numbers corresponding to the formation order.

Here, for the first conductive layer of the conductive layer 1305, a conductive material having a function of inhibiting diffusion of impurities such as a hydrogen atom, a hydrogen molecule, a water molecule, a nitrogen atom, a nitrogen molecule, a nitrogen oxide molecule ($N_2O$, NO, $NO_2$, or the like), and a copper atom is preferably used. Alternatively, it is preferable to use a conductive material having a function of inhibiting diffusion of oxygen (e.g., at least one of an oxygen atom, an oxygen molecule, and the like).

When a conductive material having a function of inhibiting oxygen diffusion is used for the first conductive layer of the conductive layer 1305, a reduction in the conductivity of the second conductive layer of the conductive layer 1305 due to oxidation can be inhibited. As a conductive material having a function of inhibiting oxygen diffusion, for example, tantalum, tantalum nitride, ruthenium, or ruthenium oxide is preferably used. Thus, the first conductive layer of the conductive layer 1305 preferably has a single-layer structure or a stacked-layer structure using any of the above conductive materials. For example, the first conductive layer of the conductive layer 1305 may be a stacked layer of a tantalum film, a tantalum nitride film, a ruthenium film, or a ruthenium oxide film and a titanium film or a titanium nitride film.

For the second conductive layer of the conductive layer 1305, a conductive material containing tungsten, copper, or aluminum as its main component is preferably used. Note that the second conductive layer of the conductive layer 1305 is a single layer in FIG. 13B and the like but may have a stacked-layer structure, for example, a stacked layer of a film containing the above conductive material and a titanium film or a titanium nitride film.

The insulating layer 1322 and the insulating layer 1324 function as gate insulating layers.

It is preferable that the insulating layer 1322 have a function of inhibiting diffusion of hydrogen (e.g., at least one of a hydrogen atom, a hydrogen molecule, and the like). In addition, it is preferable that the insulating layer 1322 have a function of inhibiting diffusion of oxygen (e.g., at least one of an oxygen atom, an oxygen molecule, and the like). For example, the insulating layer 1322 preferably has a function of inhibiting diffusion of one or both of hydrogen and oxygen more than the insulating layer 1324.

It is preferable to use an insulator containing an oxide of one or both of aluminum and hafnium, which is an insulating material, as a material of the insulating layer 1322. Aluminum oxide, hafnium oxide, an oxide containing aluminum and hafnium (hafnium aluminate), or the like is preferably used as the insulator. In the case where the insulating layer 1322 is formed using such a material, the insulating layer 1322 functions as a layer that inhibits release of oxygen from the oxide layer 1330 to the substrate side and diffusion of impurities such as hydrogen from the periphery of the transistor 1300 into the oxide layer 1330. Thus, providing the insulating layer 1322 can inhibit diffusion of impurities such as hydrogen into the transistor 1300 and inhibit generation of oxygen vacancies in the oxide layer 1330. Furthermore, the conductive layer 1305 can be inhibited from reacting with oxygen contained in the insulating layer 1324 and the oxide layer 1330.

Alternatively, aluminum oxide, bismuth oxide, germanium oxide, niobium oxide, silicon oxide, titanium oxide, tungsten oxide, yttrium oxide, or zirconium oxide may be added to the above insulator, for example. Alternatively, these insulators may be subjected to nitriding treatment. A layer in which a silicon oxide film, a silicon oxynitride film, or a silicon nitride film is stacked over an insulating film containing any of these insulators may be used as the insulating layer 1322.

The insulating layer 1322 may be formed to have a single-layer structure or a stacked-layer structure using an insulating material containing what is called a high-k material such as aluminum oxide, hafnium oxide, tantalum oxide, zirconium oxide, lead zirconate titanate (PZT), strontium titanate ($SrTiO_3$), or $(Ba,Sr)TiO_3$ (BST), for example. As miniaturization and high integration of transistors progress, a problem such as leakage current may arise because of a thinner gate insulating layer. When a high-k material is used for an insulating layer functioning as the gate insulating layer, a gate potential during operation of the transistor can be reduced while the physical thickness is maintained.

It is preferable that oxygen be released from the insulating layer 1324 in contact with the oxide layer 1330 by heating. A silicon oxide film, a silicon oxynitride film, or the like is used as appropriate for the insulating layer 1324, for example. When an insulating layer containing oxygen is provided in contact with the oxide layer 1330, oxygen vacancies in the oxide layer 1330 can be reduced and the reliability of the transistor 1300 can be improved.

For the insulating layer 1324, specifically, an oxide material from which part of oxygen is released by heating is preferably used. An oxide layer that releases oxygen by heating is an oxide layer in which the amount of released oxygen molecules is greater than or equal to $1.0 \times 10^{18}$ molecules/cm$^3$, preferably greater than or equal to $1.0 \times 10^{19}$ molecules/cm$^3$, further preferably greater than or equal to $2.0 \times 10^{19}$ molecules/cm$^3$ or greater than or equal to $3.0 \times 10^{20}$ molecules/cm$^3$ in TDS (Thermal Desorption Spectroscopy) analysis. Note that the temperature of the film surface in the TDS analysis is preferably higher than or equal to 100° C. and lower than or equal to 700° C., or higher than or equal to 100° C. and lower than or equal to 400° C.

The insulating layer 1324 preferably has a low hydrogen concentration and includes an excess-oxygen region or excess oxygen, and may be formed using a material similar to that for the insulating layer 1316, for example.

The insulating layer 1322 and the insulating layer 1324 may each have a stacked-layer structure of two or more layers. In that case, without limitation to a stacked-layer structure formed of the same material, a stacked-layer structure formed of different materials may be employed.

The oxide layer 1330 preferably has a stacked-layer structure using oxides with different chemical compositions. Specifically, the atomic ratio of the element M to metal elements of main components in the metal oxide used as the oxide layer 1330a is preferably greater than the atomic ratio of the element M to metal elements of main components in the metal oxide used as the oxide layer 1330b. Moreover, the atomic ratio of the element M to In in the metal oxide used as the oxide layer 1330a is preferably greater than the atomic ratio of the element M to In in the metal oxide used as the oxide layer 1330b. Furthermore, the atomic ratio of In to the element M in the metal oxide used as the oxide layer 1330b is preferably greater than the atomic ratio of In to the element M in the metal oxide used as the oxide layer 1330a. A metal oxide that can be used as the oxide layer 1330a or the oxide layer 1330b can be used as the oxide layer 1330c.

The oxide layer 1330b and the oxide layer 1330c preferably have crystallinity. For example, a CAAC-OS (c-axis aligned crystalline oxide semiconductor) is preferably used. An oxide having crystallinity, such as a CAAC-OS, has a dense structure with small amounts of impurities and defects (e.g., oxygen vacancies) and high crystallinity. This can inhibit oxygen extraction from the oxide layer 1330b by the source electrode or the drain electrode. This can reduce oxygen extraction from the oxide layer 1330b even when heat treatment is performed; hence, the transistor 1300 is stable with respect to high temperatures in the manufacturing process (what is called thermal budget).

A CAAC-OS is preferably used for the oxide layer 1330c; the c-axes of crystals included in the oxide layer 1330c are preferably aligned in a direction substantially perpendicular to the formation surface or the top surface of the oxide layer 1330c. The CAAC-OS has a property of making oxygen move easily in the direction perpendicular to the c-axis.

Thus, oxygen contained in the oxide layer 1330c can be efficiently supplied to the oxide layer 1330b.

The energy level of the conduction band minimum of each of the oxide layer 1330a and the oxide layer 1330c is preferably higher than the energy level of the conduction band minimum of the oxide layer 1330b. In other words, the electron affinity of each of the oxide layer 1330a and the oxide layer 1330c is preferably smaller than the electron affinity of the oxide layer 1330b. In that case, a metal oxide that can be used as the oxide layer 1330a is preferably used as the oxide layer 1330c. At this time, the oxide layer 1330b serves as a main carrier path.

Here, the energy level of the conduction band minimum is gradually varied at junction portions of the oxide layer 1330a, the oxide layer 1330b, and the oxide layer 1330c. In other words, the energy level of the conduction band minimum at the junction portions of the oxide layer 1330a, the oxide layer 1330b, and the oxide layer 1330c is continuously varied or continuously connected. To vary the energy level gradually, the density of defect states in a mixed layer formed at the interface between the oxide layer 1330a and the oxide layer 1330b and the interface between the oxide layer 1330b and the oxide layer 1330c is preferably made low.

Specifically, when the oxide layer 1330a and the oxide layer 1330b or the oxide layer 1330b and the oxide layer 1330c contain the same element as a main component in addition to oxygen, a mixed layer with a low density of defect states can be formed. For example, an In—Ga—Zn oxide, a Ga—Zn oxide, gallium oxide, or the like may be used for the oxide layer 1330a and the oxide layer 1330c in the case where the oxide layer 1330b is an In—Ga—Zn oxide.

Specifically, as the oxide layer 1330a, a metal oxide with In:Ga:Zn=1:3:4 [atomic ratio] or 1:1:0.5 [atomic ratio] is used. As the oxide layer 1330b, a metal oxide with In:Ga:Zn=1:1:1 [atomic ratio] or In:Ga:Zn=4:2:3 [atomic ratio] is used. As the oxide layer 1330c, a metal oxide with In:Ga:Zn=1:3:4 [atomic ratio], In:Ga:Zn=4:2:3 [atomic ratio], Ga:Zn=2:1 [atomic ratio], or Ga:Zn=2:5 [atomic ratio] is used.

When the metal oxide is deposited by a sputtering method, the atomic ratio is not limited to the atomic ratio of the deposited metal oxide and may be the atomic ratio of a sputtering target used for depositing the metal oxide.

When the oxide layer 1330a and the oxide layer 1330c have the above structure, the density of defect states at the interface between the oxide layer 1330a and the oxide layer 1330b and the interface between the oxide layer 1330b and the oxide layer 1330c can be made low. This reduces the influence of interface scattering on carrier conduction, and the transistor 1300 can have a high on-state current and high frequency characteristics.

The oxide layer 1330c may have a stacked-layer structure of two or more layers. For example, the oxide layer 1330c may include a first oxide layer and a second oxide over the first oxide layer.

The first oxide layer of the oxide layer 1330c preferably contains at least one of the metal elements contained in the metal oxide used as the oxide layer 1330b, and further preferably contains all of these metal elements. For example, it is preferable that an In—Ga—Zn oxide film be used as the first oxide layer of the oxide layer 1330c, and an In—Ga—Zn oxide film, a Ga—Zn oxide film, or a gallium oxide film be used as the second oxide layer of the oxide layer 1330c. Thus, the density of defect states at the interface between the oxide layer 1330b and the first oxide layer of the oxide layer 1330c can be decreased. The second oxide layer of the oxide layer 1330c preferably inhibits diffusion or transmission of oxygen more than the first oxide layer of the oxide layer 1330c. When the second oxide layer of the oxide layer 1330c is provided between the insulating layer 1350 and the first oxide layer of the oxide layer 1330c, diffusion of oxygen contained in the insulating layer 1380 into the insulating layer 1350 can be inhibited. Accordingly, the oxygen is more likely to be supplied to the oxide layer 1330b through the first oxide layer of the oxide layer 1330c.

The energy level of the conduction band minimum of each of the oxide layer 1330a and the second oxide layer of the oxide layer 1330c is preferably higher than the energy level of the conduction band minimum of each of the oxide layer 1330b and the first oxide layer of the oxide layer 1330c. In other words, the electron affinity of each of the oxide layer 1330a and the second oxide layer of the oxide layer 1330c is preferably smaller than the electron affinity of each of the oxide layer 1330b and the first oxide layer of the oxide layer 1330c. In that case, it is preferable that a metal oxide that can be used as the oxide layer 1330a be used as the second oxide layer of the oxide layer 1330c, and a metal oxide that can be used as the oxide layer 1330b be used as the first oxide layer of the oxide layer 1330c. At this time, not only the oxide layer 1330b but also the first oxide layer of the oxide layer 1330c serves as a main carrier path in some cases.

For the conductive layer 1342, $TaN_xO_y$ described above is preferably used. Note that $TaN_xO_y$ may contain aluminum. As another example, titanium nitride, a nitride containing titanium and aluminum, ruthenium oxide, ruthenium nitride, an oxide containing strontium and ruthenium, or an oxide containing lanthanum and nickel may be used. These materials are preferable because they are conductive materials that are not easily oxidized or materials that maintain the conductivity even when absorbing oxygen.

As illustrated in FIG. 13B, the insulating layer 1354 is preferably in contact with the top surface and the side surface of the conductive layer 1342a, the top surface and the side surface of the conductive layer 1342b, the side surfaces of the oxide layer 1330a and the oxide layer 1330b, and part of the top surface of the insulating layer 1324. With such a structure, the insulating layer 1380 is isolated from the insulating layer 1324, the oxide layer 1330a, and the oxide layer 1330b by the insulating layer 1354.

Like the insulating layer 1322, the insulating layer 1354 preferably has a function of inhibiting diffusion of one or both of hydrogen and oxygen. For example, the insulating layer 1354 preferably has a function of inhibiting diffusion of one or both of hydrogen and oxygen more than the insulating layer 1324 and the insulating layer 1380. Thus, diffusion of hydrogen contained in the insulating layer 1380 into the oxide layer 1330a and the oxide layer 1330b can be inhibited. Furthermore, by surrounding the insulating layer 1324, the oxide layer 1330, and the like with the insulating layer 1322 and the insulating layer 1354, diffusion of impurities such as water and hydrogen from the outside into the insulating layer 1324 and the oxide layer 1330 can be inhibited. Thus, the transistor 1300 can have favorable electrical characteristics and reliability.

An insulating film containing an oxide of one or both of aluminum and hafnium is preferably deposited as the insulating layer 1354, for example. In this case, the insulating layer 1354 is preferably deposited by an atomic layer deposition (ALD) method. An ALD method is a deposition method that provides good coverage, and thus can prevent formation of disconnection or the like due to unevenness of the insulating layer 1354.

An insulating film containing aluminum nitride is preferably used as the insulating layer 1354, for example. In that case, a film having an excellent insulating property and high thermal conductivity can be obtained, and thus dissipation of heat generated in driving the transistor 1300 can be increased. Alternatively, silicon nitride, silicon nitride oxide, or the like can be used.

An oxide containing gallium may be used for the insulating layer 1354, for example. An oxide containing gallium is preferable because it sometimes has a function of inhibiting diffusion of one or both of hydrogen and oxygen. Note that gallium oxide, gallium zinc oxide, indium gallium zinc oxide, or the like can be used as an oxide containing gallium. Note that when an indium gallium zinc oxide film is used as the insulating layer 1354, the atomic ratio of gallium to indium is preferably large. When the atomic ratio is increased, the insulating property of the oxide film can be high.

The insulating layer 1350 functions as a gate insulating layer. The insulating layer 1350 is preferably placed in contact with the top surface of the oxide layer 1330c. As a material of the insulating layer 1350, silicon oxide, silicon oxynitride, silicon nitride oxide, silicon nitride, silicon oxide to which fluorine is added, silicon oxide to which carbon is added, silicon oxide to which carbon and nitrogen are added, porous silicon oxide, or the like can be used. In particular, silicon oxide and silicon oxynitride, which have thermal stability, are preferable.

Like the insulating layer 1324, the insulating layer 1350 is preferably formed using an insulating film from which oxygen is released by heating. When an insulating film from which oxygen is released by heating is provided as the insulating layer 1350 in contact with the top surface of the oxide layer 1330c, oxygen can be effectively supplied to the channel formation region of the oxide layer 1330b and oxygen vacancies in the channel formation region of the oxide layer 1330b can be reduced. Accordingly, a transistor that has stable electrical characteristics with a small variation in electrical characteristics and improved reliability can be provided. Furthermore, as in the insulating layer 1324, the concentration of impurities such as water and hydrogen in the insulating layer 1350 is preferably reduced. The thickness of the insulating layer 1350 is preferably greater than or equal to 1 nm and less than or equal to 20 nm.

The conductive layer 1360 preferably includes the conductive layer 1360a and the conductive layer 1360b over the conductive layer 1360a. For example, the conductive layer 1360a is preferably placed so as to cover the bottom surface and side surface of the conductive layer 1360b.

For the conductive layer 1360a, a conductive material having a function of inhibiting diffusion of impurities such as a hydrogen atom, a hydrogen molecule, a water molecule, a nitrogen atom, a nitrogen molecule, a nitrogen oxide molecule, and a copper atom is preferably used. Alternatively, it is preferable to use a conductive material having a function of inhibiting diffusion of oxygen (e.g., at least one of an oxygen atom, an oxygen molecule, and the like).

When the conductive layer 1360a has a function of inhibiting diffusion of oxygen, it is possible to inhibit a reduction in conductivity of the conductive layer 1360b due to oxidation caused by oxygen contained in the insulating layer 1350. As a conductive material having a function of inhibiting diffusion of oxygen, for example, tantalum, tantalum nitride, ruthenium, or ruthenium oxide is preferably used.

The conductive layer 1360 also functions as a wiring and thus a conductive material having high conductivity is preferably used. For example, for the conductive layer 1360b, a conductive material containing tungsten, copper, or aluminum as its main component can be used. The conductive layer 1360b may have a stacked-layer structure, for example, a stacked-layer structure of a film containing any of the above conductive materials and a titanium film or a titanium nitride film.

Although the conductive layer 1360 has a two-layer structure of the conductive layer 1360a and the conductive layer 1360b in FIG. 13A and FIG. 13B, the conductive layer 1360 may have a single-layer structure or a stacked-layer structure of three or more layers.

In the transistor 1300, the conductive layer 1360 is formed in a self-aligned manner so as to fill an opening formed in the insulating layer 1380 and the like. Forming the conductive layer 1360 in this manner allows the conductive layer 1360 to be surely positioned in a region between the conductive layer 1342a and the conductive layer 1342b without alignment.

As illustrated in FIG. 13B, the top surface of the conductive layer 1360 is substantially aligned with the top surface of the insulating layer 1350 and the top surface of the oxide layer 1330c.

As illustrated in FIG. 13C, in the channel width direction of the transistor 1300, with reference to the bottom surface of the insulating layer 1322, the level of the bottom surface of the conductive layer 1360 in a region where the conductive layer 1360 and the oxide layer 1330b do not overlap with each other is preferably lower than the level of the bottom surface of the oxide layer 1330b. When the conductive layer 1360 functioning as the gate electrode covers the side surface and top surface of the channel formation region of the oxide layer 1330b with the insulating layer 1350 and the like therebetween, the electric field of the conductive layer 1360 is likely to affect the entire channel formation region of the oxide layer 1330b. Thus, the on-state current of the transistor 1300 can be increased and the frequency characteristics can be improved.

The insulating layer 1380 is provided over the insulating layer 1324, the oxide layer 1330, and the conductive layer 1342 with the insulating layer 1354 therebetween. The top surface of the insulating layer 1380 may be planarized.

The insulating layer 1380 functioning as an interlayer film preferably has a low dielectric constant. When a material having a low dielectric constant is used for an interlayer film, parasitic capacitance generated between wirings can be reduced. The insulating layer 1380 is preferably formed using a material similar to that for the insulating layer 1316, for example. Silicon oxide and silicon oxynitride are particularly preferable in terms of high thermal stability. Materials such as silicon oxide, silicon oxynitride, and porous silicon oxide, in each of which a region containing oxygen that is released by heating can be easily formed, are particularly preferable.

The concentration of impurities such as water and hydrogen in the insulating layer 1380 is preferably reduced. Moreover, the insulating layer 1380 preferably has a low hydrogen concentration and includes an excess-oxygen region or excess oxygen, and may be formed using a material similar to that for the insulating layer 1316, for example. Note that the insulating layer 1380 may have a stacked-layer structure of two or more layers.

Like the insulating layer 1314 and the like, the insulating layer 1374 preferably functions as an insulating barrier film that inhibits diffusion of impurities such as water and hydrogen into the insulating layer 1380 from above. In addition, like the insulating layer 1314 and the like, the insulating layer 1374 preferably has a low hydrogen concentration and has a function of inhibiting diffusion of hydrogen.

As illustrated in FIG. 13B, the insulating layer 1374 is preferably in contact with the top surfaces of the conductive layer 1360, the insulating layer 1350, and the oxide layer 1330c. In that case, impurities such as hydrogen contained in the insulating layer 1381 and the like can be inhibited from entering the insulating layer 1350. Thus, adverse effects on the electrical characteristics of the transistor and the reliability of the transistor can be inhibited.

The insulating layer 1381 functioning as an interlayer film is preferably provided over the insulating layer 1374. Like the insulating layer 1316 and the like, the insulating layer 1381 preferably has a low dielectric constant. As in the insulating layer 1324 and the like, the concentration of impurities such as water and hydrogen in the insulating layer 1381 is preferably reduced.

The conductive layer 1340a and the conductive layer 1340b are placed in openings formed in the insulating layer 1381, the insulating layer 1374, the insulating layer 1380, and the insulating layer 1354. The conductive layer 1340a and the conductive layer 1340b are provided to face each other with the conductive layer 1360 therebetween. Note that the top surfaces of the conductive layer 1340a and the conductive layer 1340b may be level with the top surface of the insulating layer 1381.

Note that the insulating layer 1341a is provided in contact with a side wall of the opening in the insulating layer 1381, the insulating layer 1374, the insulating layer 1380, and the insulating layer 1354, and the conductive layer 1340a is formed in contact with the side surface of the insulating layer 1341a. The conductive layer 1342a is located on at least part of the bottom portion of the opening, and the conductive layer 1340a is in contact with the conductive layer 1342a. Similarly, the insulating layer 1341b is provided in contact with a side wall of the opening in the insulating layer 1381, the insulating layer 1374, the insulating layer 1380, and the insulating layer 1354, and the conductive layer 1340b is formed in contact with the side surface of the insulating layer 1341b. The conductive layer 1342b is located on at least part of the bottom portion of the opening, and the conductive layer 1340b is in contact with the conductive layer 1342b.

For the conductive layer 1340a and the conductive layer 1340b, a conductive material containing tungsten, copper, or aluminum as its main component is preferably used.

The conductive layer 1340a and the conductive layer 1340b may have a stacked-layer structure. Although the conductive layer 1340a and the conductive layer 1340b have a stacked-layer structure of two layers in the transistor 1300, the present invention is not limited thereto. The conductive layer 1340 may have a single-layer structure or a stacked-layer structure of three or more layers, for example.

As the insulating layer 1341a and the insulating layer 1341b, an insulating film that can be used as the insulating layer 1314, the insulating layer 1354, or the like can be used, for example. Since the insulating layer 1341a and the insulating layer 1341b are provided in contact with the insulating layer 1354, impurities such as water and hydrogen contained in the insulating layer 1380 and the like can be inhibited from diffusing into the oxide layer 1330 through the conductive layer 1340a and the conductive layer 1340b. In addition, oxygen contained in the insulating layer 1380 can be prevented from being absorbed by the conductive layer 1340a and the conductive layer 1340b.

Although not illustrated, a conductive layer functioning as a wiring may be provided in contact with the top surface of the conductive layer 1340a and the top surface of the conductive layer 1340b. For the conductive layer functioning as a wiring, a conductive material containing tungsten, copper, or aluminum as its main component is preferably used. Furthermore, the conductive layer may have a stacked-layer structure, for example, a stack of a titanium film or a titanium nitride film and a film containing the above conductive material. Note that the conductive layer may be formed to be embedded in an opening provided in an insulating layer.

Although not illustrated, an insulating layer having a resistivity higher than or equal to $1.0 \times 10^{13}$ Ωcm and lower than or equal to $1.0 \times 10^{15}$ Ωcm, preferably higher than or equal to $5.0 \times 10^{13}$ Ωcm and lower than or equal to $5.0 \times 10^{14}$ Ωcm is preferably provided to cover the conductive layer. It is preferable that an insulating layer having a resistivity in the above range be provided over the conductive layer, in which case the insulating layer can disperse electric charge accumulated in the transistor 1300 or between wirings of the conductive layer and the like and can inhibit defects in characteristics and electrostatic breakdown of the transistor and an electronic device including the transistor due to the electric charge, while maintaining the insulating property.

The size of the transistors described in this embodiment can be reduced, which facilitates an increase in the resolution and the application to a relatively small electronic device.

This embodiment can be combined with the other embodiments as appropriate. In this specification, in the case where a plurality of structure examples are shown in one embodiment, the structure examples can be combined as appropriate.

Embodiment 3

In this embodiment, a semiconductor device using the counter circuit that includes the latch circuit described in Embodiment 1 will be described. First, an example will be described in which the outputs of the ternary counter circuit shown in FIG. 2, the senary counter circuit shown in FIG. 3, and the decade counter circuit shown in FIG. 5 are used for a watch. Next, an example will be described in which the outputs of the ternary counter circuit, the senary counter circuit, and the decade counter circuit are used for a battery protection IC.

Figure 15:
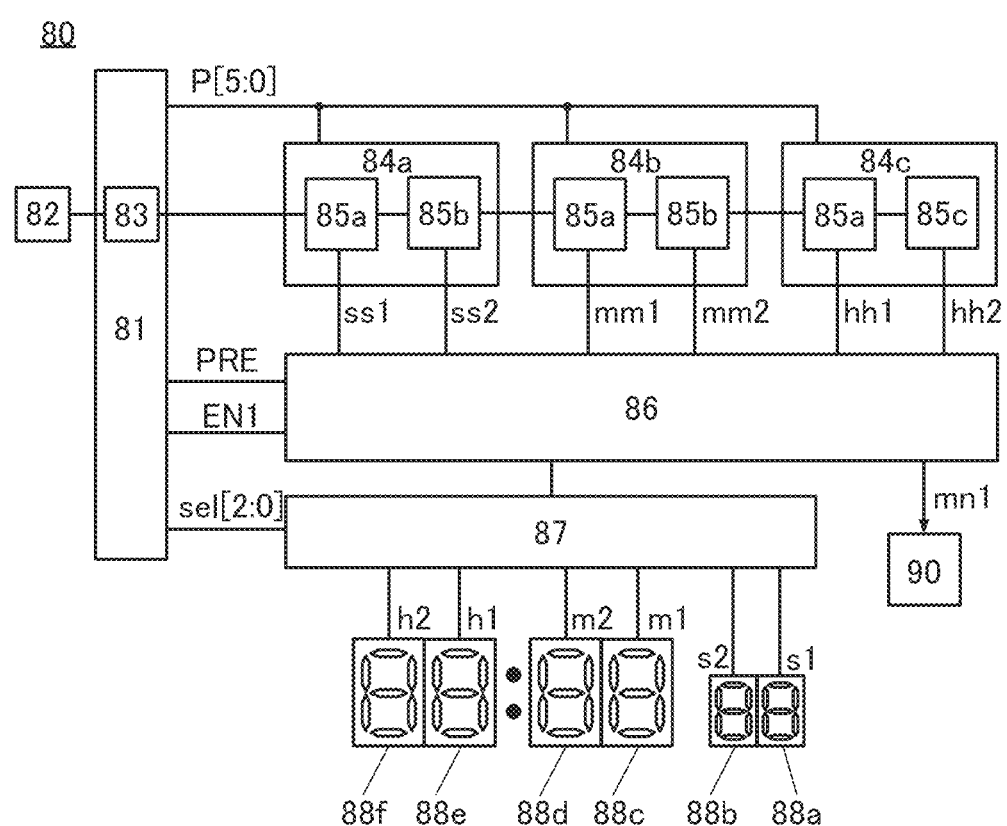
FIG. 15 is a block diagram illustrating a semiconductor device.

FIG. 15 is a block diagram illustrating a semiconductor device 80. The semiconductor device 80 includes a control circuit 81, an oscillator 82, a frequency divider 83, a circuit 84a, a circuit 84b, a circuit 84c, a decoder circuit 86, a selector circuit 87, and display devices 88a to 88f In addition, the semiconductor device 80 includes a battery protection IC 90. The circuit 84a includes a decade counter circuit 85a and a senary counter circuit 85b. The circuit 84b includes the decade counter circuit 85a and the senary counter circuit 85b. The circuit 84c includes the decade counter circuit 85a and a ternary counter circuit 85c.

The oscillator 82 is electrically connected to the frequency divider 83. The frequency divider 83 is electrically connected to the decade counter circuit 85a included in the circuit 84. Note that the frequency divider 83 may be included in the control circuit 81 as illustrated in FIG. 15. The control circuit 81 is electrically connected to the circuit 84a, the circuit 84b, the circuit 84c, the decoder circuit 86, and the selector circuit 87. The circuit 84a is electrically connected to the decoder circuit 86. The circuit 84b is electrically connected to the decoder circuit 86. The circuit 84*c* is electrically connected to the decoder circuit 86. The decoder circuit 86 is electrically connected to the selector circuit 87. The selector circuit 87 is electrically connected to each of the display devices 88*a* to 88*f*.

The control circuit 81 may include the frequency divider 83. The control circuit 81 including the frequency divider 83 can easily generate the clock signals P0 to P5. In addition, a signal PRE and a signal EN1 supplied to the decoder circuit 86 and selection signals sel0 to sel2 can be easily generated.

The decade counter circuit 85*a* included in the circuit 84*a* outputs a signal ss1 to the decoder circuit 86. The senary counter circuit 85*b* included in the circuit 84*a* outputs a signal ss2 to the decoder circuit 86. The decade counter circuit 85*a* included in the circuit 84*b* outputs a signal mm1 to the decoder circuit 86. The senary counter circuit 85*b* included in the circuit 84*b* outputs a signal mm2 to the decoder circuit 86. The decade counter circuit 85*a* included in the circuit 84*c* outputs a signal hh1 to the decoder circuit 86. The ternary counter circuit 85*c* included in the circuit 84*c* outputs a signal hh2 to the decoder circuit 86.

The decoder circuit 86 is preferably composed of a dynamic circuit. The signal PRE supplies the timing of precharge in the dynamic circuit. The signal EN1 is a signal for selecting the output of one of the circuit 84*a*, the circuit 84*b*, and the circuit 84*c*. Contents to be displayed on the display devices 88*a* to 88*f* can be selected with the selection signals sel0 to sel2. The display devices 88*a* to 88*f* each include first to seventh segments, for example. By turning on a plurality of segments among the first to seventh segments, numbers from 0 to 9 can be displayed.

Thus, a signal s1 is supplied to the display device 88*a*, and the first digit of seconds (second) is displayed. A signal s2 is supplied to the display device 88*b*, and the second digit of seconds (second) is displayed. A signal m1 is supplied to the display device 88*c*, and the first digit of minutes (minute) is displayed. A signal m2 is supplied to the display device 88*d*, and the second digit of minutes (minute) is displayed. A signal h1 is supplied to the display device 88*e*, and the first digit of hours (hour) is displayed. A signal h2 is supplied to the display device 88*f*, and the second digit of hours (hour) is displayed. Accordingly, the semiconductor device 80 functions as a watch.

The decoder circuit 86 can output a signal mn1 to the battery protection IC 90.

Next, the battery protection IC 90 will be described. The battery protection IC 90 includes a battery and a detecting circuit. Note that the battery protection IC 90 can be rephrased as a detecting device. The battery protection IC 90 includes a detecting circuit that detects a failure mode of the battery in addition to the one that manages a power supply voltage. For example, a failure called micro short-circuit (also referred to as internal short-circuit or soft short-circuit) is generated in a lithium-ion battery. The micro short-circuit is a failure mode where lithium metal that precipitates on a negative electrode reaches a positive electrode; eventually short-circuit occurs between the negative electrode and the positive electrode and a battery voltage slightly decreases. The signal mn1 supplied from the decoder circuit 86 to the battery protection IC 90 can be used as a monitor cycle for monitoring the failure mode.

Note that in this specification and the like, the battery protection IC 90 using the latch circuit or the counter circuit is referred to as BTOS (Battery operating system or Battery oxide semiconductor). The BTOS includes an OS transistor.

In this embodiment, the battery protection IC 90 will be described with reference to FIG. 16. A micro short-circuit detecting circuit (Micro-short detector) included in the battery protection IC 90 is formed using an N-type transistor. Note that in the micro short-circuit detecting circuit, a transistor including a metal oxide in a semiconductor layer can be used.

Figure 16A:
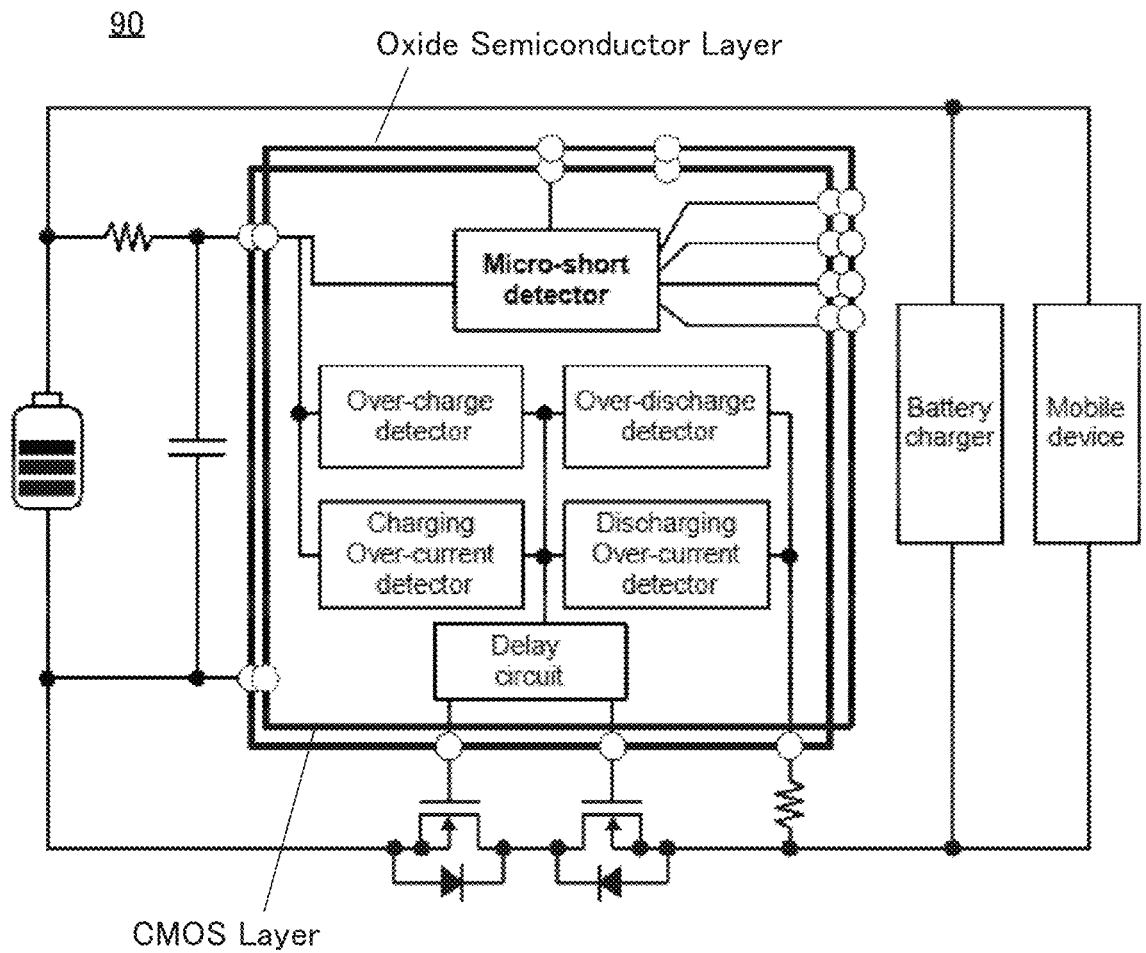
FIG. 16A is a block diagram of a battery protection IC.

FIG. 16A is a block diagram illustrating the battery protection IC 90, a charger (Battery charger), and a control portion (Mobile device). The battery protection IC 90 may include the charger and the control portion as its components, for example. The battery protection IC is composed of a circuit formed by a CMOS process (CMOS Layer) and a circuit that detects micro short-circuit and is formed using a transistor including a metal oxide in a semiconductor layer (Oxide Semiconductor Layer). The battery protection IC includes the micro short-circuit detecting circuit (Micro-short detector); an overcharge detecting circuit (Over-charge detector), an overdischarge detecting circuit (Over-discharge detector), overcurrent detecting circuits (Charging Over-current detector and DisCharging Over-current detector), and a delay circuit (Delay circuit) for managing the power supply voltage; and the like. The signal mn1 is supplied to the micro short-circuit detecting circuit or the delay circuit.

Figure 16B:
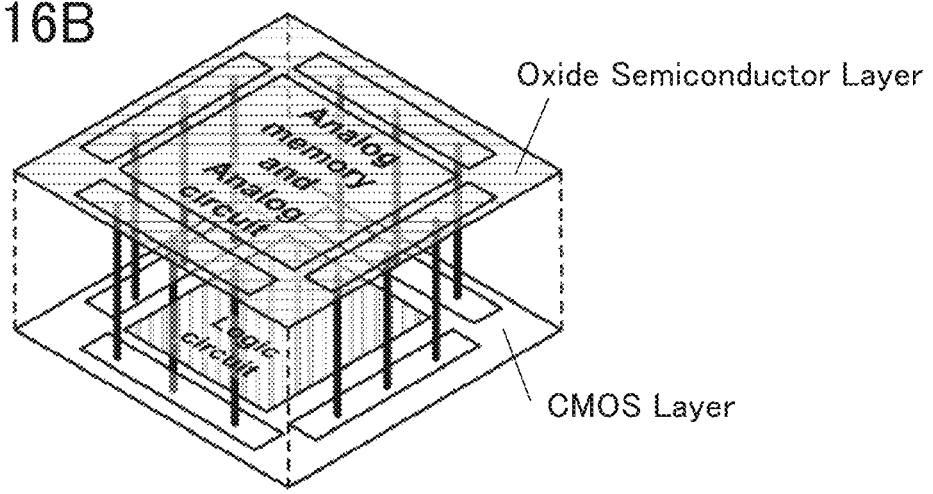
FIG. 16B is a perspective view of a battery protection IC.

FIG. 16B is a perspective view in which a circuit formed by the CMOS process (Logic circuit) and the circuit that detects micro short-circuit and is formed using a transistor including a metal oxide in a semiconductor layer (Analog memory and Analog circuit) are stacked. An example is illustrated in which the overcharge detecting circuit, the overdischarge detecting circuit, the overcurrent detecting circuit, the delay circuit, and the like for managing the power supply voltage are formed by the CMOS process. The micro short-circuit detecting circuit can be provided to be stacked over the circuit that is formed by the CMOS process and manages the power supply voltage. The micro short-circuit detecting circuit can be formed using only an N-type transistor, so that the layout area can be reduced. When the micro short-circuit detecting circuit and another circuit are stacked, a wiring can be made short. Note that in the CMOS process, single crystal silicon, polycrystalline silicon, microcrystalline silicon, or the like is preferably used. In particular, polycrystalline silicon can be formed at a lower temperature than single crystal silicon and has higher field-effect mobility and higher reliability than amorphous silicon.

The watch using the counter circuit using the dynamic circuit described in Embodiment 1 and the micro short-circuit detecting circuit can be formed using only the same N-type transistor, which can simplify the manufacturing process. Moreover, using an OS transistor reduces the off-state current, which can reduce power consumption.

This embodiment can be implemented in combination with any of the structures described in the other embodiments and the like, as appropriate.

Embodiment 4

In this embodiment, a metal oxide that can be suitably used for a channel formation region of a transistor will be described.

As a semiconductor material used for a transistor, a metal oxide whose energy gap is greater than or equal to 2 eV, preferably greater than or equal to 2.5 eV, further preferably greater than or equal to 3 eV can be used. A typical example is a metal oxide containing indium, and a CAC-OS described later or the like can be used, for example.

A transistor using a metal oxide having a wider band gap and a lower carrier density than silicon has a low off-state current; thus, charges accumulated in a capacitor that is series-connected to the transistor can be held for a long time.

A semiconductor layer can be, for example, a film represented by an In-M-Zn-based oxide that contains indium, zinc, and M (a metal such as aluminum, titanium, gallium, germanium, yttrium, zirconium, lanthanum, cerium, tin, neodymium, or hafnium).

In the case where a metal that constitutes the semiconductor layer is an In-M-Zn-based oxide, it is preferable that the atomic ratio of metal elements in a sputtering target used to deposit an In-M-Zn oxide satisfy In≥M and Zn≥M. The atomic ratio of metal elements of such a sputtering target is preferably In:M:Zn=1:1:1, In:M:Zn=1:1:1.2, In:M:Zn=3:1:2, In:M:Zn=4:2:3, InM:Zn=4:2:4.1, In:M:Zn=5:1:6, In:M:Zn=5:1:7, In:M:Zn=5:1:8, or the like. Note that the atomic ratio in the deposited semiconductor layer varies from the atomic ratio of metal elements in the sputtering target in a range of ±40%.

A metal oxide film with a low carrier density is used for the semiconductor layer. For example, for the semiconductor layer, a metal oxide whose carrier density is lower than or equal to $1\times10^{17}/cm^3$, preferably lower than or equal to $1\times10^{15}/cm^3$, further preferably lower than or equal to $1\times10^{13}/cm^3$, still further preferably lower than or equal to $1\times10^{11}/cm^3$, even further preferably lower than $1\times10^{10}/cm^3$, and higher than or equal to $1\times10^{9}/cm^3$ can be used. Such a metal oxide is referred to as a highly purified intrinsic or substantially highly purified intrinsic metal oxide. The oxide semiconductor has a low density of defect states and can be regarded as a metal oxide having stable characteristics.

Note that the composition is not limited to those, and an oxide semiconductor having an appropriate composition may be used depending on required semiconductor characteristics and electrical characteristics (field-effect mobility, threshold voltage, or the like) of the transistor. In addition, to obtain the required semiconductor characteristics of the transistor, it is preferable that the carrier density, impurity concentration, defect density, atomic ratio between a metal element and oxygen, interatomic distance, density, and the like of the semiconductor layer be set to be appropriate.

When silicon or carbon, which is one of the Group 14 elements, is contained in the metal oxide that constitutes the semiconductor layer, oxygen vacancies in the semiconductor layer are increased, and the semiconductor layer becomes n-type. Thus, the concentration of silicon or carbon (concentration obtained by secondary ion mass spectrometry) in the semiconductor layer is set to lower than or equal to $2\times10^{18}$ atoms/cm$^3$, preferably lower than or equal to $2\times10^{17}$ atoms/cm$^3$.

Alkali metal and alkaline earth metal might generate carriers when bonded to a metal oxide, in which case the off-state current of the transistor might be increased. Thus, the concentration of alkali metal or alkaline earth metal in the semiconductor layer, which is obtained by secondary ion mass spectrometry, is set to lower than or equal to $1\times10^{18}$ atoms/cm$^3$, preferably lower than or equal to $2\times10^{16}$ atoms/cm$^3$.

When nitrogen is contained in the metal oxide that constitutes the semiconductor layer, electrons serving as carriers are generated and the carrier density is increased, so that the semiconductor layer easily becomes n-type. As a result, a transistor using a metal oxide that contains nitrogen is likely to have normally-on characteristics. Therefore, the concentration of nitrogen in the semiconductor layer, which is obtained by secondary ion mass spectrometry, is preferably set to lower than or equal to $5\times10^{18}$ atoms/cm$^3$.

Oxide semiconductors are classified into a single crystal oxide semiconductor and a non-single-crystal oxide semiconductor. Examples of a non-single-crystal oxide semiconductor include a CAAC-OS (c-axis-aligned crystalline oxide semiconductor), a polycrystalline oxide semiconductor, an nc-OS (nanocrystalline oxide semiconductor), an amorphous-like oxide semiconductor (a-like OS), and an amorphous oxide semiconductor.

A CAC-OS (Cloud-Aligned Composite oxide semiconductor) may be used for a semiconductor layer of a transistor disclosed in one embodiment of the present invention.

Note that the aforementioned non-single-crystal oxide semiconductor or CAC-OS can be suitably used for a semiconductor layer of a transistor disclosed in one embodiment of the present invention. As the non-single-crystal oxide semiconductor, the nc-OS or the CAAC-OS can be suitably used.

Note that in one embodiment of the present invention, a CAC-OS is preferably used for a semiconductor layer of a transistor. The use of the CAC-OS allows the transistor to have high electrical characteristics or high reliability.

Note that the semiconductor layer may be a mixed film including two or more kinds of a region of a CAAC-OS, a region of a polycrystalline oxide semiconductor, a region of an nc-OS, a region of an amorphous-like oxide semiconductor, and a region of an amorphous oxide semiconductor. The mixed film has, for example, a single-layer structure or a stacked-layer structure including two or more kinds of the above regions in some cases.

The composition of a CAC (Cloud-Aligned Composite)-OS that can be used in a transistor disclosed in one embodiment of the present invention will be described below.

The CAC-OS has, for example, a composition in which elements included in a metal oxide are unevenly distributed. Materials including unevenly distributed elements each have a size greater than or equal to 0.5 nm and less than or equal to 10 nm, preferably greater than or equal to 1 nm and less than or equal to 2 nm, or a similar size. Note that in the following description of a metal oxide, a state in which one or more metal elements are unevenly distributed and regions including the metal element(s) are mixed is referred to as a mosaic pattern or a patch-like pattern. The regions each have a size greater than or equal to 0.5 nm and less than or equal to 10 nm, preferably greater than or equal to 1 nm and less than or equal to 2 nm, or a similar size.

Note that the metal oxide preferably contains at least indium. In particular, indium and zinc are preferably contained. Moreover, in addition to these, one or more kinds selected from aluminum, gallium, yttrium, copper, vanadium, beryllium, boron, silicon, titanium, iron, nickel, germanium, zirconium, molybdenum, lanthanum, cerium, neodymium, hafnium, tantalum, tungsten, magnesium, and the like may be contained.

For example, a CAC-OS in an In—Ga—Zn oxide (an In—Ga—Zn oxide in the CAC-OS may be particularly referred to as CAC-IGZO) has a composition in which materials are separated into indium oxide (hereinafter, referred to as $InO_{X1}$ (X1 is a real number greater than 0)) or indium zinc oxide (hereinafter, referred to as $In_{X2}Zn_{Y2}O_{Z2}$ (each of X2, Y2, and Z2 is a real number greater than 0)) and gallium oxide (hereinafter, referred to as $GaO_{X3}$ (X3 is a real number greater than 0)) or gallium zinc oxide (hereinafter, referred to as $Ga_{X4}Zn_{Y4}O_{Z4}$ (each of X4, Y4, and Z4 is a real number greater than 0)), for example, so that a mosaic pattern is formed, and mosaic-like $InO_{X1}$ or $In_{X2}Zn_{Y2}O_{Z2}$ is evenly distributed in the film (this composition is hereinafter also referred to as a cloud-like composition).

That is, the CAC-OS is a composite metal oxide having a composition in which a region where $GaO_{X3}$ is a main component and a region where $In_{X2}Zn_{Y2}O_{Z2}$ or $InO_{X1}$ is a main component are mixed. Note that in this specification, for example, when the atomic ratio of In to an element M in a first region is greater than the atomic ratio of In to the element M in a second region, the first region is regarded as having a higher In concentration than the second region.

Note that IGZO is a common name and sometimes refers to one compound formed of In, Ga, Zn, and O. A typical example is a crystalline compound represented by $InGaO_3(ZnO)_{m1}$ (m1 is a natural number) or $In_{(1+x0)}Ga_{(1-x0)}O_3(ZnO)_{m0}$ (−1≤x0≤1; m0 is a given number).

The crystalline compound has a single crystal structure, a polycrystalline structure, or a CAAC structure. Note that the CAAC structure is a crystal structure in which a plurality of IGZO nanocrystals have c-axis alignment and are connected in the a-b plane without alignment.

Meanwhile, the CAC-OS relates to the material composition of a metal oxide. In the material composition of a CAC-OS containing In, Ga, Zn, and O, some regions that contain Ga as a main component and are observed as nanoparticles and some regions that contain In as a main component and are observed as nanoparticles are randomly dispersed in a mosaic pattern. Thus, the crystal structure is a secondary element for the CAC-OS.

Note that the CAC-OS is regarded as not including a stacked-layer structure of two or more kinds of films with different compositions. For example, a two-layer structure of a film containing In as a main component and a film containing Ga as a main component is not included.

Note that a clear boundary between the region where $GaO_{X3}$ is a main component and the region where $In_{X2}Zn_{Y2}O_{Z2}$ or $InO_{X1}$ is a main component cannot be observed in some cases.

Note that in the case where one or more kinds selected from aluminum, yttrium, copper, vanadium, beryllium, boron, silicon, titanium, iron, nickel, germanium, zirconium, molybdenum, lanthanum, cerium, neodymium, hafnium, tantalum, tungsten, magnesium, and the like are contained instead of gallium, the CAC-OS refers to a composition in which some regions that contain the metal element(s) as a main component and are observed as nanoparticles and some regions that contain In as a main component and are observed as nanoparticles are randomly dispersed in a mosaic pattern.

The CAC-OS can be formed by a sputtering method under a condition where a substrate is not heated, for example. In the case of forming the CAC-OS by a sputtering method, one or more selected from an inert gas (typically, argon), an oxygen gas, and a nitrogen gas may be used as a deposition gas. The ratio of the flow rate of the oxygen gas to the total flow rate of the deposition gas at the time of deposition is preferably as low as possible, and for example, the ratio of the flow rate of the oxygen gas is preferably higher than or equal to 0% and lower than 30%, further preferably higher than or equal to 0% and lower than or equal to 10%.

The CAC-OS is characterized in that no clear peak is observed at the time of measurement using θ/2θ scan by an Out-of-plane method, which is one of X-ray diffraction (XRD) measurement methods. That is, it is found from the X-ray diffraction measurement that no alignment in the a-b plane direction and the c-axis direction is observed in the measured region.

In an electron diffraction pattern of the CAC-OS that is obtained by irradiation with an electron beam with a probe diameter of 1 nm (also referred to as a nanobeam electron beam), a ring-like high-luminance region (ring region) and a plurality of bright spots in the ring region are observed. It is thus found from the electron diffraction pattern that the crystal structure of the CAC-OS includes an nc (nanocrystal) structure with no alignment in the plan-view direction and the cross-sectional direction.

Moreover, for example, it can be confirmed by EDX mapping obtained using energy dispersive X-ray spectroscopy (EDX) that the CAC-OS in the In—Ga—Zn oxide has a composition in which regions where $GaO_{X3}$ is a main component and regions where $In_{X2}Zn_{Y2}O_{Z2}$ or $InO_{X1}$ is a main component are unevenly distributed and mixed.

The CAC-OS has a composition different from that of an IGZO compound in which metal elements are evenly distributed, and has characteristics different from those of the IGZO compound. That is, the CAC-OS has a composition in which regions where $GaO_{X3}$ or the like is a main component and regions where $In_{X2}Zn_{Y2}O_{Z2}$ or $InO_{X1}$ is a main component are phase-separated from each other and form a mosaic pattern.

Here, a region where $In_{X2}Zn_{Y2}O_{Z2}$ or $InO_{X1}$ is a main component is a region whose conductivity is higher than that of a region where $GaO_{X3}$ or the like is a main component. In other words, when carriers flow through regions where $In_{X2}Zn_{Y2}O_{Z2}$ or $InO_{X1}$ is a main component, the conductivity of a metal oxide is exhibited. Accordingly, when the regions where $In_{X2}Zn_{Y2}O_{Z2}$ or $InO_{X1}$ is a main component are distributed like a cloud in a metal oxide, high field-effect mobility (μ) can be achieved.

By contrast, a region where $GaO_{X3}$ or the like is a main component is a region whose insulating property is higher than that of a region where $In_{X2}Zn_{Y2}O_{Z2}$ or $InO_{X1}$ is a main component. In other words, when regions where $GaO_{X3}$ or the like is a main component are distributed in a metal oxide, leakage current can be suppressed and favorable switching operation can be achieved.

Accordingly, when the CAC-OS is used for a semiconductor element, the insulating property derived from $GaO_{X3}$ or the like and the conductivity derived from $In_{X2}Zn_{Y2}O_{Z2}$ or $InO_{X1}$ complement each other, so that a high on-state current (Ion) and high field-effect mobility (μ) can be achieved.

A semiconductor element using the CAC-OS has high reliability. Thus, the CAC-OS is suitable for a variety of semiconductor devices typified by a display.

Since a transistor including the CAC-OS in a semiconductor layer has high field-effect mobility and high driving capability, the use of the transistor in a driver circuit, a typical example of which is a scan line driver circuit that generates a gate signal, can provide a display device with a narrow frame width (also referred to as a narrow bezel). Furthermore, the use of the transistor in a signal line driver circuit that is included in a display device (particularly in a demultiplexer connected to a terminal of a shift register included in a signal line driver circuit) can reduce the number of wirings connected to the display device.

Furthermore, unlike a transistor using low-temperature polysilicon, the transistor including the CAC-OS in the semiconductor layer does not need a laser crystallization step. Thus, the manufacturing cost of a display device can be reduced even when the display device is formed using a large substrate. In addition, the transistor including the CAC-OS in the semiconductor layer is preferably used for a driver circuit and a display portion in a large display device having high resolution such as ultra-high definition ("4K resolution", "41(2K", and "4K") or super high definition ("8K resolution", "8K4K", and "8K"), in which case writing can be performed in a short time and display defects can be reduced.

Alternatively, silicon may be used for a semiconductor in which a channel of a transistor is formed. Although amorphous silicon may be used as silicon, silicon having crystallinity is particularly preferably used. For example, microcrystalline silicon, polycrystalline silicon, single crystal silicon, or the like is preferably used. In particular, polycrystalline silicon can be formed at a lower temperature than single crystal silicon and has higher field-effect mobility and higher reliability than amorphous silicon.

At least part of this embodiment can be implemented in combination with the other embodiments described in this specification as appropriate.

Embodiment 5

In this embodiment, examples of an electronic device in which the semiconductor device of one embodiment of the present invention can be used will be described.

Figure 17A:
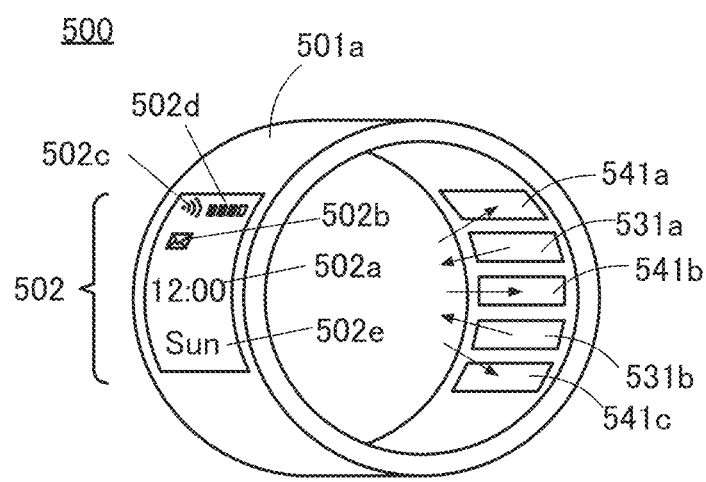
FIG. 17A and FIG. 17B are diagrams illustrating an electronic device.

FIG. 17A illustrates an electronic device 500 using the semiconductor device described in Embodiment 1 or Embodiment 3.

The electronic device 500 includes the semiconductor device 80 (not illustrated), the battery protection IC 90 (not illustrated), a processor (not illustrated), a memory (not illustrated), a battery (not illustrated), an image processing circuit (not illustrated), a communication module (not illustrated), a sensor device, and the like.

The electronic device 500 includes a portable terminal 502. The portable terminal has a watch 502a, sending and receiving an e-mail 502b, a communication function 502c, battery management 502d, a calendar 502e, a calling function, and the like. The portable terminal is arranged on the outer side of the electronic device 500, and the sensor device is arranged on the inner surface of the electronic device 500.

The sensor device includes light-emitting regions (531a and 531b) and sensor regions (541a, 541b, and 541c). The light-emitting regions (531a and 531b) can emit lights with different peak wavelengths. The sensor regions (541a, 541b, and 541c) include peak wavelengths of lights emitted from the light-emitting regions in their sensing ranges; thus, lights with different peak wavelengths can be sensed at the same time.

Figure 17B:
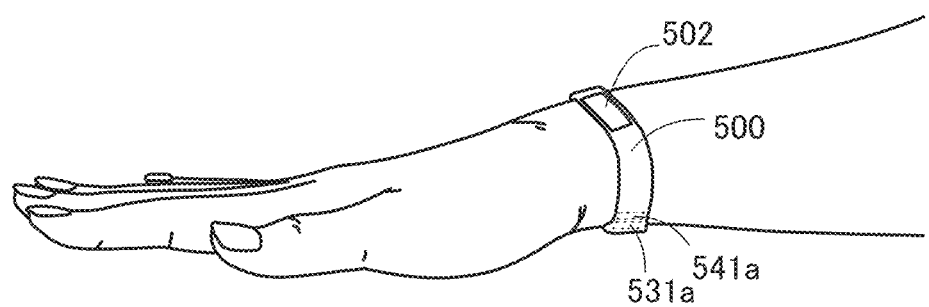

FIG. 17B is a diagram of the electronic device 500 put on a wrist, for example. The sensor device is arranged inside; thus, the sensor device functions as a physiological monitor. For example, the blood sugar level can be monitored by sensing the amount of glucose in the blood. The signal mn1 generated by the semiconductor device 80 can set the monitor cycle for sensing the blood sugar level. The sensed amount of glucose is stored in a memory of the portable terminal as data, and a change in the amount of glucose in the blood through a day can be monitored. By monitoring the change in the amount of glucose in the blood, the electronic device 500 can inform a diabetic of administration timing of insulin or the like by vibration, display, lighting, or the like. The data can be transmitted to a server or the like by the communication function 502c. Note that the monitoring target is not limited to glucose. For example, the amount of hemoglobin can be sensed. For another example, a change in body temperature can be sensed. Since the semiconductor device 80 is composed of the dynamic circuit and thus has low power consumption, data of a long period of time can be obtained.

Figure 18A:
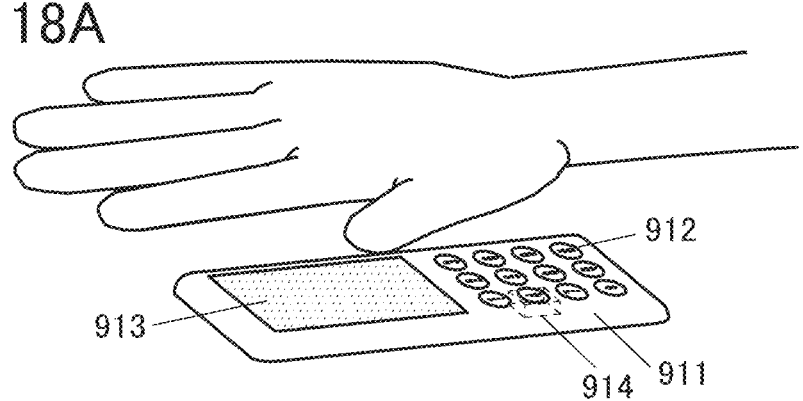
FIG. 18A to FIG. 18C are diagrams illustrating electronic devices.

FIG. 18A is a biometric authentication device including a thin housing 911, operation buttons 912, a sensor device 913, and the like. By holding the hand or finger over the sensor device 913 or touching the sensor device 913 with the hand or finger, the shape of the vein can be identified. The signal mn1 generated by the semiconductor device 80 can set the monitor cycle for sensing a change in the shape of the vein over time. The obtained data is transmitted to a server by a wireless communication unit 914 and compared with a database, so that personal identification is possible. Furthermore, a security code or the like can be input with the operation buttons. With the sensor device 913 of one embodiment of the present invention, a thin authentication device including a light-emitting region and a sensor region can be formed. The small thickness facilitates the incorporation into various devices. In addition, the portability is improved.

Figure 18B:
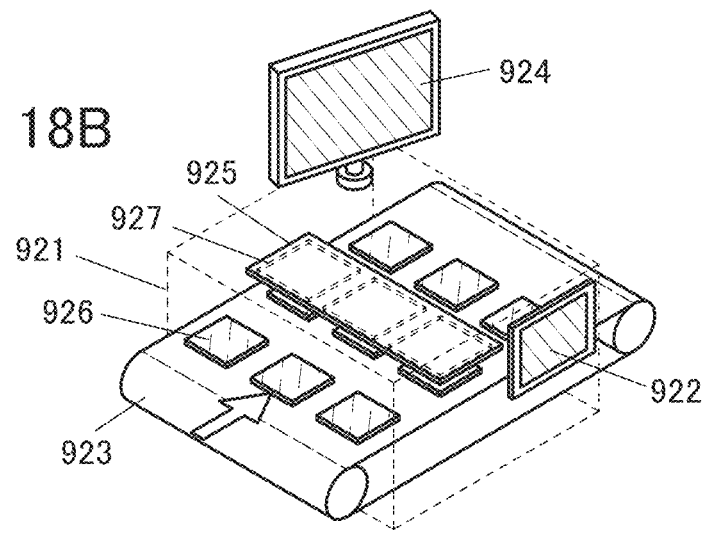

FIG. 18B is a non-destructive testing device including a housing 921, an operation panel 922, a transfer mechanism 923, a monitor 924, a detecting unit 925, and the like. The detecting unit 925 includes a sensor device. Testing target members 926 are transported to the position directly under the detecting unit 925 by the transfer mechanism 923. A sensor device 927 of one embodiment of the present invention provided in the detecting unit 925 performs image capturing on the testing target members 926, and the captured image is displayed on the monitor 924. Note that the signal mn1 generated by the semiconductor device 80 preferably drives the transfer mechanism 923 and the sensor device 927 in synchronization with each other. After that, the testing target members 926 are transported to an exit of the housing 921 and a defective member is separately collected. Image capturing using near-infrared light enables non-destructive and high-speed sensing of defective elements inside the testing target members, such as defects and foreign substances. A light-emitting region and a sensor region are included in the sensor device 927 of one embodiment of the present invention; thus, the detecting unit 925 can be formed at low costs.

Figure 18C:
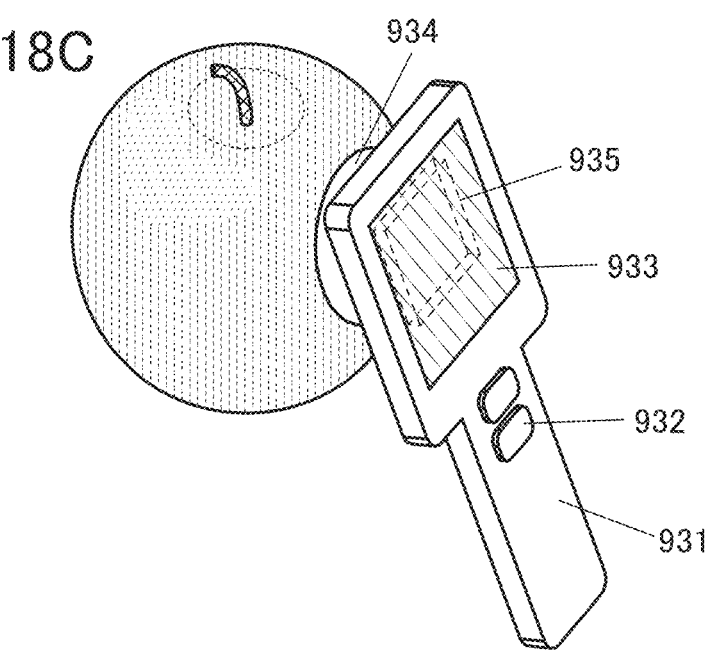

FIG. 18C is a food-sorting device including a housing 931, operation buttons 932, a display portion 933, a light-blocking hood 934, and the like. The light-blocking hood 934 provided in the periphery of the light-receiving portion is brought into intimate contact with a food of the testing target, such as a fruit, and image capturing is performed; thus, a foreign substance mixed into the food, a bug, a cavity or spoilage inside the food, and the like can be detected. Furthermore, the sugar content, moisture content, or the like of foods can also be determined from the intensity of the detected near-infrared light. The food-sorting device can sort out defectives, classify foods according to the grade, and determine the harvest time. Note that the wavelength differs between the near-infrared light suitable for determining the sugar content and the near-infrared light suitable for determining the moisture content; thus, the near-infrared lights with a plurality of wavelengths are preferably used. The signal mn1 generated by the semiconductor device 80 preferably manages the lighting time of the plurality of near-infrared lights. A sensor device 935 of one embodiment of the present invention provided in the light-receiving portion includes a light-emitting region and a sensor region; thus, a thin, lightweight, and highly portable food-sorting device can be formed at low costs. Note that the structure illustrated in FIG. 18B may be used for the food-sorting device. Alternatively, the structure illustrated in FIG. 18C may be used for the non-destructive testing device.

FIG. 19A1 illustrates an example in which a plurality of sensor modules and the like are worn on a body. The sensor modules each include at least one sensor of an infrared sensor, a near-infrared sensor, a temperature sensor, an acceleration sensor, and the like, and include a secondary battery, a detecting device, a communication module, and the like. The sensor modules have a function of sampling an induction waveform used in an electrocardiogram or the like, a function of sensing body temperature, a function of sensing a pulse, a function of sensing a blood sugar level or the like, a function of sensing the amount of movement of arms and legs, and the like.

An example in which sensor modules LA, RA, LL, and RL are worn on arms and legs is described. The use of the plurality of sensor modules allows an electrocardiogram shown in FIG. 19B1 for checking whether or not anomaly such as heart arrhythmia occurs to be obtained. For example, the sensor module LA is worn on a left arm, the sensor module RA is worn on a right arm, the sensor module LL is worn on a left leg, and the sensor module RL is worn on a right leg. Note that the arm includes an upper arm, a wrist, a palm, a finger, and the like. The leg includes a thigh, a calf, a shin, an ankle, an instep, a sole, a toe, and the like.

It is known that a first induction waveform (Waveform 1), a second induction waveform (Waveform 2), and a third induction waveform (Waveform 3) in the electrocardiogram are compared for judgement. That is, the sensor module LA obtains, as Waveform 1, the amount of change with the RA used as a reference. The sensor module LL obtains, as Waveform 2, the amount of change with the RA used as a reference. The sensor module LL obtains, as Waveform 3, the amount of change with the LA used as a reference. Note that the signal mn1 generated by the semiconductor device 80 preferably drives the sensor modules LA, RA, LL, and RL in synchronization with each other. Since the semiconductor device 80 is composed of the dynamic circuit and thus has low power consumption, data of a long period of time can be obtained.

Data may be shared among the sensor modules. Alternatively, the data may be transmitted to a portable data terminal in FIG. 19A2 with or without a wire, and Waveform 1 to Waveform 3 may be detected in the portable data terminal. The portable data terminal can detect whether or not a problem such as arrhythmia occurs from the data obtained by the sensor modules. In the case where the data obtained by the sensor modules is transmitted to the portable data terminal with a wire, it is preferable that data obtained by the time of connection with a wire be collectively transmitted. Note that dates may be automatically given to the detected data, and the data may be stored in the portable data terminal and managed personally. Alternatively, the data may be transmitted to a hospital or the like through a network (including the Internet). The data can be managed in a data server of a hospital and used as inspection data in treatment. Note that the portable data terminal can have the structure illustrated in FIG. 17A.

In the case where the above sensor modules further include a plurality of microneedles and the like, a value of current flowing between the microneedles or a resistance value can be measured. That is, the sensor modules can detect a blood sugar level in the blood (FIG. 19B2) and the like by measuring the conductivity between the microneedles.

When the above sensor modules each include an acceleration sensor, the amount of exercise (movement) of arms and legs can be detected. Individual management of the amount of exercise of arms and legs can detect whether or not the balance of the amount of exercise of a body is lost.

As described above, when the plurality of sensor modules are worn on a body, the portable data terminal can detect in what state arrhythmia or the like occurs in daily life. The use of information such as a body temperature (FIG. 19B3), a pulse (FIG. 19B4), and a blood sugar level in the case where arrhythmia occurs enables correct management of a body or correct diagnosis of a disorder in a hospital.

The above sensor modules may be directly attached to a body with a sticker or the like, may be embedded in a body, or may be a wearable electronic device such as a wristwatch. Note that the sensor modules may have all the functions described above or one or more of the functions.

This embodiment can be implemented in combination with any of the structures described in the other embodiments and the like, as appropriate.

Example 1

Figure 20:
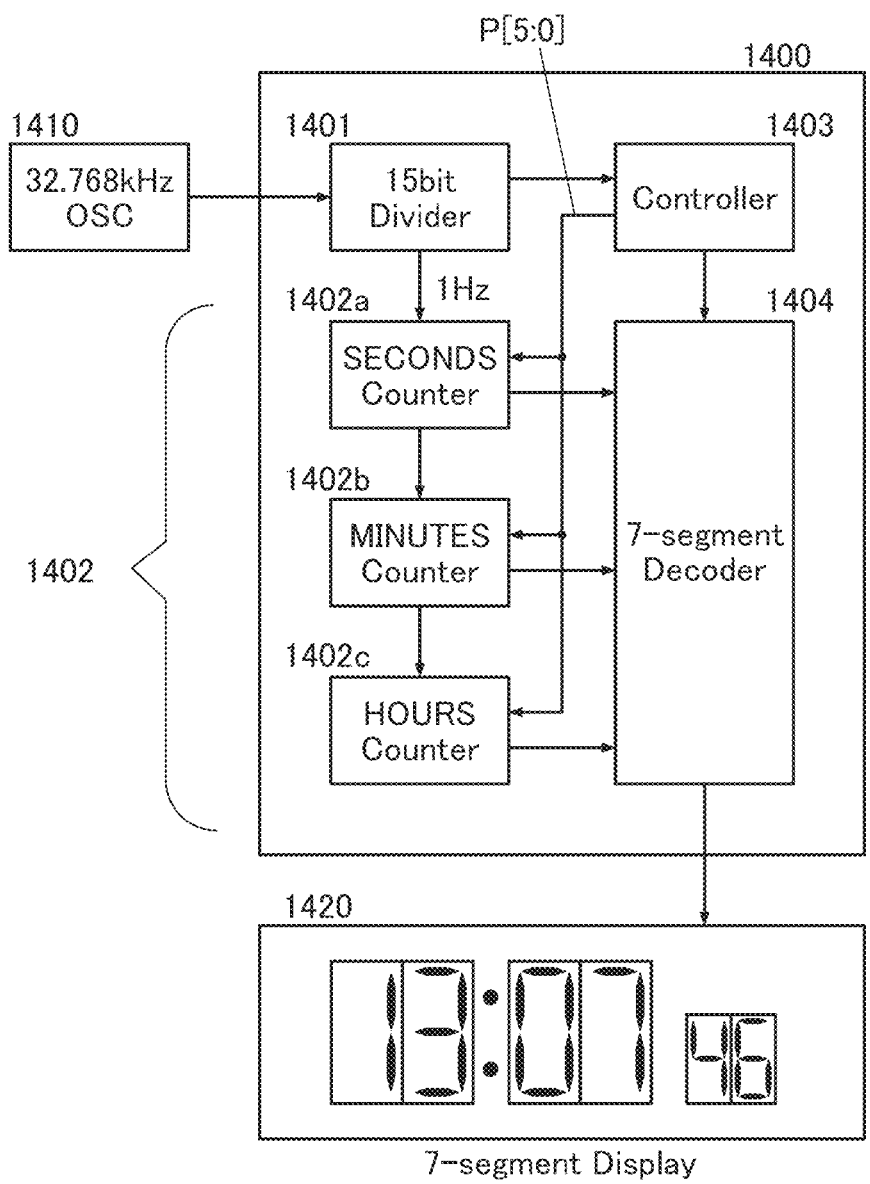
FIG. 20 is a block diagram illustrating a prototype device.

In this example, a device for a wearable watch that uses the dynamic circuit described in Embodiment 1 will be described. FIG. 20 is a block diagram of the prototype device for a wearable watch. The device for a wearable watch (hereinafter, referred to as a device 1400) includes an oscillator (OSC) 1410, a frequency divider (15-bit Divider) 1401, a counter circuit (Counter) 1402, a control circuit (Controller) 1403, a decoder circuit (7-segment Decoder) 1404, and a display device (7-segment Display) 1420. The counter circuit 1402 includes a counter circuit (SECONDS Counter) 1402a counting "SECONDS", a counter circuit (MINUTES Counter) 1402b counting "MINUTES", and a counter circuit (HOURS Counter) 1402c counting "HOURS". The counter circuit 1402a and the counter circuit 1402b are each composed of a decade counter and a senary counter. The counter circuit 1402c is composed of a decade counter and a ternary counter. The decoder circuit 1404 has a function of displaying the time easily by controlling seven segments that can display numbers. Note that the latch circuit composed of the dynamic circuit described in Embodiment 1 is applicable to the frequency divider 1401, the counter circuit 1402, the control circuit 1403, and the decoder circuit 1404.

An output of 32.768 kHz from the oscillator 1410 is divided 15 times by the frequency divider 1401 to generate a 1-Hz clock signal. The 1-Hz clock signal is supplied to the counter circuit 1402a and the control circuit 1403. The counter circuit 1402a counts the seconds with the 1-Hz clock signal. Note that the counter circuit 1402a can supply a carry out signal to the counter circuit 1402b. Furthermore, the counter circuit 1402b can supply a carry out signal to the counter circuit 1402c.

The control circuit 1403 generates six-phase clock signals P[5:0] from the clock signal. The clock signals P[5:0] can be supplied to the counter circuit 1402a, the counter circuit 1402b, and the counter circuit 1402c. The control circuit 1403 can supply a control signal to the decoder circuit 1404.

The counter circuit 1402a supplies the count value of "seconds" to the decoder circuit 1404, the counter circuit 1402b supplies the count value of "minutes" to the decoder circuit 1404, and the counter circuit 1402c supplies the count value of "hours" to the decoder circuit 1404.

The decoder circuit 1404 converts the count value of "seconds" supplied from the counter circuit 1402a into 7-segment data and supplies it to the display device 1420, converts the count value of "minutes" supplied from the counter circuit 1402b into 7-segment data and supplies it to the display device 1420, and converts the count value of "hours" supplied from the counter circuit 1402c into 7-segment data and supplies it to the display device 1420.

Figure 21A:
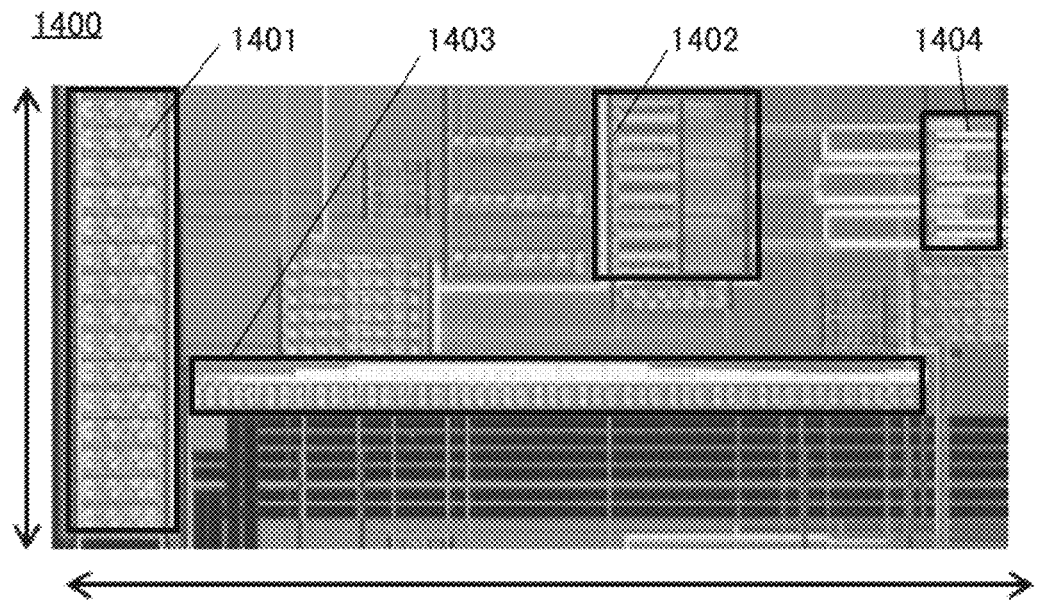
FIG. 21A is a photograph of a prototype device.

FIG. 21A shows a photograph of the appearance of the prototype device 1400. The device 1400 was formed using a technology of a 350-nm Top-gate-self-aligned CAAC-IGZO FET stacked on a Si-Wafer. The frequency divider 1401, the counter circuit 1402, the control circuit 1403, and the decoder circuit 1404 illustrated in FIG. 20 were formed as the device 1400 over the Si-Wafer.

The chip size of the device 1400 is 0.9 mm×1.92 mm. In the device 1400, approximately 12000 transistors were used.

Figure 21B:
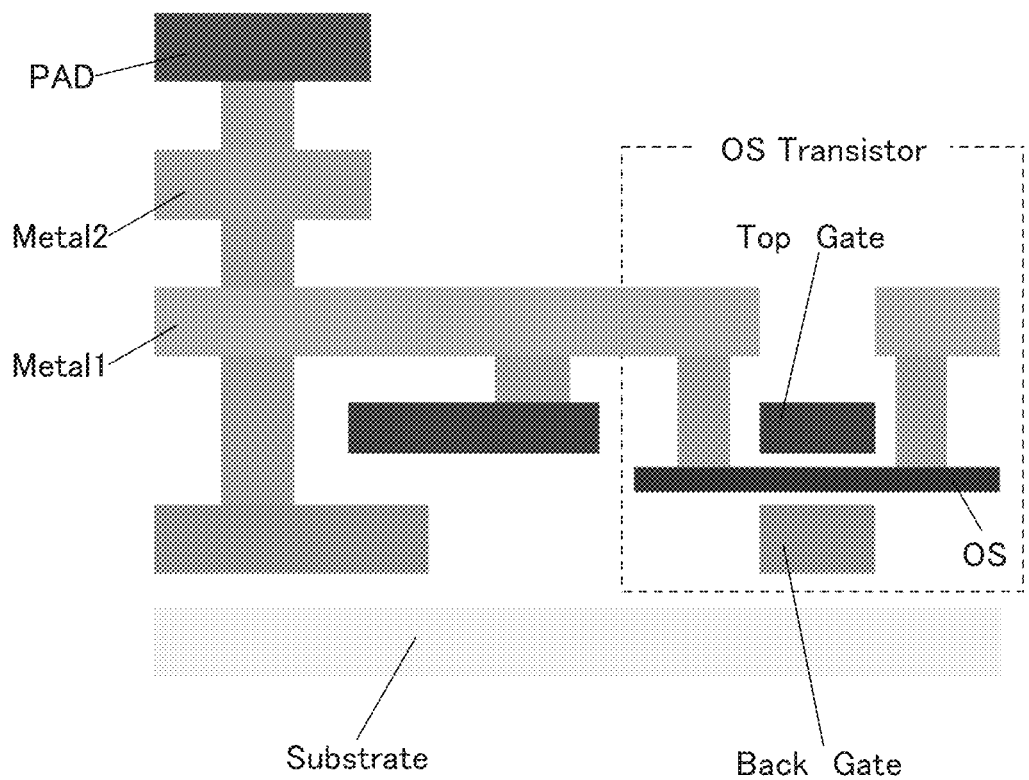
FIG. 21B is a diagram illustrating a cross section of a transistor.

FIG. 21B is a schematic cross-sectional view of a transistor used in the device for a wearable watch. A back gate (Back Gate) was formed over a Si-Wafer (substrate), and a semiconductor layer (OS) and atop gate (Top Gate) formed using a conductive layer were provided in this order over the back gate formed using a conductive layer. The top gate, the semiconductor layer, and the back gate overlap with one another, so that the transistor is formed. Note that a transistor including a metal oxide in a semiconductor layer is referred to as an OS transistor. Parts of the bottom gate and the top gate were used as wirings. The conductive layers (Metal 1 and Metal 2) were used as wiring layers. Moreover, a PAD for inputting and outputting a signal was provided over the conductive layers.

Figure 22:
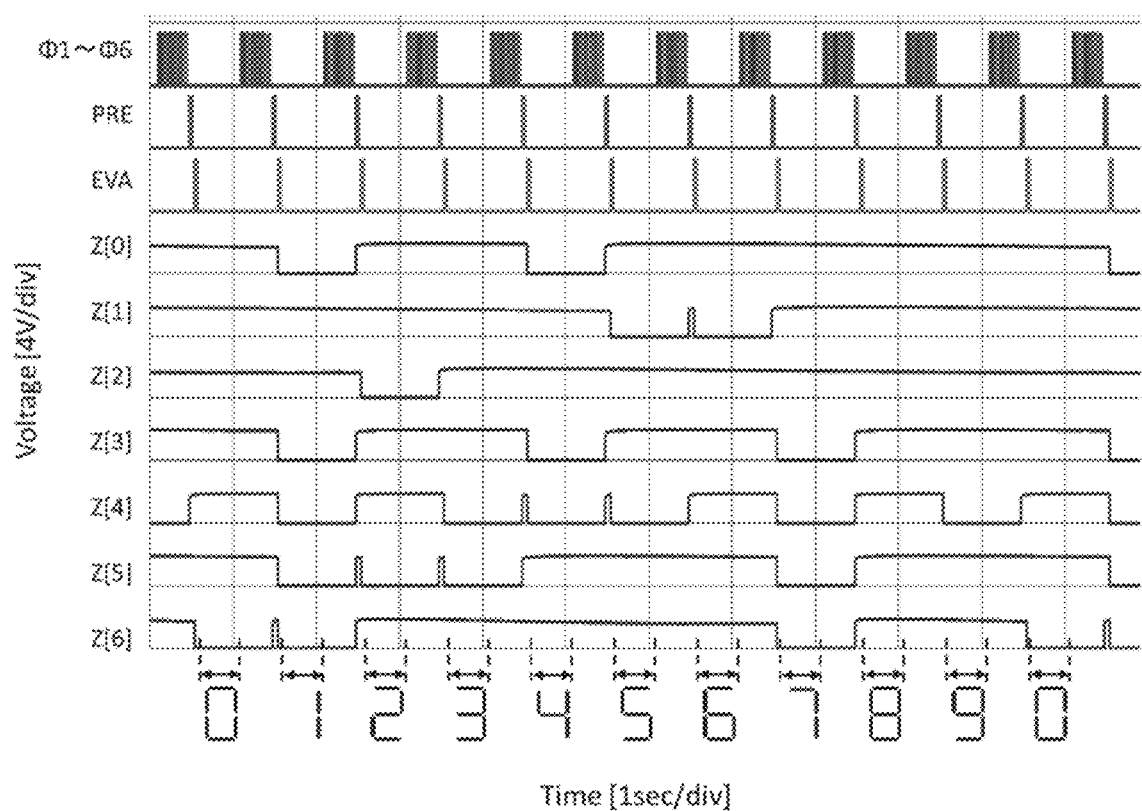
FIG. 22 is a diagram showing measurement data of a prototype device.

FIG. 22 shows waveforms measured when the device 1400 operates. Note that it was confirmed that the device 1400 operated normally in a positive power supply voltage range from 3.3 V to 4 V. Note that the clock signals P0 to P5 are represented as clock signals Φ1 to Φ6. Control signals (the signal PRE and a signal EVA) are signals supplied from the control circuit 1403 to the decoder circuit 1404. Note that the signal PRE and the signal EVA correspond to the signal PRE and the signal EN1, respectively, illustrated in FIG. 15. Output signals Z0 to Z6 are supplied from the decoder circuit 1404 to the display device 1420, and the display device 1420 displays numbers by turning on any of seven segments with the output signals Z0 to Z6.

Figures 23A, 23B:
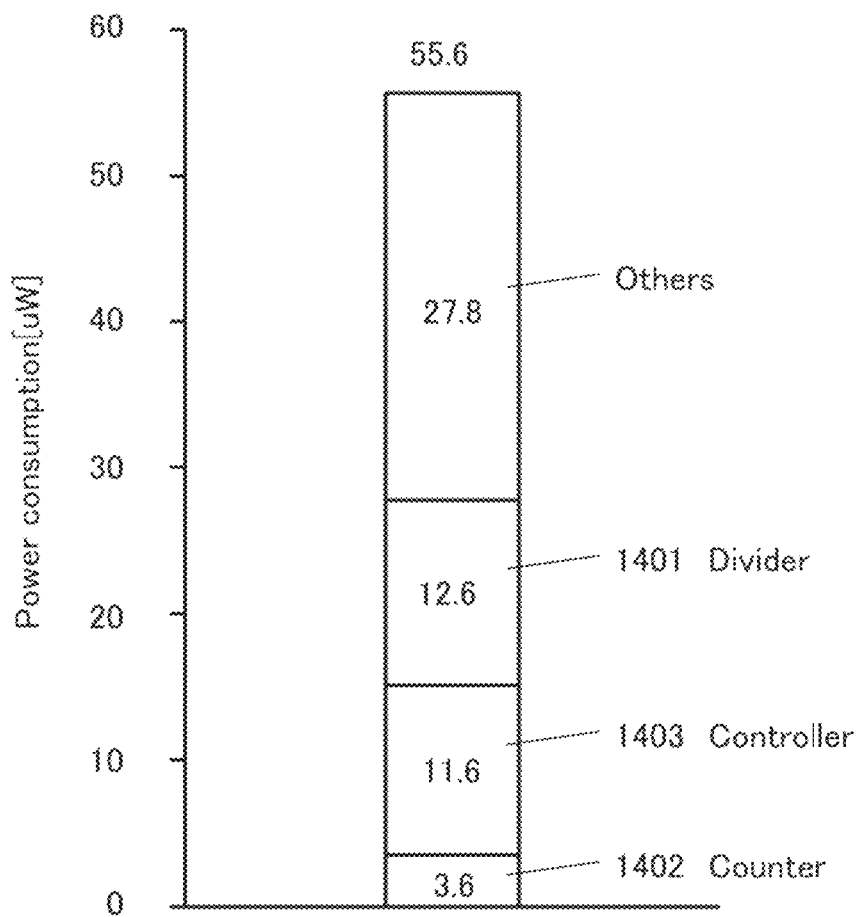
FIG. 23A is simulation data of a prototype device.
FIG. 23B is measurement data of a prototype device.

FIG. 23A shows the simulation results of power consumption in the case where the device 1400 operates in the simulation. When a positive power supply voltage was 3.3 V, the power consumption of the device 1400 was 55.6 uW. The details of the power consumption of the device 1400 were as follows: the frequency divider 1401, 12.6 uW; the counter circuit 1402, 3.6 uW; the control circuit 1403, 11.6 uW; and the others, 27.8 uW.

FIG. 23B shows the results of the power consumption measured when the prototype device 1400 operates. As described above, the device 1400 is composed of the dynamic circuit (Dynamic Logic circuit). The positive power supply voltage was 3.3 V. The current consumption of the device 1400 was 90 uA. Therefore, the power consumption was calculated to be 297 uW. Note that the setting parameters of the gate insulating film in the simulation differ from those of the gate insulating film of the prototype device 1400; thus, the difference exists between the simulation results in FIG. 23A and the power consumption of the device 1400 in FIG. 23B.

The device for a wearable watch was fabricated using, as a circuit that operates at low speed, a functional circuit formed using an OS transistor with low off-state current. A dynamic technology was employed to obtain a logic circuit with low shoot-through current using only the OS transistor; as a result, a wearable system with extremely low power consumption was achieved.

REFERENCE NUMERALS

BG1: wiring, BG2: wiring, BG3: wiring, BG4: wiring, BG5: wiring, C1: capacitor, C2: capacitor, C3: capacitor, C4: capacitor, C5: capacitor, 3A: transistor, 3B: transistor, 3C: transistor, 3D: transistor, 3E: transistor, 3F: transistor, 3G: transistor, 3H: transistor, 3J: transistor, 3K: transistor, 10: latch circuit, 10A: latch circuit, 10B: latch circuit, 10C: latch circuit, 10CA: circuit, 10CAa: circuit, 10CAb: circuit, 10D: latch circuit, 10E: latch circuit, 10F: latch circuit, 10G: latch circuit, 10H: latch circuit, 10J: latch circuit, 10K: latch circuit, 11: transistor, 11a: transistor, 12: transistor, 12a: transistor, 13: transistor, 13a: transistor, 14: transistor, 14a: transistor, 15: transistor, 15a: transistor, 16: transistor, 16a: transistor, 17: transistor, 17a: transistor, 18: transistor, 18a: transistor, 19: transistor, 19a: transistor, 20: circuit, 20A: circuit, 20B: circuit, 20C: circuit, 20D: circuit, 20E: circuit, 20F: circuit, 20G: circuit, 20H: circuit, 20J: circuit, 20K: circuit, 21: transistor, 21a: transistor, 30: circuit, 30A: circuit, 30B: circuit, 30C: circuit, 30D: circuit, 30E: circuit, 30F: circuit, 30G: circuit, 30H: circuit, 30J: circuit, 30K: circuit, 31: transistor, 32: transistor, 33: transistor, 34: transistor, 35: transistor, 36: transistor, 37: transistor, 38: transistor, 39: transistor, 40: circuit, 41: transistor, 41a: transistor, 42: transistor, 42a: transistor, 50: circuit, 51: transistor, 51a: transistor, 52: transistor, 52a: transistor, 61: transistor, 61a: transistor, 62: transistor, 62a: transistor, 63: transistor, 64: transistor, 65: transistor, 66: transistor, 80: semiconductor device, 81: control circuit, 82: oscillator, 83: frequency divider, 84: circuit, 84a: circuit, 84b: circuit, 84c: circuit, 86: decoder circuit, 87: selector circuit, 88a: display device, 88b: display device, 88c: display device, 88d: display device, 88e: display device, 88f: display device, 90: battery protection IC, 300: transistor, 314: insulating layer, 322: insulating layer, 324: insulating layer, 330: oxide layer, 500: electronic device, 911: housing, 912: operation button, 913: sensor device, 914: wireless communication unit, 921: housing, 922: operation panel, 923: transfer mechanism, 924: monitor, 925: detecting unit, 926: testing target member, 927: sensor device, 931: housing, 932: operation button, 933: display portion, 934: light-blocking hood, 935: sensor device, 1300: transistor, 1300A: transistor, 1305: conductive layer, 1314: insulating layer, 1316: insulating layer, 1322: insulating layer, 1324: insulating layer, 1330: oxide layer, 1330a: oxide layer, 1330b: oxide layer, 1330c: oxide layer, 1340: conductive layer, 1340a: conductive layer, 1340b: conductive layer, 1341: insulating layer, 1341a: insulating layer, 1341b: insulating layer, 1342: conductive layer, 1342a: conductive layer, 1342b: conductive layer, 1350: insulating layer, 1354: insulating layer, 1360: conductive layer, 1360a: conductive layer, 1360b: conductive layer, 1374: insulating layer, 1380: insulating layer, 1381: insulating layer, 1400: device, 1401: frequency divider, 1402: counter circuit, 1402a: counter circuit, 1402b: counter circuit, 1402c: counter circuit, 1403: control circuit, 1404: decoder circuit, 1410: oscillator, 1420: display device

The invention claimed is:

1. A semiconductor device comprising a latch circuit composed of a dynamic circuit,
   wherein the latch circuit comprises a first circuit, first to third capacitors, first to third clock input terminals, a signal input terminal, a first output terminal, and a second output terminal,
   wherein the first circuit is configured to perform decoding, wherein the first to third clock input terminals are configured to be supplied with first to third clock signals, respectively, wherein, in a period during which an "H" signal is supplied to the first clock signal:
the first circuit is configured to be supplied with a plurality of input signals through the signal input terminal; and
a potential of the first capacitor is configured to be updated on the basis of a result of decoding performed by the first circuit, wherein, in a period during which the "H" signal is supplied to the second clock signal:
a potential of the second capacitor is configured to be updated on the basis of the potential of the first capacitor; and
the first output terminal is configured to be supplied with the potential of the second capacitor as a first output signal, and wherein, in a period during which the "H" signal is supplied to the third clock signal:
a potential of the third capacitor is configured to be updated on the basis of the potential of the second capacitor; and
the second output terminal is configured to be supplied with the potential of the third capacitor as a second output signal.

2. The semiconductor device according to claim 1, wherein the latch circuit comprises fourth to sixth clock input terminals,
wherein fourth to sixth clock signals are sequentially supplied to the fourth to sixth clock input terminals,
wherein the first capacitor is precharged in a period during which the "H" signal is supplied to the fourth clock signal,
wherein the second capacitor is precharged in a period during which the "H" signal is supplied to the fifth clock signal, and
wherein the third capacitor is precharged in a period during which the "H" signal is supplied to the sixth clock signal.

3. The semiconductor device according to claim 1,
wherein the latch circuit comprises a second circuit,
wherein the second circuit generates a seventh clock signal and an eighth clock signal from the second clock signal supplied to the second clock input terminal,
wherein the latch circuit is configured to latch a result of decoding the input signal and outputting the latch result to the first output signal in a period during which the "H" signal is supplied to the seventh clock signal, and
wherein, in a period during which the "H" signal is supplied to the eighth clock signal:
the second capacitor is precharged by supply of the fifth clock signal to the fifth clock input terminal;
a potential of the precharged second capacitor is output as the "H" signal to the first output signal when the first output signal is the "H" signal;
the potential of the second capacitor is discharged by the second output signal when the first output signal is an "L" signal; and
the potential of the second capacitor is output as the "L" signal to the first output signal.

4. The semiconductor device according to claim 1, comprising a plurality of the latch circuits which are cascade-connected,
wherein the cascade-connected latch circuits are configured as a counter circuit.

5. The semiconductor device according to claim 1,
wherein the latch circuit comprises first to fifth transistors,
wherein the first clock input terminal is electrically connected to a gate of the first transistor,
wherein the third clock input terminal is electrically connected to a gate of the third transistor,
wherein the fifth clock input terminal is electrically connected to a gate of the fifth transistor,
wherein one electrode of the second capacitor is electrically connected to a gate of the fourth transistor,
wherein one electrode of the third capacitor is electrically connected to the gate of the fifth transistor,
wherein the first to fifth transistors each comprise a metal oxide in a semiconductor layer,
wherein the first to fifth transistors each comprise a back gate, and
wherein a potential supplied to the back gates of the first to third transistors is different from a potential supplied to the back gates of the fourth and fifth transistors.

6. A detecting device comprising the semiconductor device according to claim 4, a detecting circuit, and a battery,
wherein an output signal of the semiconductor device is supplied to the detecting circuit, and
wherein the detecting circuit uses the output signal as a monitor cycle for monitoring an output potential of the battery.

* * * * *